(12) United States Patent
Roberts et al.

(10) Patent No.: US 6,316,208 B1
(45) Date of Patent: Nov. 13, 2001

(54) METHODS FOR DETERMINING ISOLATED P27 PROTEIN LEVELS AND USES THEREOF

(75) Inventors: James M. Roberts; Peggy L. Porter, both of Seattle, WA (US); Kornelia Polyak, Roslindale, MA (US); Joan Massague, New York; Andrew Koff, Westbury, both of NY (US)

(73) Assignees: Memorial Sloan-Kettering Cancer Center, New York; Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 08/794,002

(22) Filed: Feb. 3, 1997

Related U.S. Application Data

(63) Continuation-in-part of application No. PCT/US95/07361, filed on Jun. 7, 1995, which is a continuation-in-part of application No. 08/275,983, filed on Jul. 15, 1994, now Pat. No. 5,688,665, which is a continuation-in-part of application No. 08/179,045, filed on Jan. 7, 1994, now abandoned.

(51) Int. Cl.⁷ .................. G01N 33/53; G01N 33/573
(52) U.S. Cl. .................. 435/7.21; 435/7.1; 435/7.8; 435/7.4
(58) Field of Search ............ 435/7.8, 7.1, 7.21, 435/7.4

(56) References Cited

U.S. PATENT DOCUMENTS 5,688,665   11/1997   Massague et al. ............... 435/69.2

OTHER PUBLICATIONS

Polyak et al. Genes and Development 8(1994)9–22.*
Rudinger In "Peptide Hormones" (Jun. 1976) ed J.A. Parsons, University Park Press, Baltimore, pp. 1–7.*
Akama et al., "Genetic Status and Expression of the Cyclin–dependent Kinase Inhibitors in Human Gastric Carcinoma Cell Lines", *Jpn. J. Cancer Res.*, 87(8): 824–830 (1996).
Deng et al., "A Novel Expression Vector for High–Level Synthesis and Secretion of Foreign Proteins in Escherichia Coli: Overproduction of Bovine Pancreatic Phospholipase $A_2$", *Gene*, 93: 229–234 (1990).
Firpo et al., "Inactivation of a Cdk2 Inhibitor During Interleukin 2–induced Proliferation of Human T Lymphocytes", *Mol. Cell. Biol.*, 14: 4889–4901 (1994).
Harper et al., "The p21 Cdk–interacting Protein Cip 1 is a Potent Inhibitor of G1 Cyclin–dependent Kinases", *Cell*, 75: 805–816 (1993).

Hengst and Reed, "Translational Control of p27Kip 1 Accumulation During the Cell Cycle", *Science*, 271(5257): 1861–1864 (1996).
Koff et al., "Formation and Activation of a Cyclin E–cdk2 Complex During the G1 Phase of the Human Cell Cycle", *Science*, 257: 1689–1694 (1992).
Lloyd et al., "Aberrant $p27^{kip1}$ Expression in Endocrine and Other Tumors", *Am. J. Pathol.*, 150(2): 401–407 (1997).
Loda, et al., "Increased Proteasome–dependent Degradation of the Cyclin–dependent Kinase Inhibitor p27 in Aggressive Colorectal Carcinomas", *Nat. Med.*, 3(2): 231–234 (1997).
Medin et al., "Efficient, Low–cost Protein Factories: Expression of Human Adenosie Deaminase in Baculovirus–infected Insect Larvae", *PNAS USA*, 87: 2760–2764 (1990).
Morosetti et al., "Alterations of the $p27^{KIP1}$ Gene in Non–Hodgkin's Lymphomas and Audlt T–cell Leukemia/Lymphoma", *Blood*, 86(5): 1924–1930 (1995).
Polyak et al., "Cloning of $p27^{kip1}$, a Cyclin–dependent Kinase Inhibitor and a Potential Mediator of Extracelluar Antimitogenic Signals", *Cell*, 78: 59–66 (1994).
Polyak et al., "$p27^{Kip1}$, a Cyclin–Cdk Inhibitor Links Transforming Growth Factor–β and Contact Inhibition to Cell Cycle Arrest", *Genes & Dev.*, 8: 9–22 (1994).
Rivard et al., "Abrogation of $p27^{Kip1}$ by cDNA Antisense Suppresses Quiescence ($G_0$ State) in Fibroblasts", *J. Biol. Chem.*, 271(31): 18337–18341 (1996).
St. Croix et al., "Impact of the Cyclin–dependent Kinase Inhibitor $p27^{Kip1}$ on Resistance Tumor Cells to Anticancer Agents", *Nat. Med.* 2(11): 1204–1210 (1996).
Soos et al., "Formation of p27–CDK Complexes During the Human Mitotic Cell Cycle", *Cell Growth Differ.*, 7(2): 135–146 (1996).
Tempst al., "Internal Sequence Analysis of Proteins Separated on Polyacrylamide Gels at the Submicrogram Level: Improved Methods, Applications and Gene Cloning Strategies", *Electrophoresis*, 11: 537–553 (1990).
Toyoshima and Hunter, "p27, A Novel Inhibitor of G1 Cyclin–Cdk Protein Kinase Activity, is Related to p21", *Cell*, 78: 67–74 (1994).
Van Dyke et al., "Single–step Purification of Bacterially Expressed Polypeptides Containing an Oligo–histidine Domain" Gene, 111 99–104 (1992).

* cited by examiner

*Primary Examiner*—Christina Y. Chan
*Assistant Examiner*—Robert C. Hayes
(74) *Attorney, Agent, or Firm*—Foley, Hoag & Eliot, LLP; Matthew P. Vincent; David P. Halstead

(57) ABSTRACT

The subject invention is directed to the discovery of a protein involved in regulation of cell-cycle progression, and includes reagents and methods related thereto.

13 Claims, 32 Drawing Sheets

IN VITRO
TRANSLATION

VECTOR | KIP1 | kd
--- | --- | ---
 | | −200
 | | −98
 | | −69
 | | −46
 | | −30
 | | −21

Fig. 8D

```
                        20                          40
mk kip1  MSNVRVSNGSPSLERMDARQAEYPKPSACRNLFGPVNHEELTRDLEKHRR
m  kip1  .................DH........................C.
h  kip1  .................H.............D...........C.

70                          90
mk kip1  DMEEASQRKWNFDFQNHKPLEGKYEWQEVEKGSLPEFYYRPPRPPKGACK
m  kip1  ..................R.......R.................S...
h  kip1  ..................................................

120                         140
mk kip1  VPAQESQDVSGTRQAVPLMGSQANSEDTHLVDQKTDTADNQAGLAEQCTG
m  kip1  .L........S......I........R.....MP.SS..........P.
h  kip1  ...........S.P.A..I.AP..........P...PS.S.T...DR.A.

170                         190
mk kip1  IRKRPATDDSSPQNKRANRTEENVSDGSxxxxxxxxxxxxxxxxxxxxx
m  kip1  M.....AE...S................PNAGTVEQTPKKPGLRR-QT
h  kip1  ...........T................S.............R..
```

Fig. 9A

```
h kip1  MSNVRVSNGSPSLERMDARQAEHPKPSACPNLFGPVDHEELTRDLEKHCR  50
h cip1          MSEPAGDVRQNPCGSHACPRLFGPVDSEQLSRDCDALMA  39 h kip1  DMEEASQRKWNFDFQNHKPLEGKYEWQEVEKGSLPEFYYRPPRPPKGACK  100
h cip1  GCIQEAREFWNFDFVTETPLEGDFAWERVRGLGLPKLYLPTGPRRGRDEL   89 h kip1  VPAQESQDVSGSRPAAPLIGAPANSEDTHLVDPKTDPSDSQTGLADRCAG  150
h cip1  GGGRRPGTSPALLQGTAEEDHVDLSLSCTLVPRSGEQAEGSPGGPGDSQG  139 h kip1  IRKRPATDDSSTQ-NKRANRTEENVSDGSPNAGSVEQTPKKPGLRRRQT*  198
h cip1  -RKRRQTSMTDFYHSKRRLIFSKRKP*                         164
```

Fig. 9B

```
ATG TCA AAC GTG CGG GTG TCT AAC GGG AGC CCG AGC CTG GAG CGG ATG      48
Met Ser Asn Val Arg Val Ser Asn Gly Ser Pro Ser Leu Glu Arg Met
 1               5                  10                  15

GAC GCC AGA CAG GCG GAG TAC CCC AAG CCC TCC GCC TGC AGA AAC CTC      96
Asp Ala Arg Gln Ala Glu Tyr Pro Lys Pro Ser Ala Cys Arg Asn Leu
             20                  25                  30

TTC GGC CCG GTC AAC CAC GAA GAG CTG ACC CGG GAC TTG GAG AAG CAC     144
Phe Gly Pro Val Asn His Glu Glu Leu Thr Arg Asp Leu Glu Lys His
             35                  40                  45

CGC AGA GAC ATG GAA GAG GCA AGC CAG CGC AAG TGG AAT TTT GAT TTC     192
Arg Arg Asp Met Glu Glu Ala Ser Gln Arg Lys Trp Asn Phe Asp Phe
         50                  55                  60

CAG AAT CAC AAG CCC CTG GAG GGC AAA TAC GAG TGG CAG GAG GTG GAG     240
Gln Asn His Lys Pro Leu Glu Gly Lys Tyr Glu Trp Gln Glu Val Glu
 65                  70                  75                  80

AAG GGC AGC TTG CCG GAG TTC TAC TAC AGA CCC CCG CGG CCA CCC AAA     288
Lys Gly Ser Leu Pro Glu Phe Tyr Tyr Arg Pro Pro Arg Pro Pro Lys
                 85                  90                  95

GGC GCC TGC AAG GTG CCG GCG CAG GAG AGC CAG GAC GTC AGC GGG ACC     336
Gly Ala Cys Lys Val Pro Ala Gln Glu Ser Gln Asp Val Ser Gly Thr
                100                 105                 110

CGG CAG GCC GTG CCT TTA ATG GGG TCT CAG GCA AAC TCA GAG GAC ACA     384
Arg Gln Ala Val Pro Leu Met Gly Ser Gln Ala Asn Ser Glu Asp Thr
            115                 120                 125

CAC TTG GTA GAC CAA AAG ACT GAC ACG GCG GAC AAC CAG GCT GGC TTA     432
His Leu Val Asp Gln Lys Thr Asp Thr Ala Asp Asn Gln Ala Gly Leu
        130                 135                 140

GCG GAG CAG TGC ACT GGG ATC AGG AAG CGA CCG GCC ACA GAC GAT TCC     480
Ala Glu Gln Cys Thr Gly Ile Arg Lys Arg Pro Ala Thr Asp Asp Ser
145                 150                 155                 160

TCT CCT CAA AAC AAA AGA GCC AAC AGA ACA GAA GAA AAT GTC TCA GAC     528
Ser Pro Gln Asn Lys Arg Ala Asn Arg Thr Glu Glu Asn Val Ser Asp
                165                 170                 175

GGT TCC                                                              534
Gly Ser
```

Fig. 13A

| | | | | | | | | | | | | | | |
|---|---|---|---|---|---|---|---|---|---|---|---|---|---|---|
| Met | Ser | Asn | Val | Arg | Val | Ser | Asn | Gly | Ser | Pro | Ser | Leu | Glu | Arg | Met |
| 1 | | | | 5 | | | | | 10 | | | | | 15 | |

```
Met Ser Asn Val Arg Val Ser Asn Gly Ser Pro Ser Leu Glu Arg Met
 1               5                   10                  15

Asp Ala Arg Gln Ala Glu Tyr Pro Lys Pro Ser Ala Cys Arg Asn Leu
                 20                  25                  30

Phe Gly Pro Val Asn His Glu Glu Leu Thr Arg Asp Leu Glu Lys His
             35                  40                  45

Arg Arg Asp Met Glu Glu Ala Ser Gln Arg Lys Trp Asn Phe Asp Phe
         50                  55                  60

Gln Asn His Lys Pro Leu Glu Gly Lys Tyr Glu Trp Gln Glu Val Glu
 65                  70                  75                  80

Lys Gly Ser Leu Pro Glu Phe Tyr Tyr Arg Pro Pro Arg Pro Pro Lys
                 85                  90                  95

Gly Ala Cys Lys Val Pro Ala Gln Glu Ser Gln Asp Val Ser Gly Thr
            100                 105                 110

Arg Gln Ala Val Pro Leu Met Gly Ser Gln Ala Asn Ser Glu Asp Thr
            115                 120                 125

His Leu Val Asp Gln Lys Thr Asp Thr Ala Asp Asn Gln Ala Gly Leu
    130                 135                 140

Ala Glu Gln Cys Thr Gly Ile Arg Lys Arg Pro Ala Thr Asp Asp Ser
145                 150                 155                 160

Ser Pro Gln Asn Lys Arg Ala Asn Arg Thr Glu Glu Asn Val Ser Asp
                165                 170                 175

Gly Ser
```

Fig. 13B

```
ATG TCA AAC GTG AGA GTG TCT AAC GGG AGC CCG AGC CTG GAG CGG ATG     48
Met Ser Asn Val Arg Val Ser Asn Gly Ser Pro Ser Leu Glu Arg Met
 1               5                  10                  15

GAC GCC AGA CAA GCG GAT CAC CCC AAG CCT TCC GCC TGC AGA AAT CTC     96
Asp Ala Arg Gln Ala Asp His Pro Lys Pro Ser Ala Cys Arg Asn Leu
                20                  25                  30

TTC GGC CCG GTC AAT CAT GAA GAA CTA ACC CGG GAC TTG GAG AAG CAC    144
Phe Gly Pro Val Asn His Glu Glu Leu Thr Arg Asp Leu Glu Lys His
            35                  40                  45

TGC CGG GAT ATG GAA GAA GCG AGT CAG CGC AAG TGG AAT TTC GAC TTT    192
Cys Arg Asp Met Glu Glu Ala Ser Gln Arg Lys Trp Asn Phe Asp Phe
        50                  55                  60

CAG AAT CAT AAG CCC CTG GAG GGC AGA TAC GAA TGG CAG GAG GTG GAG    240
Gln Asn His Lys Pro Leu Glu Gly Arg Tyr Glu Trp Gln Glu Val Glu
 65                 70                  75                  80

AGG GGC AGC TTG CCC GAG TTC TAC TAC AGG CCC CCG CGC CCC CCC AAG    288
Arg Gly Ser Leu Pro Glu Phe Tyr Tyr Arg Pro Pro Arg Pro Pro Lys
                85                  90                  95

AGC GCC TGC AAG GTG CTG GCG CAG GAG AGC CAG GAT GTC AGC GGG AGC    336
Ser Ala Cys Lys Val Leu Ala Gln Glu Ser Gln Asp Val Ser Gly Ser
            100                 105                 110

CGC CAG GCG GTG CCT TTA ATT GGG TCT CAG GCA AAC TCT GAG GAC CGG    384
Arg Gln Ala Val Pro Leu Ile Gly Ser Gln Ala Asn Ser Glu Asp Arg
        115                 120                 125

CAT TTG GTG GAC CAA ATG CCT GAC TCG TCA GAC AAT CAG GCT GGG TTA    432
His Leu Val Asp Gln Met Pro Asp Ser Ser Asp Asn Gln Ala Gly Leu
 130                135                 140

GCG GAG CAG TGT CCA GGG ATG AGG AAG CGA CCT GCT GCA GAA GAT TCT    480
Ala Glu Gln Cys Pro Gly Met Arg Lys Arg Pro Ala Ala Glu Asp Ser
145                 150                 155                 160

TCT TCG CAA AAC AAA AGG GCC AAC AGA ACA GAA GAA AAT GTT TCA GAC    528
Ser Ser Gln Asn Lys Arg Ala Asn Arg Thr Glu Glu Asn Val Ser Asp
                165                 170                 175

GGT TCC CCG AAC GCT GGC ACT GTG GAG CAG ACG CCC AAG AAG CCC GGC    576
Gly Ser Pro Asn Ala Gly Thr Val Glu Gln Thr Pro Lys Lys Pro Gly
            180                 185                 190

CTT CGA CGC CAG ACG TAA                                             594
Leu Arg Arg Gln Thr
        195
```

Fig. 14A

Met Ser Asn Val Arg Val Ser Asn Gly Ser Pro Ser Leu Glu Arg Met
 1           5                  10                  15

Asp Ala Arg Gln Ala Asp His Pro Lys Pro Ser Ala Cys Arg Asn Leu
         20                  25                  30

Phe Gly Pro Val Asn His Glu Glu Leu Thr Arg Asp Leu Glu Lys His
         35                  40                  45

Cys Arg Asp Met Glu Glu Ala Ser Gln Arg Lys Trp Asn Phe Asp Phe
     50                  55                  60

Gln Asn His Lys Pro Leu Glu Gly Arg Tyr Glu Trp Gln Glu Val Glu
 65                  70                  75                  80

Arg Gly Ser Leu Pro Glu Phe Tyr Tyr Arg Pro Pro Arg Pro Pro Lys
             85                  90                  95

Ser Ala Cys Lys Val Leu Ala Gln Glu Ser Gln Asp Val Ser Gly Ser
         100                 105                 110

Arg Gln Ala Val Pro Leu Ile Gly Ser Gln Ala Asn Ser Glu Asp Arg
         115                 120                 125

His Leu Val Asp Gln Met Pro Asp Ser Ser Asp Asn Gln Ala Gly Leu
     130                 135                 140

Ala Glu Gln Cys Pro Gly Met Arg Lys Arg Pro Ala Ala Glu Asp Ser
145                 150                 155                 160

Ser Ser Gln Asn Lys Arg Ala Asn Arg Thr Glu Glu Asn Val Ser Asp
             165                 170                 175

Gly Ser Pro Asn Ala Gly Thr Val Glu Gln Thr Pro Lys Lys Pro Gly
             180                 185                 190

Leu Arg Arg Gln Thr
         195

Fig. 14B

```
ATG TCA AAC GTG CGA GTG TCT AAC GGG AGC CCT AGC CTG GAG CGG ATG     48
Met Ser Asn Val Arg Val Ser Asn Gly Ser Pro Ser Leu Glu Arg Met
 1               5                  10                  15

GAC GCC AGG CAG GCG GAG CAC CCC AAG CCC TCG GCC TGC AGG AAC CTC     96
Asp Ala Arg Gln Ala Glu His Pro Lys Pro Ser Ala Cys Arg Asn Leu
                20                  25                  30

TTC GGC CCG GTG GAC CAC GAA GAG TTA ACC CGG GAC TTG GAG AAG CAC    144
Phe Gly Pro Val Asp His Glu Glu Leu Thr Arg Asp Leu Glu Lys His
            35                  40                  45

TGC AGA GAC ATG GAA GAG GCG AGC CAG CGC AAG TGG AAT TTC GAT TTT    192
Cys Arg Asp Met Glu Glu Ala Ser Gln Arg Lys Trp Asn Phe Asp Phe
        50                  55                  60

CAG AAT CAC AAA CCC CTA GAG GGC AAG TAC GAG TGG CAA GAG GTG GAG    240
Gln Asn His Lys Pro Leu Glu Gly Lys Tyr Glu Trp Gln Glu Val Glu
 65                  70                  75                  80

AAG GGC AGC TTG CCC GAG TTC TAC TAC AGA CCC CCG CGG CCC CCC AAA    288
Lys Gly Ser Leu Pro Glu Phe Tyr Tyr Arg Pro Pro Arg Pro Pro Lys
                85                  90                  95

GGT GCC TGC AAG GTG CCG GCG CAG GAG AGC CAG GAT GTC AGC GGG AGC    336
Gly Ala Cys Lys Val Pro Ala Gln Glu Ser Gln Asp Val Ser Gly Ser
                100                 105                 110

CGC CCG GCG GCG CCT TTA ATT GGG GCT CCG GCT AAC TCT GAG GAC ACG    384
Arg Pro Ala Ala Pro Leu Ile Gly Ala Pro Ala Asn Ser Glu Asp Thr
            115                 120                 125

CAT TTG GTG GAC CCA AAG ACT GAT CCG TCG GAC AGC CAG ACG GGG TTA    432
His Leu Val Asp Pro Lys Thr Asp Pro Ser Asp Ser Gln Thr Gly Leu
        130                 135                 140

GCG GAG CAA TGC GCA GGA ATA AGG AAG CGA CCT GCA ACC GAC GAT TCT    480
Ala Glu Gln Cys Ala Gly Ile Arg Lys Arg Pro Ala Thr Asp Asp Ser
145                 150                 155                 160

TCT ACT CAA AAC AAA AGA GCC AAC AGA ACA GAA GAA AAT GTT TCA GAC    528
Ser Thr Gln Asn Lys Arg Ala Asn Arg Thr Glu Glu Asn Val Ser Asp
                165                 170                 175

GGT TCC CCA AAT GCC GGT TCT GTG GAG CAG ACG CCC AAG AAG CCT GGC    576
Gly Ser Pro Asn Ala Gly Ser Val Glu Gln Thr Pro Lys Lys Pro Gly
                180                 185                 190

CTC AGA AGA CGT CAA ACG TAA                                        597
Leu Arg Arg Arg Gln Thr
                195
```

Fig. 15A

```
Met Ser Asn Val Arg Val Ser Asn Gly Ser Pro Ser Leu Glu Arg Met
 1           5                   10                      15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                      70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
            165                 170                 175

Gly Ser Pro Asn Ala Gly Ser Val Glu Gln Thr Pro Lys Lys Pro Gly
            180                 185                 190

Leu Arg Arg Arg Gln Thr
        195
```

Fig. 15B

OVERALL SURVIVAL

| PROGNOSTIC FACTOR[a] | UNIVARIATE (P)[b] | RR[c] | MULTIVARIATE (P) | RR[c] |
|---|---|---|---|---|
| POSITIVE LYMPH NODES | <0.001 | 4.5 (2.8-7.0) | <0.001 | 4.5 (2.3-8.8) |
| TUMOR SIZE (cm) | | | | |
| 2-4+ | <0.001 | 2.8 (1.6-4.9) | 0.09 | 1.9 (0.9-4.0) |
| 5 or > | <0.001 | 7.0 (3.1-15.9) | 0.08 | 2.9 (0.9-9.7) |
| HISTOLOGICAL GRADE | | | | |
| INTERMEDIATE | 0.007 | 3.1 (1.4-6.9) | 0.37 | 1.6 (0.6-4.8) |
| HIGH | <0.001 | 3.9 (1.7-8.6) | 0.18 | 2.1 (0.7-6.4) |
| c-erbB-2 | <0.001 | 2.4 (1.5-3.9) | 0.04 | 2.0 (1.1-3.9) |
| P53 | 0.10 | 1.5 (0.9-2.5) | 0.90 | 1.0 (0.4-2.2) |
| Ki-67 High | 0.40 | 1.2 (0.8-2.0) | 0.49 | 0.7 (0.3-1.7) |
| HIGH CYCLIN E LEVEL | 0.001 | 2.1 (1.3-3.3) | 0.03 | 2.4 (1.1-5.2) |
| LOW P27 LEVEL | <0.001 | 2.9 (1.7-4.9) | 0.01 | 2.7 (1.3-6.0) |

[a]CATEGORIES OF THE PROGNOSTIC FACTORS ARE LISTED IN TABLE 1. [b]COX REGRESSION MODEL USED TO EVALUATE MULTIVARIATE PREDICTIVE VALUE OF PROGNOSTIC FACTORS; RESULTS ARE SHOWN AS P (REGRESSION COEFFICIENT +/- SE). [c]RELATIVE RISK DETERMINED BY COX REGRESSION MODEL. NINETY FIVE PERCENT CONFIDENCE INTERVALS IN PARENTHESES.

Fig. 17

METHODS FOR DETERMINING ISOLATED P27 PROTEIN LEVELS AND USES THEREOF

RELATED APPLICATIONS

This application is a continuation-in-part of PCT application PCT/US 95/07361, filed Jun. 7, 1995, which is a continuation-in-part U.S. Ser. No. 08/275,983, filed Jul. 15, 1994, now U.S. Pat. No. 5,688,665, which is a continuation-in-part of U.S. Ser. No. 08/179,045, filed Jan. 7, 1994, now abandoned, the specification of which are incorporated by reference herein.

This invention was made with support under Grant No. CA48718 from the National Institutes of Health. Accordingly, the U.S. government has certain rights in the invention.

BACKGROUND OF THE INVENTION

Throughout this application, various publications are referenced. The disclosures of these publications are hereby incorporated by reference into this application to describe more fully the art to which this invention pertains.

Progression through the cell cycle is marked by a series of irreversible transitions that separate discrete tasks necessary for faithful cell duplication. These transitions are negatively regulated by signals that constrain the cell cycle until specific conditions are fulfilled. Entry into mitosis, for example, is inhibited by incompletely replicated DNA or DNA damage (Weiner and Hartwell, 1988). Another feedback pathway delays the transition from M to G1 if the mitotic spindle is defective (Hoyt et al. (1991); Li & Murray (1991). These restrictions on cell cycle progression are essential for preserving the fidelity of the genetic information during cell division (HArtwell & WEinert (1989)). The transition from G1 to S phase, on the other hand, coordinates cell proliferation with environmental cues, after which the checks on cell cycle progression tend to be cell autonomous (Hartwell et al. (1974); Pardee (1974); Pardee (1989)). Among the extracellular influences that restrict cell cycle progression during G1 are proteins that inhibit cell proliferation, growth factor or amino acid depletion, and cell-cell contact. Disruption of these signaling pathways uncouples cellular responses from environmental controls and may lead to unrestrained cell proliferation.

Transitions between phases of the cell cycle are catalyzed by a family of cyclin-dependent kineses (Cdks) (Nurse (1990); Hartwell (1991)). In some organisms the physiological signals controlling the G2 to M transition target a series of steps that activate the mitotic Cdk, Cdc2. Cdc2 activation is positively regulated by phosphorylation on threonine-161 (Booher & Beach (1986); Krek & Nigg (1991); Gould K. et al. (1991) EMBO J. 10:3297–3309; Solomon et al. (1990); Solomon et al. (1992)) and negatively by phosphorylation on tyrosine-15 (Gould K. & Nurse P. (1989) Nature 342:39–45). Incomplete DNA replication delays dephosphorylation of tyr-15 (Dasso M. & Newport J. (1990) Cell 61:811–823; Smythe & Newport (1992)), and mutations in Cdc2 that convert tyr-15 to a nonphosphorylatable residue are lethal and cause a premature mitosis (Gould & Nurse (1989) supra). Similarly, either over expression of the tyr-15 phosphatase, Cdc25 (Enoch T. & Nurse P. (1990) Cell 60:665–673; Kumagai & Dunphy (1991)), or loss of the tyr-15 kinases (Ludgren et al. (1991)) bypass the requirement that DNA replication be completed before mitosis begins. Additional levels of control are probably required to fully explain the block to mitosis caused by ongoing DNA replication (Sorger & Murray (1992); Heald et al. (1993); Stueland et al. (1993)). There is also evidence that cell cycle arrest induced by DNA damage may be related to inactivation of Cdc2 (Rowley et al. (1992); Walworth et al. (1993)), but the role of tyrosine phosphorylation in this context has been questioned (Barbel & Carr (1993)).

There is some evidence, particularly in yeast, that signals inhibiting the G1 to S phase transition block Cdk activation. The mating pheromone alpha factor arrests the S. cerevisiae cell cycle in G1 Reid & Hartwell (1977)), and this correlates with a decrease in CDC28 kinase activity and a decline in the abundance of active complexes containing G1 cyclins and CDC28 (Wittenberg et al. (1990)). The FAR1 protein binds to G1 cyclin-CDC28 complexes in cells treated with alpha factor, and this is probably necessary for cell cycle arrest (Chang F. & Herskowitz I. (1990) Cell 63:999–1011; Peter et al. (1993)). Other inhibitors of CDC28 kinase activity have been identified, but their relationship to physiological signals that control cell cycle progression is not known (Mendenhall (1993); Dunphy W. & Newport J. (1989) Cell 58:181–191).

Mammalian cells, like yeast, require cyclin-dependent kineses for progression through G1 and entry into S phase (D'Urso G. et al. (1990) Science 250:786–791; Blow J. J. & Nurse P. (1990) Cell 62:855–862; Furukawa et al. (1990); Fang F. & Newport J. (1991) Cell 66:731–742; Pagano et al. (1993); Tsai et al. (1993)). Both D and E-type cyclins are rate limiting for the G1 to S transition and both reduce, but do not eliminate, the cell's requirement for mitogenic growth factors (Ohtsubo & Roberts (1993); Quelle et al. (1993)). There is little information, however, concerning the manner by which these cyclins and Cdks are negatively regulated by extracellular signals that inhibit cell proliferation.

It has been studied how two signals that block the cell cycle in G1, cell-cell contact and TGF-β, affect the activity of a G1 cyclin-dependent kinase, Cdk2 (Paris et al. (1990); Elledge S. & Spottswood M. (1991) EMBO J. 10:2653–2659; Koff et al. (1991); Tsai et al. (1991); Elledge S. et al. (1992) Proc. Natl. Acad. Sci. USA 89:2907–2911; Rosenblatt et al. (1992)). The cell cycle of MvlLu mink epithelial cells can be arrested in G1 by growth to high density. These contact inhibited cells express both cyclin E and Cdk2, but cyclin E-associated kinase activity is not present (Koff et al. (1993). Entry into S phase can also be prevented if MvlLu cells are released from contact inhibition in the presence of TGF-β, and this correlates with a block to phosphorylation of the Retinoblastoma (Rb) protein (Laiho et al. (1990)). Both Cdk2 and Cdk4 have been implicated as Rb kinases (Matsushime et al. (1992); Hinds et al. (1993); Kato et al. (1993); Ewen M. et al. (1993a) Cell 73:487–497; Dowdy S. et al. (1993) Cell 73:499–511), suggesting that TGF-β induced cell cycle arrest may involve inhibition of Cdks during G1 (Howe et al. (1991)). Consistent with this, cells arrested in late G1 by TGF-β, like contact inhibited cells, express both cyclin E and Cdk2 but do not contain catalytically active cyclin E-Cdk2 complexes (Koffet al. (1993)). Cdk4 synthesis is also repressed by TGF-β. The inactivity of Cdk2 together with the absence of Cdk4 may explain the block to Rb phosphorylation in these cells.

It is shown herein that contact inhibited and TGF-βtreated cells, but not proliferating cells, contain a titratable excess of a 27 kD protein that binds to the cyclin E-Cdk2 complex and prevents its activation. The inhibitory activity of p27 can be competed by the cyclin D2-Cdk4 complex, suggesting that p27 and cyclin D2-Cdk4 may function within a pathway that transmits growth inhibitory signals to Cdk2.

The subject invention provides an isolated 27 kD protein capable of binding to and inhibiting the activation of a cyclin E-Cdk2 complex. The subject invention further provides related recombinant nucleic acid molecules, host vector systems, and methods for making same. Finally, the subject invention provides methods of identifying agents and using agents which act on or mimic p27 function, so as to exploit the regulatory role of p27 in cell proliferation.

SUMMARY OF THE INVENTION

The subject invention provides an isolated protein having an apparent molecular weight of about 27 kD as measured by SDS polyacrylamide gel electrophoresis, and capable of binding to and inhibiting the activation of a cyclin E-Cdk2 complex.

The subject invention further provides a recombinant nucleic acid molecule which encodes the protein of the subject invention.

The subject invention further provides a vector comprising the recombinant nucleic acid molecule of the subject invention.

The subject invention further provides a host vector system for the production of a protein having an apparent molecular weight of about 27 kD as measured by SDS polyacrylamide gel electrophoresis, and capable of binding to and inhibiting the activation of a cyclin E-Cdk2 complex, which comprises the vector of the subject invention in a suitable host.

The subject invention further provides a method for producing a protein having an apparent molecular weight of about 27 kD as measured by SDS polyacrylamide gel electrophoresis, and capable of binding to and inhibiting the activation of a cyclin E-Cdk2 complex, which comprises growing the host vector system of the subject invention under conditions permitting the production of the protein and recovering the protein produced thereby.

The subject invention further provides a method of determining whether an agent is capable of specifically inhibiting the ability of p27 protein to inhibit the ability of p27 protein to inhibit the activation of cyclin E-Cdk2 complex which comprises: (a) contacting suitable amounts of p27 protein, cyclin E, Cdk2 and the agent under suitable conditions; (b) subjecting the p27, cyclin E, Cdk2 and agent so contacted to the conditions which would permit the formation of active cyclin E-Cdk2 complex in the absence of p27 protein; (c) quantitatively determining the amount of active cyclin E-Cdk2 complex so formed; and (d) comparing the amount of active cyclin E-Cdk2 complex so formed with the amount of active cyclin E -Cdk2 complex formed in the absence of the agent, a greater amount of active cyclin E-Cdk2 complex formed in the presence of the agent than in the absence of the agent indicating that the agent is capable of specifically inhibiting the ability of p27 protein to inhibit the activation of cyclin E-Cdk2 complex.

The subject invention further provides a method of determining whether an agent is capable of specifically enhancing the ability of p27 protein to inhibit the activation of cyclin E-Cdk2 complex which comprises: (a) contacting suitable amounts of p27 protein, cyclin E, Cdk2 and the agent under suitable conditions; (b) subjecting the p27, cyclin E, Cdk2, and agent so contacted to conditions which would permit the formation of active cyclin E-Cdk2 complex in the absence of p27 protein; (c) quantitatively determining the amount of active cyclin E-Cdk2 complex so formed; and (d) comparing the amount of active cyclin E-Cdk2 complex so formed with the amount of active cyclin E-Cdk2 complex formed in the absence of the agent, a lesser amount of active cyclin E-Cdk2 complex formed in the presence of the agent than in the absence of the agent indicating that the agent is capable of specifically enhancing the ability of p27 protein to inhibit the activation of cyclin E-Cdk2 complex.

The subject invention further provides a method of treating a subject having a hyperproliferative disorder which comprises administering to the subject a therapeutically effective amount of an agent capable of specifically enhancing the ability of p27 protein to inhibit the activation of cyclin E-Cdk2 complex in the hyperproliferative cells of the subject, so as to thereby treat the subject.

The subject invention further provides a method of treating a subject having a hypoproliferative disorder which comprises administering to the subject a therapeutically effective amount of an agent capable of specifically inhibiting the ability of p27 protein to inhibit the activation of cyclin E-Cdk2 complex in the hypoproliferative cells of the subject, so as to thereby treat the subject.

In another aspect, the present invention provides a method for determining the relative amount of p27 protein in a cell or sample of cells (cell sample) comprising (i) determining the level of p27 protein in the cell sample, and (ii) comparing the level of p27 protein in the cell sample with the level of p27 protein determined for a control cell.

In yet another embodiment, the invention provides a method for determining the amount of p27 protein in a cell or sample of cells (cell sample) comprising (i) contacting the cell sample with an antibody selectively reactive with the p27 protein under conditions sufficient for the antibody and p27 protein to bind, and (ii) determining the amount of p27 protein bound by the antibody.

The subject invention further provides a method of diagnosing a hyperproliferative disorder in a subject, which disorder is associated with the presence of a p27 protein mutation in the cells of the subject, which comprises determining the presence of a p27 protein mutation in the cells of the subject, said mutation being associated with a hyperproliferative disorder, so as to thereby diagnose a hyperproliferative disorder in the subject.

Moreover, the subject method can be used for diagnosing a hyperproliferative disorder in a patient which disorder is associated with the destabilization of a p27 protein in cells of the patient, comprising: (i) ascertaining the level of p27 protein in a sample of cells from the patient; and (ii) diagnosising the presence or absence of a hyperproliferative disorder utilizing, at least in part, the ascertained level of p27 protein, wherein a reduced level of p27 protein in the sample, relative to a normal control sample of cells, correlates with the presence of a hyperproliferative disorder. In another embodiment, the subject method is a prognostic method for evaluating a cancer patient's risk of death and/or recurrence of a cancer, comprising (i) ascertaining the level of p27 protein in a sample of cancer cells from the patient; and (ii) predicting the patient's risk of death and/or recurrence of a cancer utilizing, at least in part, the ascertained level of p27 protein, wherein a reduced level of p27 protein in the sample, relative to a normal control sample of cells, correlates with an increased risk of death and/or recurrence of a cancer.

The present invention also provides a test kit for detecting p27 protein comprising an antibody, or fragment thereof, which selectively binds to a p27 protein, e.g., the antibody selectively binds to the p27 protein of SEQ ID No. 2. In preferred embodiments, the antibody is labeled with a detectable label, e.g., with a label selected from the group consisting of radioisotopes, fluorescent compounds, enzymes, and enzyme co-factors.

The subject invention further provides a pharmaceutical composition which comprises an effective amount of a recombinant virus capable of infecting a suitable host cell, said recombinant virus comprising the nucleic acid molecule of the subject invention, and a pharmaceutically acceptable carrier.

Finally, this invention provides a method for treating a subject suffering from a hyperproliferative disorder associated with the presence of a p27 protein mutation in the cells of the subject, which comprises administering to the subject an amount of the pharmaceutical composition of the subject invention effective to treat the subject.

Figure 1A:
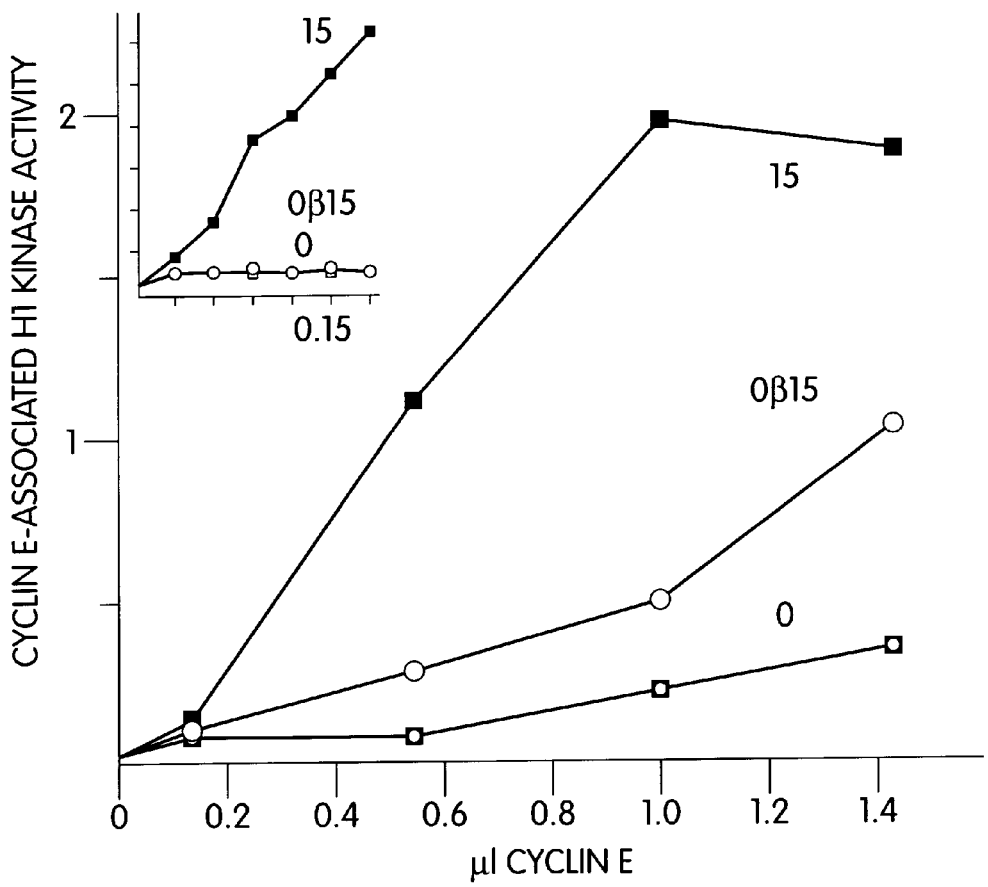
FIG. 1A

Activation of Cdk2 by Cyclin E in Extracts from Proliferating and Growth Arrested Cells Cyclin E was added to extracts from contact inhibited cells (0), and cells released from contact inhibition for 15 hours in the presence (0β15) or absence (15) of TGF-β. The 15 hour cells are referred to in the text as "proliferating cells" to indicate that they are progressing through the cell cycle and have entered S phase. 0.05 µl of cyclin E corresponds to physiological levels of cyclin E in these extracts. The inset shows the titration of up to 3 times physiological levels of cyclin E. Cyclin E immunoprecipitates were assayed for histone H1 kinase activity and the results quantitated using a phosphorimager. Background levels of phosphorylation observed in the absence of exogenous cyclin E were subtracted from each sample.

FIG. 1B

Activation of Cdk2 by Cyclin E in Extracts from Proliferating and Growth Arrested Cells Extracts were prepared from contact inhibited cells (0), and cells released from contact inhibition for 15 hours in the presence (0β15) or absence (15) of TGF-β. Physiological amounts of cyclin E were added to various amounts of these extracts and to mixtures of extracts. Extracts from proliferating and arrested cells were mixed in the indicated proportions, and the total amount of protein in each mixture was 75 µg. The amount of each extract used (µg) is indicated. After incubation, cyclin E was immunoprecipitated and assayed for H1 kinase activity. Results were quantitated using a phosphorimager. Background levels of phosphorylation observed in the absence of exogenous cyclin E were subtracted from each sample.

FIG. 2A

A Cdk2 Inhibitor Binds to Cyclin E-Cdk2 Complexes

The indicated extracts were incubated with Cdk2-sepharose beads (K), cyclin E-Cdk2 sepharose beads (EK), or blank sepharose beads (0). The Cdk2 beads contained twofold more Cdk2 than present in the cell extract. The cyclin E-Cdk2 beads contained approximately 60-fold more cyclin E than was present in the cell extract. After incubation, a portion of each supernatant was analyzed by Western blotting to confirm that neither cyclin E nor CDK2 had leached from the matrices. The remainder of the supernatant was assayed for Cdk2 activation by addition of 2X physiological amounts of cyclin E. Cyclin E immunoprecipitates were assayed for H1 kinase activity and the results quantitated using a phsophorimager. Partial depletion of inhibitor by the Cdk2 beads may be attributable to the formation of cyclin-Cdk2 complexes during the incubation with the cell extract.

FIG. 2B

A Cdk2 Inhibitor Binds to Cyclin E-Cdk2 Complexes

Cdk2 was immunoprecipitated from extracts of contact inhibited cells (0), and cells released from contact inhibition for 15 hours in the presence (0β15) or absence (15) of TGF-β. Half of each immunoprecipitate was incubated with cyclin E plus CAK, and the other half underwent mock incubation. Each immuno-precipitate was then assayed for histone H1 kinase activity and the results quantitated using a phosphorimager. In the absence of added CAK, cyclin E had only a very small activating effect on immunoprecipitated Cdk2 (data not shown).

FIG. 2C

A Cdk2 Inhibitor Binds to Cyclin E-Cdk2 Complexes

Effect of kinase inactive Cdk2 on cyclin E activity in extracts from growth arrested cells. Each extract was incubated with 5-fold excess of cyclin E (just at the cyclin E threshold for this lyeste), 0.5-fold excess of kinase inactive Cdk2 (Cdk2K), or both. These proportions were chosen based upon empirical determinations of the maximum amount of Cdk2K that could be added without sequestering the majority of the added cyclin E. Cyclin E immunoprecipitates were assayed for H1 kinase activity and the results quantitated using a phosphorimager.

FIG. 3A

Activation of Cdc2 by Cyclin B

Cyclin B and Cyclin E were added to extracts from cells released from contact inhibition for 15 hours in the presence (0β15) or absence (15) of TGF-β. After addition of cyclins the extracts were divided and immunoprecipitated with either antisera directed to the C-terminus of Cdc2 or the C-teminus of Cdk2. The immunoprecipitates were assayed for H1 kinase activity and the products resolved on a 12% polyacrylatde gel. The reactions labeled "endogenous" contain no added cyclin.

FIG. 3B

Activation of Cdc2 by Cyclin B

Cyclin B was added to extracts from cells released from contact inhibition for 15 hours in the presence (0β15) or absence (15) of TGF-β. Half of each reaction was supplemented with purified CAK. Cdc2 was immunoprecipitated with antibody directed towards the C-terminus of Cdc2 and assayed for H1 kinase activity. The results were quantitated using a phosphorimager.

FIG. 4A

Effect of Cyclin D-Cdk4 Complexes on Cyclin E Activity

Extracts were prepared from contact inhibited cells (0), and cells released from contact inhibition for 15 hours in the presence (0β15) or absence (15) of TGF-β. 0.05 microliters of Sf9 cell lysates containing cyclin D2, Cdk4, cyclin D2-Cdk4 complexes, or complexes containing cyclin D2 bound to catalytically inactive Cdk4 (Cdk4K) were added to these extracts together with physiological amounts of cyclin E. These amounts of cyclin D2 and Cdk4 closely correspond to physiological amounts of these proteins. Cyclin E was immunoprecipitated and assayed for associated histone H1 kinase activity.

FIG. 4B

Effect of Cyclin D-Cdk4 Complexes on Cyclin E Activity

Extracts were prepared from cells released from contact inhibition for 15 hours in the presence (0β15) or absence (15) of TGF-β. 0.05 microliters of Sf9 cell lysates containing the indicated cyclin D-Cdk4 complexes were added to these extracts in the presence or absence of cyclin E. Cyclin E was immunoprecipitated and assayed for associated histone H1 kinase activity.

FIG. 5A

A 27 kD Cyclin E-Cdk2 Binding Protein

Contact inhibited MvlLu cells were released from quiescence by replating at lower density and extracts prepared from 35S-methionine labeled cells at 0 and 15 h. Some cultures were incubated in the presence of 100 pM TGF-β for 15 h (0β15). These metabolically labeled extracts were treated as described and bound proteins eluted in sample buffer and analyzed by SDS-PAGE followed by fluorography. Migration of molecular weight markers are shown. 35S-methionine labeled cell extracts were incubated with Cdk2 or cyclin E-Cdk2 complexes and bound proteins eluted in sample buffer. The arrow indicates the migration of a 27 kD protein (p27) specifically associated with cyclin E-Cdk2 complexes in extracts from contact inhibited and TGF-β treated cells.

FIG. 5B

A 27 kD Cyclin E-Cdk2 Binding Protein

Extracts from metabolically labeled contact inhibited MvlLu cells were incubated with varying amounts of Cdk2 or cyclin E-Cdk2 relative to standard conditions and bound proteins analyzed as described below. The presence of p27 is indicated (arrow).

FIG. 5C

A 27 kD Cyclin E-Cdk2 Binding Protein

Cyclin D2-Cdk4 complexes prevent binding of p27 to cyclin E-Cdk2. Extracts from contact inhibited cells were preincubated with 4 μl of baculovirus produced cyclin D2-Cdk4 complex for 30 minutes at 4° C. prior to addition of the cyclin E-Cdk2 complex.

FIG. 5D

A 27 kD Cyclin E-Cdk2 Binding Protein

Recovery of p27 in Cdk4 immunoprecipitates. Supernatants from 5C were immunoprecipitated with an anti-Cdk4 antiserum and immunoprecipitates were analyzed on 12% SDS-PAGE. The open arrow at 34 kD shows the endogenous mink Cdk4 protein, while the closed arrow indicates p27, associated with the cyclin D2-Cdk4 complexes.

FIG. 6A

Heat Stability of p27 and the Cdk2 Inhibitor p27 binding is heat stable and p27 call be recovered from proliferating cell extracts by heat treatment. MvlLu cells were released from contact inhibition for 15 hours with (0β15) or without (15) TGF-β. Cells were metabolically labeled using 35S-methionine. Prior to incubation with Cdk2 or cyclin E-Cdk2 complexes, cell extracts received either no pretreatment or were heated to 100° C. for 3 minutes. Note the appearance of p27 (arrow) in heat treated 15 h cell extract.

FIG. 6B

Heat Stabililty of p27 and the Cdk2 Inhibitor

Cdk2 inhibitory activity can be recovered from proliferating cell extracts by heat treatment. Cyclin E associated kinase activity was measured in extracts from asynchronous proliferating cells by immunoprecipitation with antibodies against human cyclin E. Histone H1 was the substrate and results were quantitated using a phosphorimager. Lane 1—no additions; Lane 2—the extract was supplemented with 3 times physiological amounts of cyclin E; Lane 3—as in lane 2 except that heat treated extract from proliferating cells (see methods) was also added to the cell extract.

FIG. 6C

Heat Stability of p27 and the Cdk2 Inhibitor

Cdk2 inhibitory activity was heat stable. Extracts were prepared from contact inhibited cells (0), cells released from contact inhibition for 48 hours in the presence of TGF-β (0β48) or asynchronous proliferating cells (Exp). Cyclin E associated kinase activity measured with or without addition of exogenous cyclin E. In the indicated lanes, proliferating cell extracts were mixed with an equal amount of extract from nonproliferating cells that had either been untreated or heated to 100° C. for 5 minutes.

FIG. 7A

Inhibition of Cyclin E-associated Kinase Activity by Purified p27

Extracts from metabolically labeled contact inhibited MvlLu cells were subjected to chromatography on Cdk2 or cyclin E-Cdk2 affinity columns. Bound proteins, eluted in low pH buffer, and were analyzed by SDS-PAGE. p27 present in cyclin E-Cdk2 eluates is shown (arrow).

FIG. 7B

Eluates from Cdk2 or cyclin E-Cdk2 columns were precipitated with acetone and renatured (see methods). A portion of each eluate was added to an extract from proliferating cells. Cyclin E was added and cyclin E associated histone H1 kinase activity measured. The cyclin E associated H1 kinase activity was quantitated and plotted as % inhibition relative to extracts receiving no additions.

FIG. 7C

Renatured eluates were incubated with Cdk2 or cyclin E-Cdk2 complexes. p27 (arrow) bound to cyclin E-Cdk2 after renaturation.

FIG. 7D

Eluates from cyclin E-cdk2 columns were fractionated on 12% acrylamide gels. The gels were sliced as shown and proteins were eluted and renatured. A portion of the protein recovered from each gel slice was added together with cyclin E to extracts prepared from proliferating MvlLu cells. Cyclin E immunoprecipitates were assayed for histone H1 kinase activity.

FIGS. 8A, 8B, 8C and 8D

Purification, Cyclin E-Cdk2 Interaction, and in vitro Translation of Kip1

(A) Heat-treated extracts from quiescent MvlLu cells were subjected to cyclin E-Cdk2 affinity chromatography. The eluate was resolved by SDS-PAGE and silver stained. $p27^{Kip1}$ is indicated by an arrow. The broad band is Cdk2-HA, and the 69 kd band is a contaminant present also in blank lanes. (B) Extracts from metabolically labeled quiescent MvlLu cells were precipitated with preimmune rabbit serum (control) or anti-Cdk2 antibody. (C) Metabolically-labeled p27 obtained by coprecipitation with anti-Cdk2 antibodies as in panel B (in vivo p27) or by cyclin E-Cdk2 affinity chromatography as in panel A (in vivo p27) was digested with V8 protease and displayed by SDS-PAGE and fluorography. (D) In vitro translations containing empty vector (vector) or vector encoding histidine-tagged mouse Kip1 (Kip1) were bound to $Ni^{++}$-NTA-agarose, boiled in sample buffer and resolved by SDS-PAGE.

FIGS. 9A and 9B

Mammalian Kip1 Sequences, and Comparison with Cip1/WAF1

(A) Amino acid sequences deduced from Kip1 cDNAs from mink (mk), (SEQ ID No. 22) mouse (m) and human (h). Identical amino acids are indicated by dots. The available mink sequence is incomplete at the C-terminus. Peptide sequences obtained from purified Kip1 are underlined. Thick underlining indicates the two sequences that served to design degenerate oligonucleotides for PCR. (B) Sequence alignment between human Kip1 and Cip1/WAF1 (SEQ ID No. 23). The putative bipartite nuclear localization signal in both proteins is underlined. A Cdc2 kinase consensus site present in Kip1 is indicated by a thick bar.

FIGS. 10A, 10B, 10C, 10D and 10E

Cdk Inhibition by Kip1 in vitro, and Identification of a Cdk Inhibitory Domain of Kip1

Cell lyeates containing baculoviral cyclin E and Cdk2 (A, C) or the indicated cyclin/Cdk combinations, were assayed for histone H1 kinase activity (A, B) and Rb kinase activity (C, D) in the presence of the indicated concentrations of Kip1. Representative gels containing the phosphorylated substrates are shown (A, C). Relative phosphorylation levels were quantitated, and are plotted as the percentage of phosphorylation observed in reactions without Kip1. (E) Schematic of the Kip1 protein indicating the regions of highest homology to Cip1/WAF1 (shaded boxes; see also FIG. 9B). Bars and numbers indicate the size and location of the various fragments produced with a C-terminal hexahistidine tag and used in Cdk inhibition assays. The activity of these fragments is presented as a percentage relative to the activity of full length Kip1.

Figure 11A:
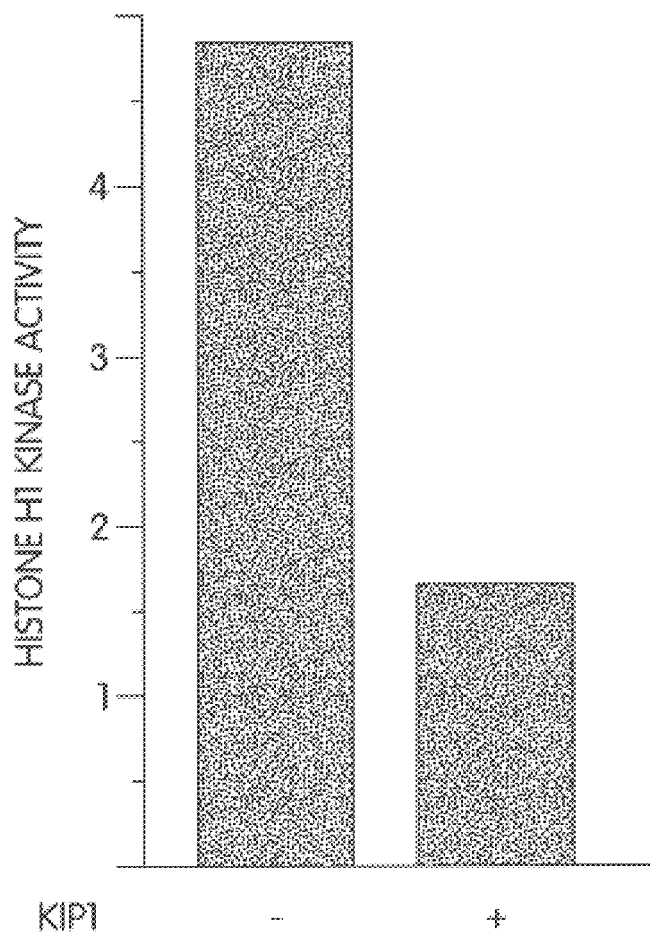
Figure 11B:
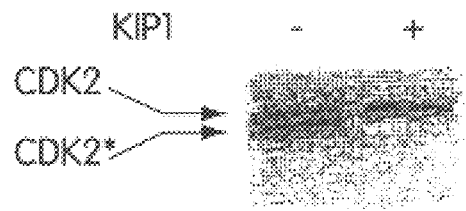

FIGS. 11A and 11B

Kip1 Inhibits Activation of Cdk2 in vitro

Extracts from exponentially growing A549 cells where incubated with baculovirally expressed histidine-tagged cyclin E alone or together with Kip1. Cyclin E complexes were then retrieved with $N^{++}$-NTA-agarose, and assayed for histone H1 kinase activity (A), and by western immunoblotting using anti-Cdk2 antibody (B). Kinase activity was quantitated by phosphorimager and expressed as arbitrary units. In B, Cdk2* indicates the faster migrating form of Cdk2 that corresponds to Cdk2 phosphorylated at $Thr^{160}$ (Gu Y. et al. (1992) *EMBO J.* 11:3995–4005).

Figure 12A:
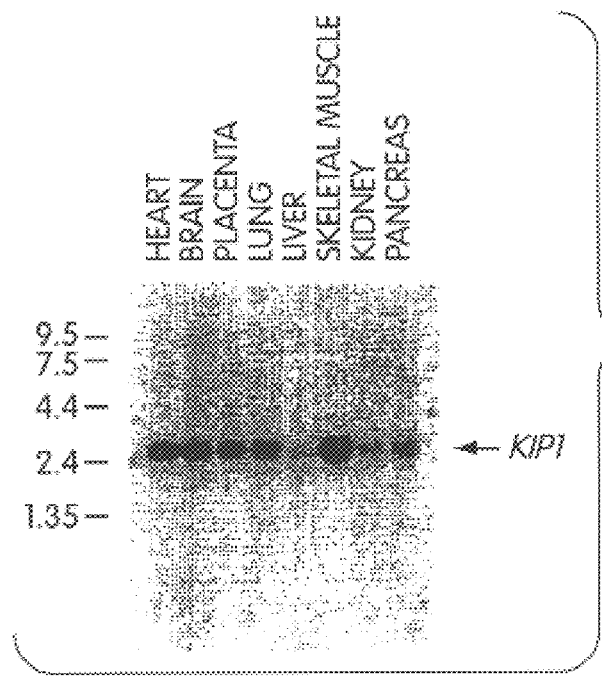
Figure 12B:
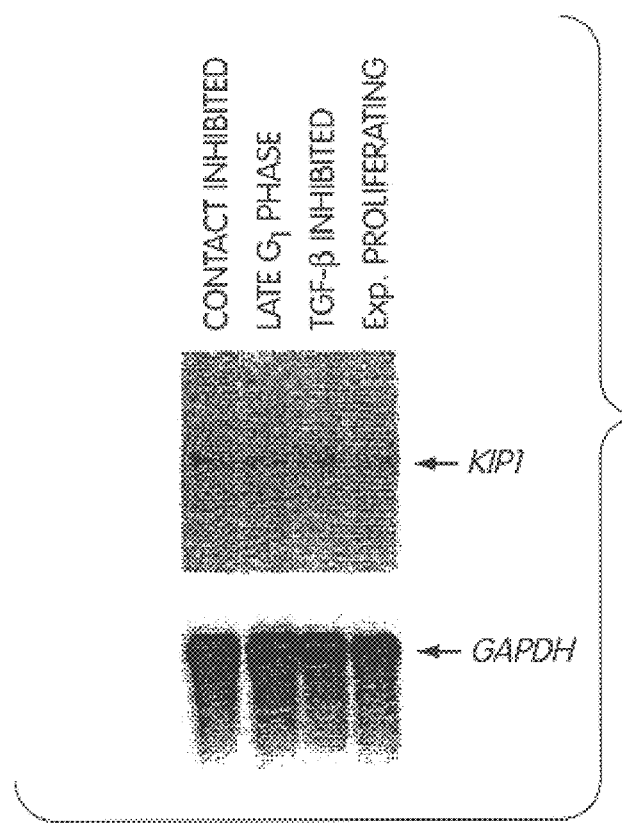

FIGS. 12A and 12B

Expression Pattern of Kip1 in Various Tissues and Cell Proliferation States

Kip1 Northern blots using equal amounts of poly(A)$^+$ RNA from the indicated human tissues (A) or from MvlLu cells in different proliferation states (B). The latter blot was rehybridized with a glyceraldehyde-phosphate dehydrogenase probe.

FIGS. 13A and 13B

A Partial Mink Kip1 cDNA (SEQ ID No. 5) and the Encoded Mink kip1 Protein (SEQ ID No. 6).

FIGS. 14A and 14B

Mouse Kip1 cDNA (SEQ ID No. 3) and the Encoded Mouse kip1 Protein (SEQ ID No. 4)

FIGS. 15A and 15B

Human Kip1 cDNA (SEQ ID No. 1) and the Encoded Human kip1 Protein (SEQ ID No. 2)

FIG. 16, Panels A–F

Kaplan-Meier plots: show the association of survival and expression of cyclin E and p27 in all women tested (a–c) and in node negative women (d–f). High levels of cyclin E were associated with decreased survival in the entire group of women tested (p=0.001) (Panel A) and in node negative women (p=0.003) (Panel D). Stratification of survival based on 3 levels of p27 immunostaining was possible in the entire group of tested patients and reflects the increasing mortality associated with low to absent p27 (p<0. 001) (Panel B. The association was also present in node negative women with low p27 (p=0.01) (Panel E) (the high and intermediate levels were included in the ÒhighÓ category for analysis). When cyclin E and p27 results were combined, stratification based on combinations of expression of the two proteins was possible in both groups of women (Panels C and F). Women with high cyclin E and low p27 expression experienced the highest mortality in the both groups (p<0.001).

FIG. 17

Table: of univariate and multivariate analyses comparing overall survival to prognostic factors in 246 breast cancer patients.

DETAILED DESCRIPTION OF THE INVENTION

The subject invention provides an isolated protein having an apparent molecular weight of about 27 kD as measured by SDS polyacrylamide gel electrophoresis, and capable of binding to and inhibiting the activation of a cyclin E-Cdk2 complex.

In the subject invention, the SDS polyacrylamide gel electrophoresis used to obtain the 27 kD molecular weight is performed under reducing conditions.

In one embodiment, the isolated protein of the subject invention is a mammalian protein. The mammalian protein may be a murine protein. The mammalian protein may also be a human protein. The mammalian protein may further be a mink protein. In one embodiment, the mink protein is the mink protein derived from MvlLu cells and having the partial internal amino acid sequences shown in Table I.

TABLE I

Partial Internal Amino Acid Sequences of
MvlLu Cell-Derived p27 Protein

| | | |
|---|---|---|
| 1. | Asn-Leu-Tyr-Pro-Leu-Thr-Asn-Tyr-Thr-Phe | (SEQ ID NO: 7) |
| 2. | Thr-Asp-Thr-Ala-Asp-Asn-Gln-Ala-Gly-Leu-Ala-Glu-Gln | (SEQ ID NO: 8) |
| 3. | Gln-Ala-Val-Pro-Leu-Met-Gly-Pro-Gln-Glu | (SEQ ID NO: 9) |
| 4. | Leu-Pro-Glu-Ohe-Tyr-Tyr-Arg-Pro-Pro-Arg-Pro-Pro | (SEQ ID NO: 10) |
| 5. | Tyr-Glu-Trp-Gln-Glu-Val | (SEQ ID NO: 11) |

In the subject invention, the protein having an apparent molecular weight of about 27 kD as measured by SDS polyacrylamide gel electrophoresis, and capable of binding to and inhibiting the activation of a cyclin E-Cdk2 complex, is referred to synonymously as "p27", "p27 protein", "inhibitor", "p27KiP1" and "Kip1".

As used herein, "isolated" means free of any other proteins. For example, the isolated protein may include nitrocellulose membrane fragments and a buffer.

As used herein, "capable of binding to a cyclin E-Cdk2 complex" means capable of binding to a cyclin E-Cdk2 complex but incapable of binding to Cdk2 alone.

Inhibition of the activation of a cyclin E-Cdk2 complex may be measured, for example, using assays for: (a) the site-specific phosphorylation of the Cdk2 moiety of the cyclin E-Cdk2 complex, and (b) histone kinase activity. Such assays are discussed in more detail infra. These assays may be conducted in a kinetic mode (i.e., by measuring the rate of phosphorylation) or as qualitative or quantitative static assays (i.e., measurements made at selected points in time). Those skilled in the art will know that a variety of enzymes and conditions may be used in such assays. In the subject invention, in a kinetic mode assay using equimolar amounts of p27 and cyclin E-Cdk2 complex, p27 inhibits the rate of site-specific phosphorylation of the Cdk2 moiety of the complex (as expressed in moles of Cdk2 moiety phosphorylated per minute) if the rate is inhibited by at least 50%.

The isolated 27 kD protein of the subject invention may be obtained, by way of example, by the heat treatment method and by the cyclin E-Cdk2 complex affinity method described infra.

The subject invention further provides a protein comprising a portion having amino acid sequence homology with the portion of p27 protein from amino acid residue +28 to, and including, amino acid residue +88 (as shown in FIG. 9B). In one embodiment, the protein has sequence identity with at least one boxed amino acid residue in the portion of p27 protein from amino acid residue +28 to, and including, amino acid residue +88 (as shown in FIG. 9B). The protein may be naturally occurring or recombinant. In one embodiment, the degree of homology is 30%. In another embodiment, the degree of homology is 40%. In another embodiment, the degree of homology is 44%. In another embodiment, the degree of homology is 50%. In another embodiment, the degree of homology is 90%.

The subject invention further provides recombinant nucleic acid molecules which encodes the proteins of the subject invention.

As used herein, a recombinant nucleic acid molecule is a nucleic acid molecule which does not occur in nature and which is obtained through the use of recombinant technology.

In one embodiment, the nucleic acid molecule is a DNA molecule. The DNA molecule may be a cDNA molecule or a cloned genomic DNA molecule. In a further embodiment, the cDNA is a mink kip1 cDNA. In a still further embodiment, the nucleotide sequence of mink kip1 cDNA is substantially the same as described in FIGS. 13A and 13B.

In a separate embodiment, the cDNA is a mouse kip1 cDNA. In a further embodiment, the nucleotide sequence of mouse kip1 cDNA is substantially the same as described in FIGS. 14A and 14B.

In a still separate embodiment, the cDNA is a human kip1 cDNA. In a further embodiment, the nucleotide sequence of human kip1 cDNA is substantially the same as described in FIGS. 15A and 15B.

In another embodiment, the nucleic acid molecule is an RNA molecule. The RNA molecule may be an mRNA molecule.

The subject invention further provides a vector comprising the recombinant nucleic acid molecule of the subject invention. In one embodiment, the vector is a plasmid. In another embodiment, the vector is a virus.

In a specific embodiment, a human kip1 cDNA with 2780 nucleotides containing 5' untranslated region, coding sequence and stop codon is cloned between KpnI and BamHI sites within the polylinker of the pCMV5 vector. This plasmid is designated pCMV5 p27kip1.

The pCMV5 p27kip1 was deposited on Jun. 7, 1995 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid pCMV5 p27kip1 was accorded ATCC accession number For the purpose of illustration only, applicants have isolated and characterized kip1 cDNA clones from human and mouse cDNA library using a mink kip1 cDNA. See infra. Similarly, other mammalian kip1 may be isolated using the known kip1 cDNAs disclosed in this invention. Briefly, the homologous genes may be cloned by using probe from the mink, mouse, or human kip1 cDNA by low stringency screening of the correspondent cDNA libraries.

In accordance with the invention, numerous vector systems for expression of the protein of the subject invention may be employed. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The marker may provide, for example, prototropy to an auxotrophic host, biocide resistance, (e.g., antibiotics) or resistance to heavy metals such as copper or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

The subject invention further provides a host vector system for the production of a protein having an apparent molecular weight of about 27 kD as measured by SDS polyacrylamide gel electrophoresis, and capable of binding to and inhibiting the activation of a cyclin E-Cdk2 complex, which comprises the vector of the subject invention in a suitable host.

In one embodiment, the suitable host is a bacterial cell. In another embodiment, the suitable host is an eucaryotic cell. The eucaryotic cell may be an insect cell. Insect cells include, for example, sf9 cells.

The subject invention further provides a method for producing a protein having an apparent molecular weight of about 27 kD as measured by SDS polyacrylamide gel electrophoresis, and capable of binding to and inhibiting the activation of a cyclin E-Cdk2 complex, which comprises growing the host vector system of the subject invention under conditions permitting the production of the protein and recovering the protein produced thereby.

Methods and conditions for growing host vector systems and for recovering the protein so produced are well known to those skilled in the art, and may be varied or optimized depending upon the specific vector and host cell employed. Such recovery methods include, for example, gel electrophoresis, ion exchange chromatography, affinity chromatography or combinations thereof.

The subject invention further provides a method of determining whether an agent is capable of specifically inhibiting the ability of p27 protein to inhibit the activation of cyclin E-Cdk2 complex which comprises: (a) contacting suitable amounts of p27 protein, cyclin E, Cdk2 and the agent under suitable conditions; (b) subjecting the p27, cyclin E, Cdk2, and agent so contacted to conditions which would permit the formation of active cyclin E-Cdk2 complex in the absence of p27 protein; (c) quantitatively determining the amount of active cyclin E-Cdk2 complex so formed; and (d) comparing the amount of active cyclin E-Cdk2 complex so formed with the amount of active cyclin E-Cdk2 complex formed in the absence of the agent, a greater amount of active cyclin E-Cdk2 complex formed in the presence of the agent than in the absence of the agent indicating that the agent is capable of specifically inhibiting the ability of p27 protein to inhibit the activation of cyclin E-Cdk2 complex.

As used herein, the term "agent" includes both protein and non-protein moieties. In one embodiment, the agent is a small molecule In another embodiment, the agent is a protein. The agent may be derived from a library of low molecular weight compounds or a library of extracts from plants or other organisms.

In the subject invention, an agent capable of specifically inhibiting the ability of p27 protein to inhibit the activation of cyclin E-Cdk2 complex interferes with the interaction between p27 protein and cyclin E-Cdk2 complex, but not with the site-specific phosphorylation of the Cdk2 moiety of the cyclin E-Cdk2 complex in the absence of p27 protein.

Cyclin E may be obtained using methods well known to those skilled in the art based on the nucleic acid sequence encoding same as disclosed in Koff, et al. (1991). Cdk2 may be obtained using methods well known to those skilled in the art based on the nucleic acid sequence encoding same as disclosed in Elledge and Spottswood (1991, supra).

Amounts of p27 protein, cyclin E, Cdk2 and the agent suitable for the method of the subject invention may be determined by methods well known to those skilled in the art. An example of suitable conditions (i.e., conditions suitable for measuring the effect on p27 function by an agent) under which p27 protein, cyclin E, Cdk2 and the agent are contacted appears infra.

An example of conditions which would permit the formation of active cyclin E-Cdk2 complex in the absence of p27 protein also appears infra.

As used herein, "active cyclin E-Cdk2 complex" means a cyclin E-Cdk2 complex which is capable of specifically phosphorylating a suitable substrate (e.g., histone H1). An example of an active cyclin E-Cdk2 complex is provided infra. The amount of active cyclin E-Cdk2 complex correlates with its measurable activity. Thus, quantitatively determining the amount of active cyclin E-Cdk2 complex may be accomplished by measuring the rate at which a substrate of the active cyclin E-Cdk2 complex is phosphorylated. Such methods well known to those skilled in the art, and include, for example, a histone H1 kinase assay.

In the method of the subject invention, the cyclin E and Cdk2 proteins may exist as separate proteins, or as a complex, prior to being contacted with the agent.

The subject invention further provides a method of determining whether an agent is capable of specifically enhancing the ability of p27 protein to inhibit the activation of cyclin E-Cdk2 complex which comprises: (a) contacting suitable amounts of p27 protein, cyclin E, Cdk2 and the agent under suitable conditions; (b) subjecting the p27 protein, cyclin E, Cdk2, and agent so contacted to conditions which would permit the formation of active cyclin E-Cdk2 complex in the absence of p27 protein; (c) quantitatively determining the amount of active cyclin E-Cdk2 complex so formed; and (d) comparing the amount of active cyclin E-Cdk2 complex so formed with the amount of active cyclin E-Cdk2 complex formed in the absence of the agent, a lesser amount of active cyclin E-Cdk2 complex formed in the presence of the agent than in the absence of the agent indicating that the agent is capable of specifically enhancing the ability of p27 protein to inhibit the activation of cyclin E-Cdk2 complex.

In the subject invention, an agent capable of specifically enhancing the ability of p27 protein to inhibit the activation of cyclin E-Cdk2 complex affects the interaction between p27 protein and cyclin E-Cdk2 complex, but not with the site-specific phosphorylation of the Cdk2 moiety of the cyclin E-Cdk2 complex in the absence of p27 protein.

The subject invention further provides a method of determining whether an agent is capable of mimicking the ability of p27 protein to inhibit the activation of cyclin E-Cdk2 complex which comprises: (a) contacting suitable amounts of cyclin E, Cdk2 and the agent under conditions which would permit the formation of active cyclin E-Cdk2 complex in the absence of the agent; (b) quantitatively determining the amount of active cyclin E-Cdk2 complex so formed; and (c) comparing the amount of active cyclin E-Cdk2 complex so formed with the amount of active cyclin E-Cdk2 complex formed in the absence of the agent, a lesser amount of active cyclin E-Cdk2 complex formed in the presence of the agent than in the absence of the agent indicating that the agent is capable of mimicking the ability of p27 protein to inhibit the activation of cyclin E-Cdk2 complex.

The subject invention further provides a method of treating a subject having a hyperproliferative disorder which comprises administering to the subject a therapeutically effective amount of an agent capable of specifically enhancing the ability of p27 protein to inhibit the activation of cyclin E-Cdk2 complex in the hyperproliferative cells of the subject, so as to thereby treat the subject.

In the preferred embodiment, the subject is a human.

A hyperproliferative disorder is a disorder wherein cells present in the subject having the disorder proliferate at an abnormally high rate, which abnormally high rate of proliferation is a cause of the disorder. In one embodiment, the hyperproliferative disorder is selected from the group consisting of cancer and hyperplasia.

The administering of the agent may be effected or performed using any of the various methods known to those skilled in the art. In one embodiment, the administering comprises administering intravenously. In another embodiment, the administering comprises administering intramuscularly. In yet another embodiment, the administering comprises administering subcutaneously.

The therapeutically effective amount of the agent may be determined by methods well known to those skilled in the art.

The subject invention further provides a pharmaceutical composition comprising a therapeutically effective amount of an agent capable of specifically enhancing the ability of p27 protein to inhibit the activation of cyclin E-Cdk2 complex in the hyperproliferative cells of a subject suffering from a hyperproliferative disorder, and a pharmaceutically acceptable carrier.

Pharmaceutically acceptable carriers are well known to those skilled in the art and include, but are not limited to, 0.01–0.1 M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, such as those based on Ringer's dextrose, and the like. Preservatives and other additives may also be present, for example, antimicrobials, antioxidants, chelating agents, inert gases and the like.

The subject invention further provides a method of treating a subject having a hyperproliferative disorder which comprises administering to the subject a therapeutically effective amount of an agent capable of mimicking the ability of p27 protein to inhibit the activation of cyclin E-Cdk2 complex in the hyperproliferative cells of the subject, to thereby treat the subject.

The subject invention further provides a method of treating a subject having a hypoproliferative disorder which comprises administering to the subject a therapeutically effective amount of an agent capable of specifically inhibiting the ability of p27 protein to inhibit the activation of cyclin E-Cdk2 complex in the hypoproliferative cells of the subject, to thereby treat the subject.

In the preferred embodiment, the subject is a human.

A hypoproliferative disorder is a disorder wherein cells present in the subject having the disorder proliferate at an abnormally low rate, which abnormally low rate of proliferation is a cause of the disorder. In one embodiment, the hypoproliferative disorder is an ulcer. Examples of hypoproliferative cells are terminally differentiated cells in normal tissue and organs which, with the exception of the liver and bone marrow, normally lack the ability to regenerate following traumatic injury. Thus, the method of the subject invention, and agents identified thereby, have use in stimulating tissue and organ repair in subjects in need thereof, as well as in establishing tissue cultures of cells from a variety of different tissues.

The therapeutically effective amount of the agent may be determined by methods well known to those skilled in the art.

The subject invention further provides a pharmaceutical composition comprising a therapeutically effective amount of an agent capable of specifically inhibiting the ability of p27 protein to inhibit the activation of cyclin E-Cdk2 complex in the hypoproliferative cells of a subject suffering from a hypoproliferative disorder, and a pharmaceutically acceptable carrier.

The subject invention further provides a method for obtaining partially purified polyclonal antibodies capable of specifically binding to p27 protein which method comprises (a) immunizing a subject with p27 protein, (b) recovering from the immunized subject serum comprising antibodies capable of specifically binding to p27 protein, and (c) partially purifying the antibodies present in the serum, thereby obtaining partially purified polyclonal antibodies capable of specifically binding to p27 protein.

As used herein, partially purified antibodies means a composition which comprises antibodies which specifically bind to p27 protein, and consists of fewer protein impurities than does the serum from which the antibodies are derived. A protein impurity means a protein other than the antibodies specific for p27 protein. For example, the partially purified antibodies might be an IgG preparation.

Methods of recovering serum from a subject are well known to those skilled in the art. Methods of partially purifying antibodies are also well known to those skilled in the art, and include, for example, filtration ion exchange chromatography, and precipitation.

The subject invention further provides the partially purified antibodies produced by the method of the subject invention.

The subject invention further provides a method for obtaining a purified monoclonal antibody capable of specifically binding to p27 protein which method comprises (a) immunizing a subject with p27 protein, (b) recovering from the immunized subject a B cell-containing cell sample, (c) contacting the B cell-containing cell sample so recovered with myeloma cells under conditions permitting fusion of the myeloma cells with the B cells therein so as to form hybridoma cells, (d) isolating from the resulting sample a hybridoma cell capable of producing a monoclonal antibody capable of specifically binding to p27 protein, (e) growing the hybridoma cell so isolated under conditions permitting the production of the monoclonal antibody, and (f) recovering the monoclonal antibody so produced, thereby obtaining a purified monoclonal antibody capable of specifically binding to p27 protein. Methods of making hybridomas and monoclonal antibodies are well known to those skilled in the art.

The subject invention further provides the hybridoma cell produced in step (d) of the method of the subject invention.

The subject invention further provides the purified monoclonal antibody produced by the method of the subject invention.

As used herein, a "purified monoclonal antibody" means the monoclonal antibody free of any other antibodies.

The subject invention further provides an antibody capable of specifically binding to p27 protein, said antibody being labeled with a detectable marker. The label group can be selected, e.g., from a group consisting of radioisotopes, fluorescent compounds, enzymes, and enzyme co-factors.

The labeled antibody may be a polyclonal or monoclonal antibody. In one embodiment, the labeled antibody is a purified labeled antibody. The term "antibody" includes, for example, both naturally occurring and non-naturally occurring antibodies. Specifically, the term "antibody" includes polyclonal and monoclonal antibodies, and fragments thereof Furthermore, the term "antibody" includes chimeric antibodies and wholly synthetic antibodies, and fragments thereof The detectable marker may be, for example, radioactive or fluorescent. Methods of labeling antibodies are well known in the art.

Antibody fragments which contain the idiotype of a p27 antigen can be generated by known techniques. For example, such fragments include, but are not limited to: the $F(ab')_2$ fragments generated by pepsin digestion of the antibody molecule and the Fab fragments which can be generated by reducing disulfide bridges of the $F(ab')_2$ fragments.

One skilled in the art will appreciate that the invention also encompasses the use of antigen recognizing immunoglobulin fragments. Such immunoglobulin fragments include, for example, the Fab', $F(ab')_2$, Fv or Fab fragments, or other antigen recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing immunoglobulin fragments are well known to those skilled in the art.

In addition, the immunoglobulin may be a single chain antibody ("SCA"). These can consist of single chain Fv fragments ("scFv") in which the variable light ("V[L]") and variable heavy ("V[H]") domains are linked by a peptide bridge or by disulfide bonds. Also, the immunoglobulin may consist of single V[H] domains (dAbs) which possess antigen-binding activity. See, e.g., Winter and Milstein, (1991) *Nature* 349:295; and Glockshaber et al., (1990) *Biochemistry* 29:1362.

Synthetic antibodies, e.g., generated by combinatorial mutagenesis and phage display, are equivalents of antibodies generated by immunization.

The subject invention further provides a method for quantitatively determining the amount of p27 protein in a sample which comprises contacting the sample with the antibody of the subject invention under conditions permitting the antibody to form a complex with p27 protein present in the sample, quantitatively determining the amount of complex so formed, and comparing the amount so determined with a known standard, so as to thereby quantitatively determine the amount of p27 protein in the sample.

The sample may be, for example, a cell sample, tissue sample, or protein-containing fluid sample. Conditions permitting an antibody to form a complex with its antigen and methods of detecting the presence of complex so formed are well known in the art.

The amount of p27 protein present in a sample as determined need not be an absolute number, in the sense that it need not be the actual number of p27 protein molecules or moles of p27 protein in the sample. Rather, the amount determined may merely correlate with this number.

The subject invention further provides a method for quantitatively determining the level of expression of p27 in a cell population, and a method for determining whether an agent is capable of increasing or decreasing the level of expression of p27 in a cell population. The method for determining whether an agent is capable of increasing or decreasing the level of expression of p27 in a cell population comprises the steps of (a) preparing cell extracts from control and agent-treated cell populations, (b) isolating p27 from the cell extracts (e.g., by affinity chromatography on, and elusion from, a cyclin E-Cdk2 complex solid phase affinity adsorbent), (c) quantifying (e.g., in parallel) the amount of p27 inhibitor activity in the control and agent-treated cell extracts using a cyclin E-Cdk2 kinase assay (e.g., histone H1 assay described infra). Agents that induce increased p27 expression may be identified by their ability to increase the amount of p27 inhibitor activity in the treated cell extract in a manner that is dependent on transcription, i.e., the increase in p27 inhibitor activity is prevented when cells are also treated with an inhibitor of transcription (e.g., actinomycin D). In a similar manner, agents that decrease expression of p27 may be identified by their ability to decrease the amount of p27 inhibitor activity in the treated cell extract in a manner that is dependent upon transcription.

The subject invention further provides a method of determining whether a cell sample obtained from a subject possesses an abnormal amount of p27 protein which comprises (a) obtaining a cell sample from the subject, (b) quantitatively determining the amount of p27 protein in the sample so obtained, and (c) comparing the amount of p27 protein so determined with a known standard, so as to thereby determine whether the cell sample obtained from the subject possesses an abnormal amount of p27 protein.

The subject invention further provides a method of determining whether the amount of p27 protein in a cell sample obtained from a subject having a disease is correlative with the disease which comprises determining whether a cell sample obtained from the subject possesses an abnormal amount of p27 protein, an abnormal amount of p27 protein in the sample indicating that the amount of p27 protein in the cell sample obtained from the subject having the disease is correlative with the disease.

The subject invention further provides a method of quantitatively determining the specific activity of p27 protein in a sample which comprises quantitatively determining (i) the ability of the p27 protein in the sample to inhibit the activation of cyclin E-Cdk2 complex and (ii) the total amount of p27 protein in the sample, and dividing the ability of the p27 protein so determined by the total amount of p27 protein so determined so as to thereby quantitatively determine the specific activity of p27 protein in the sample.

The subject invention further provides a kit for practicing the methods of the subject invention. In one embodiment, the kit comprises suitable amounts of p27 protein, cyclin E and Cdk2. The kit may further comprise suitable buffers, and a package insert describing p27 as an inhibitor of cyclin E-Cdk2 complex activity.

In one embodiment, the subject invention provides a method of diagnosing a hyperproliferative disorder in a subject which disorder is associated with the presence of a p27 protein mutation in the cells of the subject, which comprises determining the presence of a p27 protein mutation in the cells of the subject, said mutation being associated with a hyperproliferative disorder, so as to thereby diagnose a hyperproliferative disorder in the subject.

As used herein, "diagnosing" means determining the presence of a hyperproliferative disorder in a subject. In one embodiment, "diagnosing" additionally means determining the type of hyperproliferative disorder in a subject.

As used herein, a "p27 protein mutation" may be any abnormality in the primary sequence of p27 protein resulting from an abnormality in the genomic DNA sequence encoding same or controlling the expression of same. For example, the p27 protein mutation may be a point mutation, a deletion mutation of a portion of p27 protein, or an absence of the entire p27 protein resulting from an abnormality in the structural gene encoding same or regulatory DNA sequence controlling the expression of same.

Determining the presence of a p27 protein mutation may be accomplished according to methods well known to those skilled in the art. Such methods include probing a subject's DNA or RNA with a p27 nucleic acid probe. Such methods also include analyzing a protein sample from the subject for p27 protein structural abnormalities or functional abnormalities resulting therefrom.

In the preferred embodiment, the subject is a human and the hyperproliferative disorder is cancer.

In another embodiment, the method can be used to determine the amount of p27 protein present in a cell, which in turn can be correlated with progression of a hyperproliferative disorder. The level of p27 protein can be used predictively to evaluate whether a sample of cells contains cells which are, or are predisposed towards becoming, transformed cells. Moreover, the subject method can be used to assess the phenotype of cells which are known to be transformed, the phenotyping results being useful in planning a particular therapeutic regimen. For instance, as the appended examples suggest, absence or low levels of p27 protein in sample cells is a powerful diagnostic and prognostic marker for a cancerous diseases. The observation of p27 protein level can be utilized in decisions regarding, e.g., the use of more aggressive therapies.

Prognosis in clinical cancer is an area of great concern and interest. It is important to know the aggressiveness of the malignant cells and the likelihood of tumor recurrence in order to plan the most effective therapy. Breast cancer, for example, is managed by several alternative strategies. In some cases local-regional and systemic radiation therapy is utilized while in other cases mastectomy and chemotherapy or mastectomy and radiation therapy are employed. As known in the art, treatment decisions for individual breast cancer patients can be based on, for example, the number of axillary lymph nodes involved with disease, estrogen receptor and progesterone receptor status, the size of the primary tumor, and stage of disease at diagnosis. It has also been reported that DNA aneuploidy and proliferative rate (percent S-phase) can help in predicting the course of disease (Dressler et al., (1988) *Cancer* 61:420; and Clark et al., (1989) *N. Engl. J. Med.* 320:627). The subject method provides a means for accurately predicting the course of disease for breast cancer patients. The ability to detect destabilization of the p27 protein can facilitate separation of patients with good prognosis, e.g., who will need little to no further therapy, from those more likely to recur who might benefit from more intensive treatments. This index can be combined with other prognostic methods.

This is particularly true in the case of breast cancer which has not progressed to the axillary lymph nodes. There is now evidence in prospective randomized clinical trials that adjuvant endocrine therapy and adjuvant chemotherapy beginning immediately after surgical removal of the primary breast tumor can be of benefit in some of these node-negative patients. This has led to recommendations in the art that most if not all node-negative breast cancer patients should be considered for some form of adjuvant therapy. But since the majority (approximately equal to 70%) of these patients enjoy long-term survival following surgery and/or radiotherapy without further treatment, it may be inappropriate to recommend adjuvant therapy for all of these patients. As described in the appended examples, the subject method can be used to distinguish those node-negative patients on the basis of significantly elevated or reduced risk of mortality, and suggests that this index may be useful in determining which patients would benefit from, e.g., continued and/or more aggressive therapy.

Moreover, it be appreciated that the subject method provides a general procedure for predicting tumor recurrence in cancer patients in general once the primary tumor is detected. The present invention is a significant step in the ability to predict with some confidence the likelihood of cancer recurrence. It is clear from the extensive studies on the p27 protein that it has an important physiological role, but until now no one has been able to relate its cellular levels or presence to clinical manifestations of dysfunction. Now the survival risk to cancer patients can be better assessed and aggressive therapies applied as indicated to those in high risk groups.

The term "prognosis" is art recognized and, as set out above, concerns the likelihood that an individual may suffer occurrence, relapse or distant relapse of cancerous disease. Relapse is the recurrence of tumor growth due to propagation of tumor cells remaining in the host after treatment, new tumor cell development, or the like. Distant relapse concerns tumor dissemination such that tumor growth occurs at a site distant from the site of the original tumor. Of additional interest in the case of disease relapse is the length of the relapse-free survival time. Relapse-free survival time is the period between either surgical removal of the tumor or the suppression or mitigation of tumor growth and the recurrence of cancerous disease. Prognosis may be affected by various criteria such as histological type, tumor grade, tumor size, ploidy, and expression of certain hormone receptors such as estrogen receptor. These criteria provide some guidance in determining the need for and efficacy of subjecting the patient to various cancer therapies, such as irradiation, adjuvant therapy or surgical procedures such as mastectomy in the case of breast cancer.

To further illustrate, the appended examples describe that levels of p27 protein, but not levels of p27 mRNA, are decreased in a variety of different tumor cells. For example, we undertook an immunohistochemical analysis of p27 protein levels in breast ductal carcinomas, and found that low levels of p27 (p=0.01) were strongly predictive of increased mortality, both before and after adjustment for other clinical and pathological characteristics. Distant relapse-free survival, which is defined as survival without formation of tumors distant from the original site, is significantly inversely correlated with the combined analysis of the percent of p27 minus tumor cells. This enabled us to subdivide women with localized, node-negative disease into groups with either significantly elevated or reduced risk of mortality, and suggested that this indix may be useful in determining which patients would benefit from more aggressive therapy.

The subject method is applicable to the diagnosis/prognosis of such breast cancer types as ductal, mucinous, lobular and the like. The cancer may be detected at any stage of tumor development, including hyperplasia, in situ and the like. The subject invention finds particular application for diagnosis where the patient carries an axillary lymph-node negative, ductal carcinoma of the breast.

Detection of p27 stability may serve as a marker for the presence of cancerous cells and also allow for determination of the prognosis of the patient carrying the tumor. The subject method can be used to augment the detection and/or prognosis of such solid tumors as, for example, carcinomas (particularly epithelial-derived carcinomas) of such tissues as ovaries, lung, intestinal, pancreas, prostate, testis, liver, skin, stomach, renal, cervical, colorectal, and head and neck; melanomas; and sarcomas such as Kaposi's sarcoma and rhabdomyosarcoma. In preferred embodiments, the subject method is used to assess a malignant or pre-malignant epithelial carcinoma.

The diagnostic methods of the subject invention may also be employed as follow-up to treatment, e.g., quantitation of the level of p27 protein may be indicative of the effectiveness of current or previously employed cancer therapies as well as the effect of these therapies upon patient prognosis.

Accordingly, the present invention makes available diagnostic assays and reagents for detecting loss of p27 protein from a cell in order to aid in the diagnosis and phenotyping of proliferative disorders arising from, for example, tumorigenic transformation of cells, or other hyperplastic or neoplastic transformation processes, as well as differentiative disorders, such as degeneration of tissue, e.g. neurodegeneration.

While not wishing to be bound by any particular theory, the inventors understand that the inactivation of the p27 protein can occur by post-transcriptional modification through a mechanism whereby degradation of p27 increased, e.g., such as may be caused by deregulation of a ubiquitin-proteosome pathway involving p27. As set forth in Pagano et al. (1995) Science 269:682, the p27 protein is an apparent substrate for ubiquitin-mediated proteolysis. According to this understanding, the rate of degradation of the p27 protein can be increased in particular cells, e.g., the protein is destablized, leading to a net loss of p27 protein in the cytoplasm/nucleus of those cells. The loss of this mitotic inhibitor can in turn promote aberrant proliferation or dedifferentiation of the afflicted cell.

By the present method, there is provided a method for evaluating an individual's risk (e.g., likelihood) of having or developing a disorder marked by abberant proliferation or dedifferentiation. The method can also be used prognostically. Where such disorders have already been diagnosed, the present method, by facilitating careful phenotyping of transformed cells, can improve the choice of intervention strategies by clinicians. For instance, the aggressiveness of the therapy to be used may be influenced by the knowledge of whether loss of regulation of proliferation or differentiation is caused by destabilization of a p27 protein, or other genetic abnormality.

The phrase "aberrant modification or mutation" of a gene refers to such genetic lesions as, for example, deletion, substitution or addition of nucleotides to a gene, as well as non-wild type splicing of mRNA transcribed from the gene. Mis-expression of a gene, on the other hand, refers to aberrant levels of transcription of the gene relative to those levels in a normal cell under similar conditions.

The term "aberrant proliferation" refers to proliferation of cells which is undesired, e.g., such as may arise it due to transformation and/or immortalization of the cells, e.g., neoplastic or hyperplastic, for purposes of wound healing, cosemetic, etc.

The term "aberrant dedifferentiation" refers to loss of differentiation of cells of a tissue such that the afflicted tissue losses at least a portion of the normal phenotype and function for animal at that development stage. For example, adult tissue undergoing aberrant dedifferentiation will be characterized by loss of at least a portion of the functional performance of that tissue in an adult organism.

The term "aberrant apoptosis" refers to unwanted cell death caused by apoptosis, e.g., as may occur in a variety of degenerative disorders, including such neurodegenerative disorders as Alzheimer's disease and Parkinson's disease.

The term "patient" refers to an animal, preferably a mammal, including humans as well as livestock and other veterinary subjects.

The terms "reduced", "destabilized", "decreased" or the like, e.g., which denote quantitative differences between two states, refer to at least statistically significant differences between the two states. For example, "assessing whether the p27 protein is destabilized in the test cells" means that the level of p27 protein in the test cells is lower by at least a statistically significant amount when compared to a normal cell. Such terms are also applied herein to, for example, rates of cell proliferation, levels of expression, and the like.

The term "p27-minus" refers to a cell phenotype wherein the cell possess a reduced cellular amount of the p27 protein relative to a normal cell of similar tissue origin. For example, a p27-minus cell may have less than 50%, 25%, 10%, or 5% of the p27 that a normal control cell, As set out above, one aspect of the present invention relates to diagnostic assays for determining, in the context of cells isolated from a patient, if the level of a p27 protein is significantly reduced in the sample cells. In particular, the assay evaluates the level of p27 protein in the test cells, and, preferably, compares the measured level with p27 levels detected in at least one control cell, e.g., a normal cell and/or a transformed cell of known phenotype. In general, the assay of the instant application detects destabilization of the p27 protein which decreases the level of protein in the cell, particularly in the nucleus.

In preferred embodiments, the method can be generally characterized as including a step of detecting, in a sample of cells from the subject, the presence (level of) or absence of a p27 protein. As will be understood by those skilled in the art, the method of the present invention can be carried out using any of a large number of assay techniques for detecting destabilization of p27 protein, and importantly, provides the ability to discern between different molecular causes underlying aberrant cell growth, proliferation and/or differentiation.

Of particular importance to the subject invention is the ability to quantitate the level of p27 protein as determined by the number of cells associated with a normal or abnormal p27 level. The number of cells with a particular p27 phenotype may then be correlated with patient prognosis. In one embodiment of the invention, the p27 phenotype of the lesion is determined as a percentage of cells in a biopsy which are found to have abnormally low levels of p27 protein. Such expression may be detected by immunohistochemical assays, dot-blot assays, ELISA and the like. In general, it will be important that a significant number of cells in a section be examined, since tumors with only a small fraction of p27-minus cells could otherwise be scored p27 positive. For instance, a significant number of examined cells may comprise at least all the cells contained within 3 to 6 fields of a tissue sample observed at a magnification of 100×. As the number of cells examined in a tissue sample increases, the confidence one may have in classifying a sample as p27-minus increases.

To further illustrate, the presence of the p27 protein in a sample of cells can be determined by immunoassays or histochemical staining employing antibodies reactive with the p27 protein, e.g., antibodies specifically reactive with the p27 protein of SEQ ID. No. 2. Antibodies can be prepared conventionally (as described below) employing, e.g., the human p27 protein or antigenic fragments thereof, as the immunogen. For example, isolated p27 protein can be generated according to the methods described above. Human p27 is not required, and antibodies raised against p27 from other vertebrates can be cross-reactive with the human protein.

Immunoassays are commonly used to quantitate the levels of proteins in cell samples, and many other immunoassay techniques are known in the art. The invention is not limited to a particular assay procedure, and therefore is intended to include both homogeneous and heterogeneous procedures. Exemplary immunoassays which can be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the anti-p27 antibody and is selected so as to meet the needs of various users of the method which are often dictated by the availability of assay equipment and compatible immunoassay procedures. General techniques to be used in performing the various immunoassays noted above are known to those of ordinary skill in the art.

Where tissue samples are employed, immunohistochemical staining may be used to determine the number of cells having the p27-minus phenotype. For such staining, a multi-block of tissue is taken from the biopsy or other tissue sample and subjected to proteolytic hydrolysis, employing such agents as protease K or pepsin. In certain embodiments, it may be desirable to isolate a nuclear fraction from the sample cells and detect the level of p27 in the nuclear fraction.

The tissue samples are fixed by treatment with a reagent such as formalin, gluteraldehyde, methanol, or the like. The samples are then incubated with an antibody, preferably a monoclonal antibody, with binding specificity for p27. This antibody may be conjugated to a label for subsequent detection of binding. Samples are incubated for a time sufficient for formation of complexes comprising p27 antigen and p27-specific antibody. Binding of the anti-p27 antibody is then detected by virtue of a label conjugated to this antibody. Where the anti-p27 antibody is unlabeled, a second labeled antibody may be employed, e.g., which is specific for the isotype of the anti-p27 antibody. Examples of labels which may be employed include radionuclides, fluorescers, chemiluminescers, enzymes and the like.

Where enzymes are employed, the substrate for the enzyme may be added to the samples to provide a colored or fluorescent product. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

In one embodiment, the assay is performed as a dot blot assay. The dot blot assay finds particular application where tissue samples are employed as it allows determination of the average amount of p27 associated with a single cell by correlating the amount of p27 in a cell-free extract produced from a predetermined number of cells.

To achieve this, a single-cell suspension is produced from tissue sample taken from a patient, and the number of cells in each sample is determined. Tissues or cells which express p27, preferably tissues or cells which express a known amount of p27, may serve as a positive control and additionally may serve as a standard for comparison of results with test samples. Tissues or cells which lack p27 may be employed as a negative control.

It is well known in the art that single-cell suspensions may be produced from tissue in a variety of ways (e.g. incubation with EDTA in PBS, trypsin digestion, etc.). The number of cells in each sample may be determined by various conventional means, e.g. by Trypan blue or eosin staining. Cell-free extracts may be prepared from the single-cell suspensions by extraction with a detergent, such as Triton X-100, sonication or other conventional means known in the art. To provide for precise quantitative results, the protein concentration of each cell-free extract may be determined by methods known in the art and dilutions from each extract employed in the assay.

Each sample may than be bound to a soluble support, such as nitrocellulose or the well of a microtiter plate. Following washing to remove unbound material, areas of the support which are not bound to extract components may be blocked by incubation with a blocking agent such as PBS containing bovine serum albumin (BSA) to reduce non-specific binding of subsequent reagents to the support. The samples may then be washed and subsequently incubated with an anti-p27 antibody, such as a monoclonal antibody, to allow for formation of complexes of p27 and the p27-specific antibody. Binding of the antibody may be detected and analyzed as described above. The amount of p27 detected may be correlated with the number of cells in the original sample to determine the average amount of p27 protein per cell. The average amount of p27 protein per cell in the test sample may then be compared to the average amount of p27 protein per cell in standard samples and patient diagnosis/prognosis determined.

Still another exemplary embodiment of an immunoassay which can be adapted for detection of p27 protein levels is described in U.S. Pat. No. 4,499,183. Briefly, the '183 patent describes a immnunoassay method in which the sample cells are contacted with a hypotonic solution carefully adjusted to swell the cells but not to result in substantial lysis prior to the completion of the assay, e.g., specifically the detection step. Swelling the cells results in an expanded cell size and larger cell membrane channels for facilitating antibody uptake. Thereafter, the cell membrane is rigidized and water is removed by standard fixation techniques. The cell is preferably first hydrated and then under appropriate conditions, reacted with a solution containing antibodies specific for the p27 protein. The antibody is advantageously labeled with a detectable label such as with a fluorochrome, metal particle, radioisotope or enzyme, or alternatively can be detected by an indirect immunofluorescence technique. The latter is accomplished by subsequent reaction of the cells previously reacted with the first antibody, with a second antibody specific for the first antibody. The second antibody is ideally labeled with a detectable label as above. Those antibodies not attached either directly or indirectly (i.e., by attachment through another antibody in turn attached to the antigen or antibody) to the intracellular p27 protein are removed by a washing process and the remaining cells analyzed for the presence of label. Detection of the label is in turn related to the presence of the intracellular p27 protein.

An ideal reagent kit in accordance with this discovery would therefore comprise a swelling solution, as well as antibody specific for p27 to be detected, second antibody with a label such as fluorescein isothiocyanate (FITC) specific for the first antibody and various controls and washing buffers. Such cells can be FACS sorted. In preferred embodiments, another antibody for a cell marker is provided as a means for identifying the general population of cells in which a p27 minus phenotype is to detected.

It will be understood that other p27-binding molecules can be equivalently used in place of an antibody. For instance, CDK proteins can be used to detect/quantitate p27 protein.

In other embodiments, the level of p27 protein can be detected in cell lysates by chromatography or gel electrophoresis.

In yet another embodiment, the rate of degradation of p27 can be assessed in the sample cells. For instance, labeled p27 protein can be added to lysate from the sample cells and the rate of degradation monitored, e.g., by detecting fragments of the labeled protein or, alternatively, detecting ubiquitination of the ectopic p27. Likewise, proteolysis inhibitors can be added to the cells or cell lysates, and the rate of appearance of ubiquitination products of a heterologous or endogenous p27 protein can be detected. In each instance, the rate is compared to rates determined for control cells, e.g., cells of a known p27 phenotype.

Used in conjunction with detection of p27 protein, the detection of p27 transcript in the cell sample can facilitate the determination of the molecular basis for loss of p27 protein in a cell sample, e.g., to distinguish reduced transcription or translation from protein destabilization. Accordingly, the subject method may include a further step of determining the level of p27 mRNA in a sample of cells, e.g., by using a probe which hybridizes under stringent conditions to the p27 nucleic acid of SEQ ID No. 1.

In certain embodiments, other antigens expressed by tumor cells may be detected, e.g., to determine the percentage of p27-minus cells in a given sub-population of cells from a sample. Tumor antigens of interest include breast carcinoma; prostate specific antigen (PSA); carcinoembryonic antigen (CEA); alpha-fetoprotein (AFP); CA125 antigen; soluble IL-2 receptor, progesterone receptor; estrogen receptor, and the like. The tumor-associated antigen CA-242 is expressed in the vast majority of colorectal tumors and is only weakly expressed or absent in normal colonic tissue. Other antibodies, against tumor cell markers associated with specific tumor types, which may be used in accordance with the method of the present invention include but are not limited to HEA125 MAb, HT29-15 Mab (colorectal carcinoma); BCD-B4 MAb or NCRC-11 Mab (breast carcinoma); anti-PSA antibody or PD41 Mab (prostate carcinoma); ALT-04 Mab (lung carcinoma); B72.3 MAb, HMD4 MAb or COC183B2 (ovarian carcinoma); HEA-125 MAb, MM46 MAb, or 9.2.27 Mab (melanomas); MGb 2 MAb, or ZCE 025 Mab (gastric carcinoma); BW494 Mab (pancreatic carcinoma); CEB9 Mab (uterine cervical carcinoma); HSAN 1.2 Mab (neuroblastoma); HISL-19 Mab (neuroendocrinomas); TRA-1-60 Mab (seminoma).

The subject invention further provides a pharmaceutical composition which comprises an effective amount of a recombinant virus capable of infecting a suitable host cell, said recombinant virus comprising the nucleic acid molecule of the subject invention, and a pharmaceutically acceptable carrier.

The "suitable host cell" is any cell in which p27 protein would normally be produced in a healthy subject.

Pharmaceutically acceptable carriers are well known to those skilled in the art and include, but are not limited to, 0.01–0.1 M and prefereably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol,. polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, such as those based on Ringer's dextrose, and the like. Preservatives and other additives may also be present, such antimicrobials, antioxidants, chelating agents, inert gases and the like.

Finally, this invention provides a method for treating a subject suffering from a hyperproliferative disorder associated with the presence of p27 protein mutation in the cells of the subject, which comprises administering to the subject an amount of the pharmaceutical composition of the subject invention effective to treat the subject.

In the preferred embodiment, the subject is a human and the hyperproliferative disorder is cancer.

In order to facilitate an understanding of the Experimental Details section which follows, certain frequently occurring methods and/or terms are best described in Sambrook, et al. (1989).

This invention will be better understood by reference to the Experimental Details which follow, but those skilled in the art will readily appreciate that the specific experiments detailed are only illustrative of the invention as described more fully in the claims which follow thereafter.

Experimental Details

EXAMPLE 1

Summary

Cell-cell contact and TGF-β can arrest the cell cycle in G1. MvlLu mink epithelial cells arrested by either mechanism are incapable of assembling active complexes containing the G1 cyclin, cyclin E, and its catalytic subunit, Cdk2. These growth inhibitory signals block Cdk2 activation by raising the threshold level of cyclin E necessary to activate Cdk2. In arrested cells the threshold is set higher than physiological cyclin E levels, and is determined by an inhibitor that binds to cyclin E-Cdk2 complexes. A 27 kD protein that binds to and prevents the activation of cyclin E-Cdk2 complexes can be purified from arrested cells, but not from proliferating cells, using cyclin E-Cdk2 affinity chromatography. p27 is present in proliferating cells, but it is sequestered and unavailable to interact with cyclin E-Cdk2 complexes. Cyclin D2-Cdk4 complexes competitively bind to and down-regulate the activity of p27 and may thereby act in a pathway that reverses Cdk2 inhibition and enables G1 progression.

Methods

Cell Culture

Exponentially growing MvlLu cells were growth arrested by culturing them to confluence in the presence of 10% fetal bovine serum. Cells were released from contact inhibition by trypsinzation and reseeding in sparse conditions. TGF-β(100pM) was added to the cells at the indicated times. Cell entry into S phase was routinely confirmed by measuring $^{125}$Ideoxyuridine incorporation into DNA (Laiho et al. (1990)).

Preparation of Recombinant Proteins

Cyclin E, Cdk2, Cdk2-HA, and Cdk2K were prepared by the method of Desai et al. ((1992) Cell 3:571–582). Briefly, 100 mm plates of confluent Sf9 cells were infected with the appropriate baculovirus at an m.o.i. of 5–20 p.f.u. per cell. After 48 hours of infection, the cells were collected and lysed by Dounce homogenization or cup-horn sonication in hypotonic buffer. The extract is clarified by ultracentrifugation and stored at −70° C. The baculoviral vectors containing cyclins D1, D2, D3, Cdk4 and catalytically inactive Cdk4 have been previously described (Matsushime et al. (1992); Kato et al. (1993)).

Purification and Microsequencing of p27$^{Kip-1}$

In order to purify p27 in amounts sufficient for microsequence analysis, the purification protocol used as the starting material 200 15 cm dishes containing confluent cultures of contact inhibited MvlLu cells (~2×10$^{10}$ cells). Cells were lysed by sonication in 33 ml of hypotonic extraction buffer, and cell debris were removed by centrifugation at 200,000×g for 1 hour. The lysate was heated to 100° C. for 5 min., and precipitated material was removed by centrifugation at 100,000×g for 15 min. The supernatant was adjusted to NP-40 lysis buffer conditions (Polyak et al. (1994)) with 4× NP-40 lysis buffer, and precleared by two successive 30 min. incubations with 5 ml of agarose at 4° C. and once with 5 ml of nickel-NTA-agarose under the same conditions.

The precleared lysate was allowed to bind to an affinity column for 2 hours at 4° C. This affinity column consisted of nickel-NTA-agarose containing baculoviral Cdk2 in complex with baculoviral cyclin E tagged at the N-terminus with a hexahistidine sequence that allows binding to nickel-NTA-agarose. The column was washed once with 50 ml of NP-40 lysis buffer, and five times with 50 ml of SDS/RIPA buffer at room temperature. Bound proteins were eluted with 5 ml of a Hepes-buffered solution (pH 7.0) containing 6M guanidium hydrochloride. The eluate was dialyzed overnight against Hepes-buffered solution, and proteins were precipitated with 4 volumes of acetone at −20° C. for 30 min. Precipitated proteins were collected by centrifugation at 20,000×g for 15 min, solubilized in SDS electrophoresis sample buffer containing dithiothreitol, and electrophoresed on a 12% polyacrylamide gel. After electrophoresis, the gel was blotted onto nitrocellulose at 35V overnight in Tris/glycine/methanol transfer buffer.

The nitrocellulose membrane was stained with Ponceau stain to detect proteins. According to this assay, the filters contained only two proteins that were well separated from each other and were of 27 kd and 34 kd, respectively. These proteins were identified as p27 and p34$^{cdk2}$. Two separate preparations gave similar results. The yield of p27 in these two preparations was approximately 0.3 $\mu$g and 1 $\mu$g, respectively, as estimated from the Ponceau staining and from microsequencing.

The protein of nitrocellulose containing purified p27 was excised and subjected to tryptic digestion in preparation for microsequencing analysis. After HPLC of the tryptic digests, the following peptides were sequenced:

1. Asn-Leu-Tyr-Pro-Leu-Thr-Asn-Tyr-Thr-Phe (SEQ ID No. 7)
2. Thr-Asp-Thr-Ala-Asp-Asn-Gln-Ala-Gly-Leu-Ala-Glu-Gln (SEQ ID No. 8)
3. Gln-Ala-Val-Pro-Leu-Met-Gly-Pro-Gln-Glu (SEQ ID NO. 9)
4. Leu-Pro-Glu-Phe-Tyr-Tyr-Arg-Pro-Pro-Arg-Pro-Pro (SEQ ID No. 10)
5. Tyr-Glu-Trp-Gln-Glu-Val (SEQ ID No. 11)

No similarity has been found between these sequences and protein sequences deposited in Genbak, EMBL Data Library, Brookhaven Protein Databank, Swiss Prot or PIR databases, according to the updates available on Dec. 31, 1993.

Oligonucleotides for Obtaining p27 cDNA

Oligonucleotides to be used in obtaining the full-length cDNA sequence of p27 are shown in Table II:

all cases the exogenous cyclins and Cdks were added in the form of an unfractionated Sf9 cell lyeate. Cyclins and Cdks typically comprise at least 1–3% of total cell protein. Uninfected Sf9 cell lysates have been tested in all assays and have no activity. After 30 minutes at 37° C., the reaction was adjusted to 0.5% NP40, 250 mM NaCl and immunoprecipitated with the indicated antibody. Immunoprecipitates were subsequently assayed for histone H1 kinase activity as described (Koff et al. (1993) supra). For experiments in which the effect of the D cyclins and Cdk4 on cyclin E activity were tested, all cyclins and Cdks were added to the cell extract together.

Heat treatment of extracts was performed by incubating extracts to 100° C. for 5 minutes. Coagulated protein was then pelleted by microcentrifugation. For experiments in which Cdk2 immunoprecipitates were tested for activation by cyclin E, 20 µl of antiserum to the C-terminus of CDK2 (Koff et al (1993) supra) was adsorbed to protein A sepharose and washed into NP40 RIPA buffer. 300 µg of extract was subsequently incubated with the anti-CDK2 sepharose for 90 minutes at 4° C. The precipitate was washed twice with NP40 RIPA buffer and 4 times with buffer A containing 10 mM ATP. Cyclin E and CAK were added as described below and reactions were incubated for 30 minutes at 37° C. and subsequently assayed for H1 kinase activity.

TABLE II

```
Peptide #1: None
Peptide #2:
    Sense      5'-AC(N)-GA(T/C)-AC(N)-GA(T/C)-AA(T/C)-CA(A/G)-GC-3'        (SEQ ID NO. 12)
    Antisense  5'-(N)GC-(T/C)TG-(A/G)TT-(A/G)TC-(N)GC-(N)GT-(A/G)TC-       (SEQ ID NO. 13)
               (N)GT-3'
Peptide #3:
    Sense      5'-CA(C/G)-GC(N)-GT(N)-CC(N)-CT(N)-ATG-GG-3'                 (SEQ ID NO. 14)
         and 5'-CA(A/G)-GC(N)-GT(N)-CC(N)-TT(A/G)-ATG-GG-3'                 (SEQ ID NO. 15)
    Antisense  5'-(N)CC-CAT-(N)AG-(N)GG-(N)AC-(N)GC-(T/C)TG-3'              (SEQ ID NO. 16)
         and 5'-(N)CC-CAT-(T/C)AA-(N)GG-(N)AC-(N)GC-(T/C)TG-3'              (SEQ ID NO. 17)
Peptide #4:
    Sense      5'-CC(N)-GA(A/G)-TT(T/C)-TA(T/C)-TA(T/C)-(C/A)G-3'           (SEQ ID NO. 18)
    Antisense  5'-C(T/G)-(A/G)TA-(A/G)TA-(A/G)AA-(T/C)TC- (N)GG3'           (SEQ ID NO. 19)
Peptide #5:
    Sense      5'-TA(T/C)-GA(A/G)=TGG-CA(A/G)-GA(A/G(-GT-3'                 (SEQ ID NO. 20)
    Antisense  5'-(N)AC-(T/C)TC-(T/C)TG-CCA-(T/C)TC-(A/G)TA-3'              (SEQ ID NO. 21)
CAK
```

CAK was purified from Xenopus egg extracts through the Mono Q step exactly as described (Solomon et al. (1993)), and was used at a final concentration of 1–2 units per ml.

Metabolic Labeling

MvlLu cultures in 150 mm dishes were incubated for 30 minutes in methionine-free medium supplemented with 10% dialyzed fetal bovine serum, followed by incubation for 2 hours in the same medium with 200 µCi/ml of 35S-methionine (Trans 35S label, ICN). Cells were collected by trypsinization and centrifuged at 2000 g for 5 minutes. Cell pellets were lysed by gentle agitation for 30 minutes at 4° C. in 10 volumes of NP40 lysis buffer (50 mM Tris HCl pH 7.4, 200 mM NaCl, 2 mM EDTA, 0.5% NP40, 0.3 mM Na-orthovanadate, 50 mM NaF, 80 µM b-glycerophosphate, 20 mM Na pyrophosphate, 0.5 mM DTT and protease inhibitors) and lysates were clarified by centrifugation (10,000 g 15 minutes at 4° C.). Prior to binding reactions the supernatants were precleared twice with sepharose and once with protein A-sepharose.

Cdk Activation Assays

Indicated amounts of baculovirus expressed recombinant cyclin, Cdk, or cyclin-Cdk complex were added to 50 micrograms of extracts prepared by sonication in a hypotonic buffer as previously described (Koff et al. (1993)). In Inhibitor Depletion Cyclin E-Cdk2 sepharose was prepared by mixing 1.2 µl of Sf9 cell lysate containing Hemagglutinin tagged Cdk2 (Cdk2-HA) with 12 µl lysate containing cyclin E in buffer A (30 mM HEPES-KOH pH 7.5, 7.5 mM $MgCl_2$, 1 mM DTT) containing 10 mM ATP and incubated at room temperature for 30 minutes to allow complete formation. The assembly reaction was then adjusted to 250 mM NaCl and 0.5% NP40. The Cdk2-HA containing complexes were immunoprecipitated with the 12CA5 monoclonal antibody (BABCO) and collected on protein A-sepharose. Cdk2 sepharose was prepared in an identical manner except cyclin E was omitted. Immunoprecipitates were washed twice with NP40 RIPA buffer (0.5% NP40, 250 mM NaCl, 10 mM EDTA, 20 mM Tris-HCl pH 7.4) and four times with buffer A. The matrix was divided into 4 aliquots and incubated with 100 µg of cell extract in buffer A containing 3 mM ATP. 20 µg/ml creatine phosphokinase, 40 mM phospho-creatine for 45 minutes at 37° C. After incubation, the supernatant was collected and assayed for Cdk2 activation by addition of recombinant cyclin E as described below. A critical parameter in the execution of this experiment is to ensure that no cyclin, Cdk or complex leaks from the beads into the cell extract. This is unpredictable and must be checked by immunoblotting each time the experiment is performed.

Cyclin E-Cdk2 Binding Assays

Complexes of baculoviral cyclin E with baculoviral Cdk2 containing the influenza virus Hemagglutinin epitope HA1 were formed as described below. The complexes were immunoprecipitated in NP40-RIPA buffer (50 mM Tris-HCl pH=7.4, 250 mM NaCl, 0.5% NP-40, 50 mM NaF, 0.3 mM Na-ortho-vanadate, 5 mM EDTA and protease inhibitors) with anti-HA monoclonal antibody (12CA5, BabCo) and bound to protein A sepharose. Cdk2 or cyclin E-Cdk2 adsorbed to protein A-sepharose were incubated with metabolically labeled cell lysates from 107 cells for 2 h at 4° C. Unless otherwise indicated, the beads were washed several times with SDS-RIPA buffer, and the proteins were eluted by heating in SDS-PAGE sample buffer and analyzed on 12% polyacrylamide gels followed by fluorography. For heat treatment, metabolically labeled cell lysates were heated for 3 minutes at 100° C., the precipitated proteins were removed by microcentrifugation and the clarified lysates were incubated with protein A-sepharose bound Cdk2 or cyclin ECdk2 complexes. In binding assays using cyclin D2-Cdk4 complexes, metabolically labeled cell extracts were pre-incubated with 4 µl of cyclin D2-Cdk4 complex for 30 minutes at 4° C. before addition of protein A-sepharose bound Cdk2 or cyclin E-Cdk2. After removing the sepharose beads, cell extracts were immunoprecipitated with Cdk4 antiserum and the immunoprecipitates were analyzed on 12% SDS-PAGE.

Affinity Purification of p27 and Denaturation-renaturation Experiments

HA-tagged Cdk2, alone or in complex with cyclin E, was bound to HA antibody immobilized on protein A sepharose beads (ImmunoPure Orientation Kit, Pierce,) and used to isolate proteins from metabolically labeled cell lysates. Bound proteins were eluted from the column in 0.1M glycerine pH 2.8 and precipitated with 4 volumes of ice-cold acetone and kept at −20° C. for 20 minutes. The precipitates collected by microcentrifugastion for 30 minutes were washed several times with cold acetone, and dissolved in 6M guanidine chloride in 1×HBB buffer (25 mM HEPES-KOH pH 7.7, 25 mM NaCl, 5 mM $MgCl_2$, 0.05% NP-40, 1 mM DTT). For renaturation (Kaelin et al. (1992)), samples were dialyzed overnight against 1×HBB buffer and used either in kinase inhibition assays or for binding to cyclin E-Cdk2 sepharose. For cyclin E associated H1 kinase inhibition assays, aliquots (37.5 llg of protein) from 100,000×g supernatants of lysates prepared from exponentially growing MvlLu cells, were incubated for 30 min. at 37° C. with physiological amounts of baculoviral cyclin E either alone or in the presence of the indicated volumes of renatured eluates. After incubation, samples were precipitated with cyclin E antiserum, and assayed for histone H1 kinase activity. The relative cyclin E-associated H1 kinase activity was quantitated using a Molecular Dynamics Phosphorimager ImageQuant software.

To assay the activity of protein eluted from gel slices cyclin E-Cdk2-HA affinity column eluates were run on 12% polyacrylamide gels along with molecular weight markers (Amersham). Part of the sample was run on the same gel, stained with Commassie, destained and detected by fluorography. The gel was cut as indicated (between 0.5 to 1 cm/slice) and the proteins were isolated from the gel as described (Boyle et al. (1991) *Methods in Enzymology* 201:110–149). The isolated proteins were renatured and used for kinase inhibition assays as described below.

Results

Non-proliferating Cells Contain an Inhibitor of Cdk2 Activation

Cell free extracts from contact inhibited, TGF-β arrested and proliferating cells were used to investigate the mechanism that blocks activation of the cyclin E-Cdk2 complex. It has been shown that addition of physiological amounts of cyclin E to these cell extracts resulted in an increase in the amount of immunoprecipitable cyclin E-Cdk2 complexes; however, only the cyclin E-Cdk2 complexes assembled in extracts from proliferating cells were enzymatically active using histone H1 as a substrate (Koff et al (1993), supra; see also FIG. 1A). Cell extracts, therefore, recapitulate the block to Cdk2 activation observed in intact cells.

The block to Cdk2 activation in extracts from non-proliferating cells could be overcome by addition of cyclin E protein to greater than physiological levels (FIG. 1A). Cyclin E was expressed in Sf9 cells using a baculoviral expression vector and the amount of cyclin E in Sf9 extracts was compared to that in MvlLu cell extracts by immunoblotting (not shown). In the experiment illustrated in FIG. 1A, 0.05 µl of Sf9 lysate contained as much cyclin E as 50 µg of total cell protein from MvlLu cell lysates. Addition of cyclin E (in the form of Sf9 lysate) to an extract from proliferating cells gave a linear increase in cyclin E-associated histone H1 kinase activity (proliferating cells were harvested 15 hours after release from contact inhibition, at which time they were in early S phase). In contrast, titration of up to 3 times physiological levels of cyclin E into extracts from contact inhibited or TGF-β treated cells resulted in no increase in immunoprecipitable cyclin E-associated kinase activity. As more cyclin E was added, cyclin E-associated kinase activity became detectable and increased in proportion. Thus, extracts from non-proliferating cells demonstrated an elevated threshold level of cyclin E necessary to activate Cdk2.

Contact inhibited cells appeared to have a higher threshold than cells arrested in G1 by exposure to TGF-β, but in both cases the cyclin E requirement was substantially greater than the physiological levels of cyclin E achieved in proliferating cells.

Figure 1B:
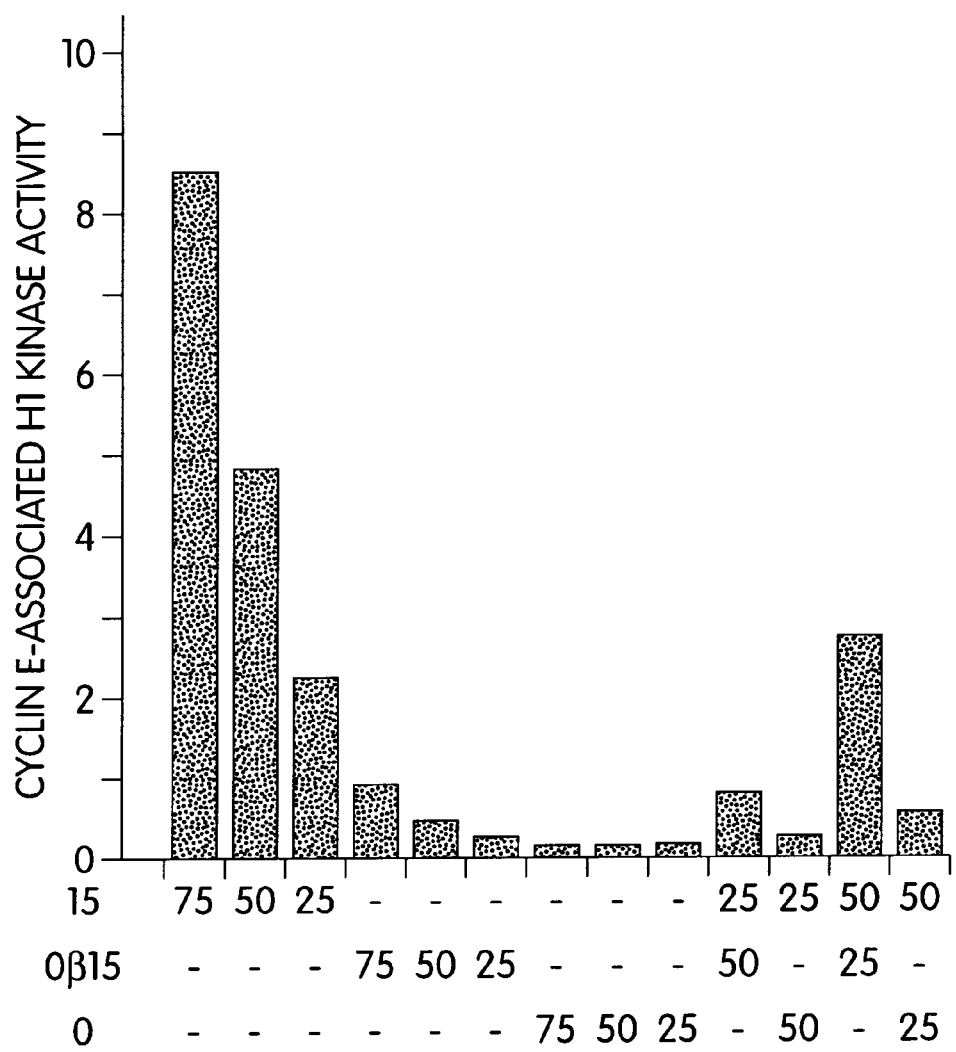

Supra-physiological amounts of cyclin E were required to activate Cdk2 in extracts from non-proliferating cells. This could not be explained by lower levels of Cdk2 or cyclin E, nor did these cells appear to lack other factors necessary for Cdk2 activation (Koff et al., (1993) supra; see below). One explanation was that non-proliferating cells contained a titratable inhibitor of Cdk2 activation. Mixing experiments supported this conclusion. Extracts from proliferating cells were mixed with those from either contact inhibited or TGF-β treated cells. Physiological levels of cyclin E were added to the mixed extracts and then cyclin E and any associated kinases were immunoprecipitated using antibodies to the cyclin. Identical results were obtained using an anti-Cdk2 antiserum (not shown). In mixed extracts cyclin E-associated kinase activity was reduced below that recovered from extracts of proliferating cells alone (FIG. 1B). Thus, extracts from non-proliferating cells contained an excess of an inhibitor of Cdk2 activation. Note that extracts from contact inhibited cells had both a higher cyclin E activation threshold and a greater inhibitory effect in mixing experiments than extracts from TGF-β treated cells. However, the abundance of the Cdk2 inhibitory activity depended upon the duration of exposure to TGF-β. For instance, it is shown that an extract from cells exposed to TGF-β for 6 hours beginning in late G1 did not contain sufficient inhibitory activity to block Cdk2 activation when mixed with an extract from proliferating cells (Koff et al. (1993) supra) and cells exposed to TGF-β for 48 hours had more inhibitory activity that cells exposed for 15 hours (not shown).

A Cdk2 Inhibitor Binds to Cyclin E-Cdk2 Complexes

Figure 2A:
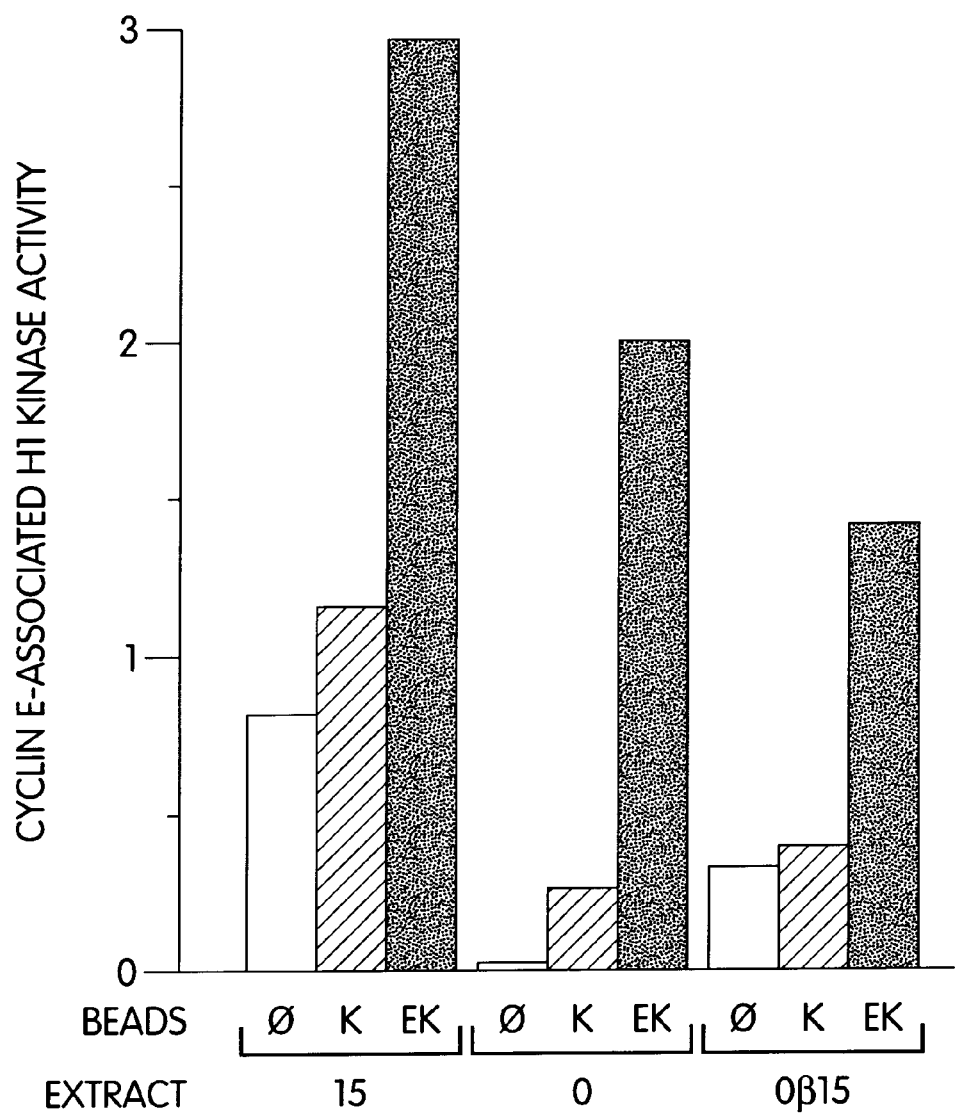

The inhibitor of Cdk2 activation present in extracts from non-proliferating cells could be depleted using a cyclin E-Cdk2 affinity matrix. Cyclin E-Cdk2 complexes were formed by mixing extracts from Sf9 cells infected with baculoviral vectors expressing either Cdk2 tagged with an influenza virus hemagglutinin (HA) epitope or cyclin E. Although neither extract alone contains significant H1 kinase activity, mixing of the extracts yields high levels of active enzyme (Kato et al. (1993)). The cyclin E-Cdk2 (HA) complexes were immunoprecipitated with sepharose-linked monoclonal antibody directed against the HA tag on Cdk2. Control immunoprecipitations were performed using the monoclonal antibody beads alone. Cell extracts were incubated with either the cyclin E-Cdk2 beads or the control beads, and after pelleting the supernatants were assayed for the ability of exogenously added cyclin E to activate endogenous Cdk2. After depletion of cyclin E-Cdk2 binding proteins, cyclin E was able to activate Cdk2 almost equally in extracts from proliferating and non-proliferating cells (FIG. 2A). Immunoblotting showed that this protocol had no effect on the levels of either cyclin E or Cdk2 in the cell extracts (not shown). In this experiment some stimulatory effect of depleting cyclin E-Cdk2 binding proteins was also observed in extracts from proliferating late G1 cells, suggesting they are not completely devoid of the inhibitor (see below). Complexes containing cyclin E and a catalytically inactive mutant of Cdk2 also were able to sequester inhibitory activity when added directly to cell extracts (see FIG. 2C). Thus reversal of inhibitory activity did not require phosphorylation by the added cyclin E-Cdk2 complexes. These experiments showed that the inhibitor of Cdk2 activation bound to cyclin E-Cdk2 complexes.

Figure 2B:
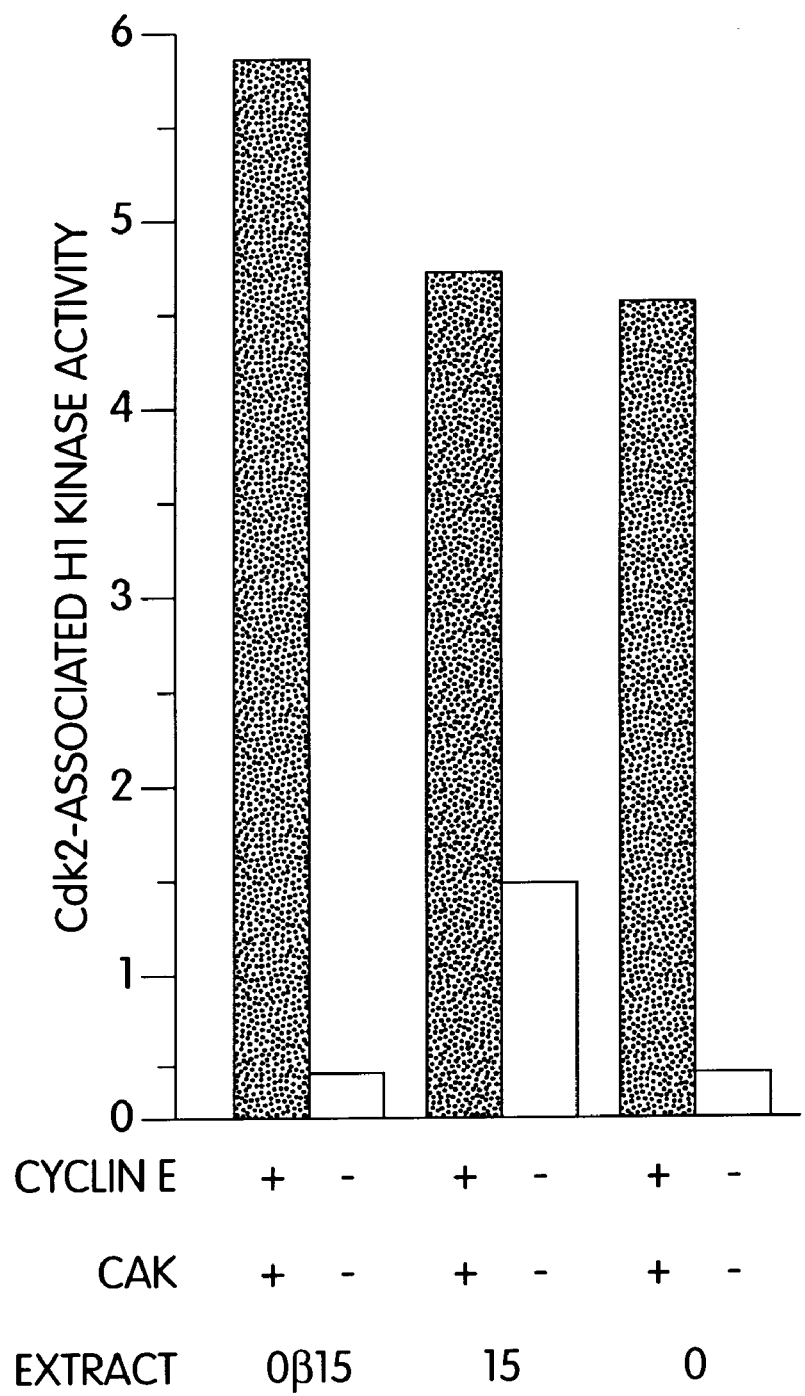

In parallel, it is observed that beads containing just Cdk2 alone were unable to deplete the inhibitory activity from cell extracts (FIG. 2A). This experiment suggested that the inhibitor bound to cyclin E-Cdk2 complexes, but not to Cdk2 alone. To directly test this idea. Cdk2 was immunoprecipitated from extracts of prliferating, contact inhibited and Tgf-β treated cells. In all cases, the immunoprecipitated Cdk2 protein could be activated by addition of both cyclin E and p34cdc2 activating kinase (CAK) (FIG. 2B). Thus, the Cdk2 protein in non-proliferating cells was not intrinsically incapable of activation, nor was it tightly associated with an inhibitor of activation.

Figure 2C:
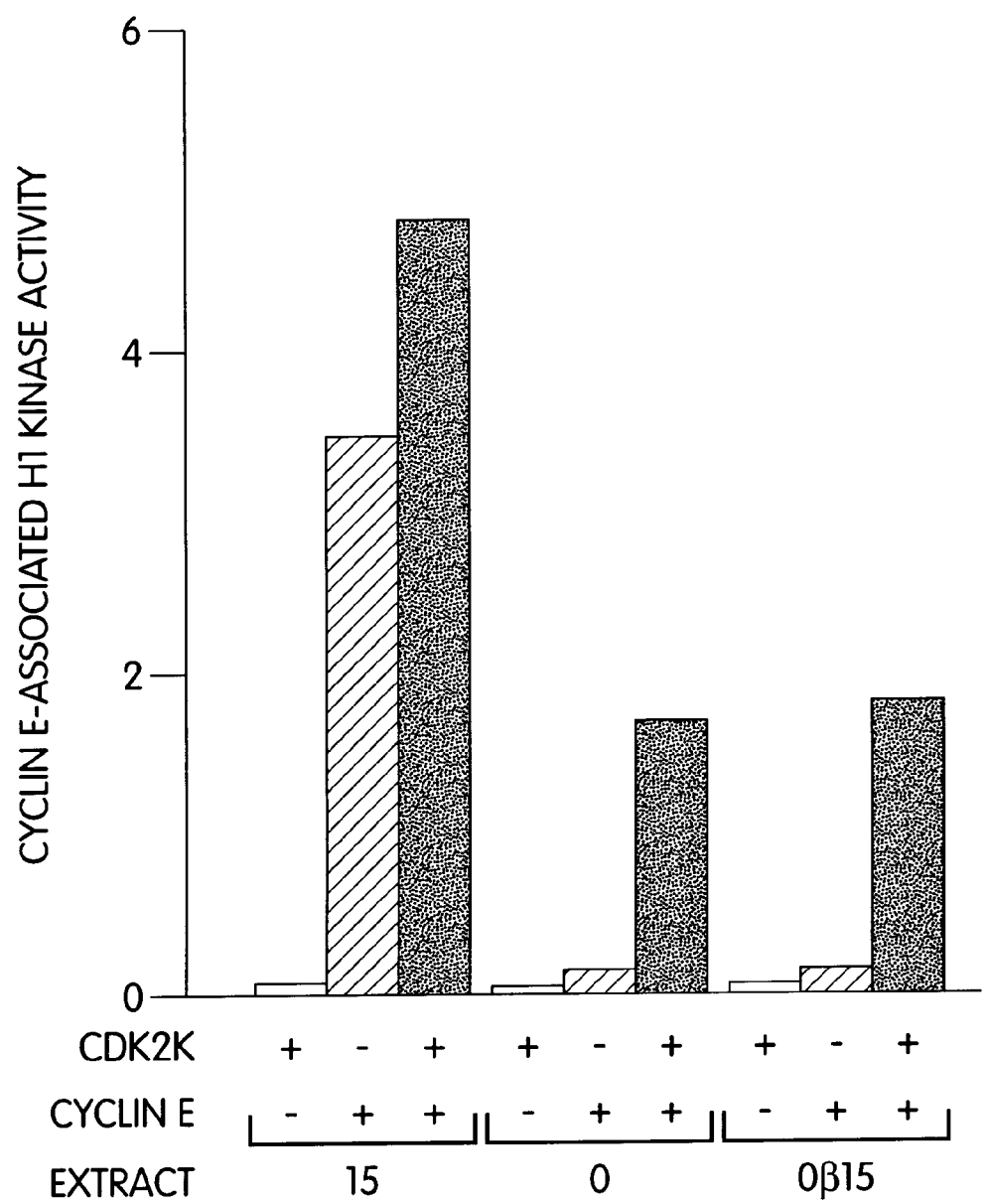

Since the Cdk2 inhibitor could bind to cyclin E-Cdk2 complexes, but not to Cdk2, it appeared to recognize either the cyclin-Cdk complex or cyclin. Cyclin E-Cdk2 complexes were more effective at removing the inhibitory activity than was cyclin E, suggesting that the inhibitor interacted preferentially with complexes. Cyclin E was added to a non-proliferating cell extract at a level below the threshold necessary to activate Cdk2 (FIG. 2C). The assembly of additional cyclin-Cdk2 complexes was then induced by supplementing the extracts with an exogenous Cdk2 protein that was rendered catalytically inactive by a mutation of its ATP binding site (Gu et al. (1992) supra). In the absence of extra Cdk2 no kinase activity was detected in cyclin E immunoprecipitates. When extracts were supplemented with catalytically inactive Cdk2, cyclin E regained H1 kinase activity as a result of activating the endogenous Cdk2. Thus, the cyclin E threshold for Cdk2 activation could be lowered by assembling additional cyclin-Cdk complexes while keeping the total amount of cyclin E constant.

The inhibitor is neither an anti-CAK nor a tyrosine kinase

Previous experiments (Koff et al. (1993), supra) indicated that cyclin E-Cdk2 complexes formed in extracts from non-proliferating cells were not phosphorylated at an essential threonine residue (Gu et al. (1992) supra; Solomon et al. (1992)) possibly accounting for their inactivity. This raised the possibility that CAK was a target of the inhibitor. This initially seemed unlikely because the inhibitor bound directly to the cyclin E-Cdk2 complex. This idea was reconsidered in light of recent evidence that CAK is itself a distant member of the Cdk protein family (Fesquet D. et al. (1993) *EMBO J.* 12:3111–3121; Poon et al. (1993); Solomon et al. (1993)) and therefore might also bind to the inhibitor. Previous work, in another system indicated that activation of the cyclin B-Cdc2 complex was not blocked by the Cdk2 inhibitor (see below). Cyclin B and Cdc2 were therefore used to assay CAK activity, given that CAK is also required to activate the cyclin B-Cdc2 complex (Solomon et al. (1990)).

Figure 3A:
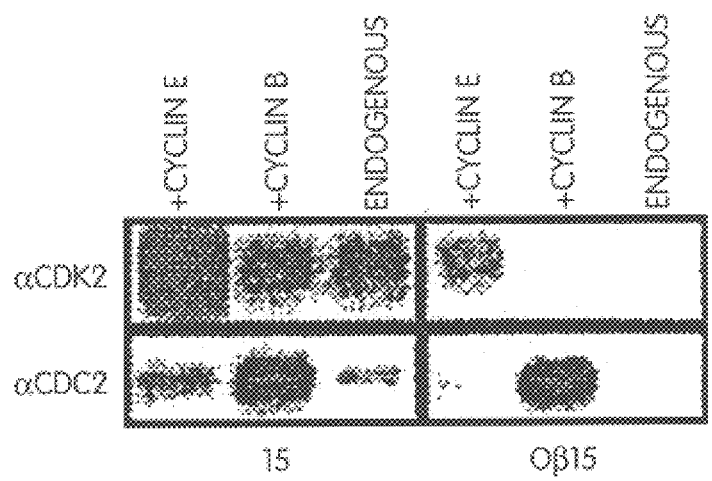
Figure 3B:
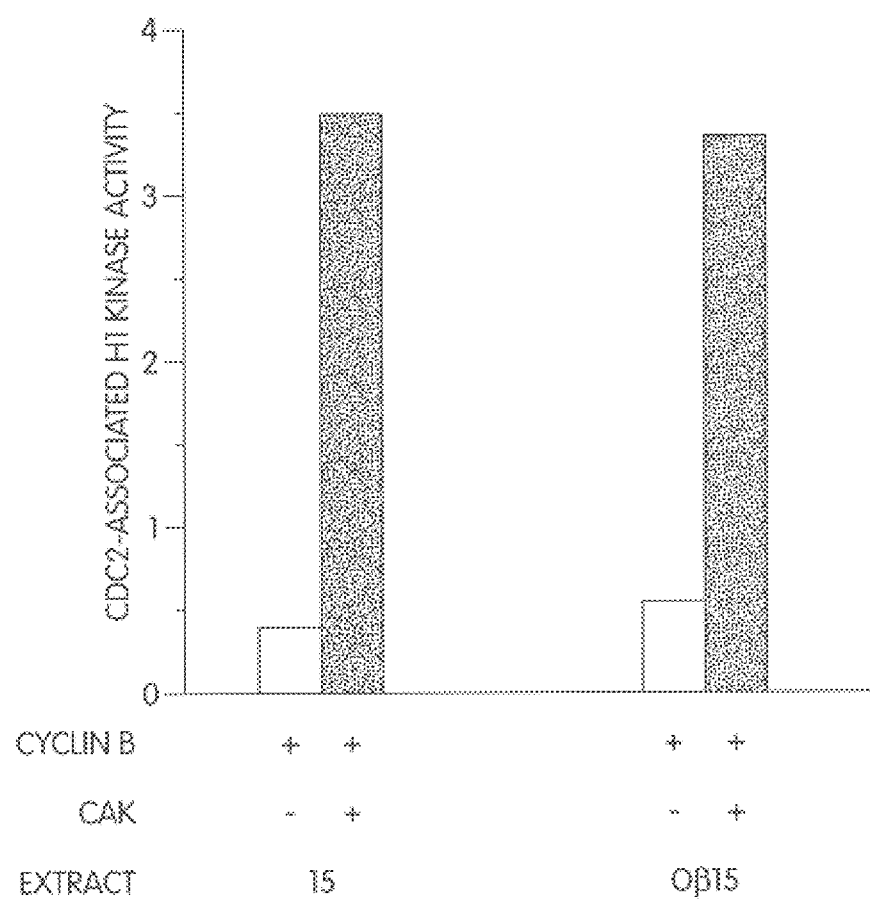

Cdc2 was activated equally when cyclin B was added to extracts from either proliferating cells or TGF-β arrested cells (FIG. 3A). Therefore, functional CAK was present in extracts from TGF-β treated cells. CAK was limiting in this experiment since addition of purified CAK to these extracts catalyzed the activation of additional cyclin B-Cdc2 complexes (FIG. 3B). Moreover, the activity of the added CAK was similar in extracts from TGF-β treated and proliferating cells (FIG. 3B). Thus, exogenous CAK was not inhibited. Control experiments showed that this CAK was able to activate cyclin E-Cdk2 complexes when they were assembled by mixing Sf9 cell lysates containing cyclin E and Cdk2 expressed from baculoviral vectors (Solomon et al. (1993), supra; data not shown). Thus, the inhibitor neither blocked CAK nor could its effects be overcome by excess CAK. Inhibition of CAK was not sufficient to explain the block to Cdk2 activation.

To determine if tyrosine phosphorylation contributed to the inhibition of Cdk2 activity, cyclin E was added to non-proliferating cell extracts at sub-threshold levels and the cyclin E-Cdk2 complexes were immunoprecipitated using anti-cyclin E antibodies. No tyrosine phosphorylation of Cdk2 in the inactive cyclin E-Cdk2 complexes was detected by immunoblotting with anti-phosphotyrosine antibodies (not shown). As a positive control, phosphotyrosine was readily detected in Cdc2 immunoprecipitated from human cells.

Cyclin D2-Cdk4 Complexes Facilitate Cdk2 Activation

As cells traverse G1, complexes between Cdk4 and the D-type cyclins appear prior to the formation of active complexes containing cyclin E and Cdk2 (reviewed in Sherr (1993)). Contact inhibited MvlLu cells do not express significant levels of cyclin D1 or D2 (not shown) and Cdk4 synthesis is repressed in cells arrested in G1 by exposure to TGF-β (Ewen et al. (1993), K. P. and J. M., unpublished observations; see also FIG. 5D). Thus, accumulation of cyclin D-Cdk4 complexes is limiting in G1 arrested cells. These observations suggested that cyclin D-Cdk4 complexes could potentially have a role in removing the Cdk2 inhibitor during cell cycle progression. Indeed, Ewen et al.(1993b) supra, recently showed that constitutive ectopic expression of Cdk4 can override the TGF-β block to Cdk2 activation and cell cycle progression. This phenomenon was tested by asking whether the restoration of cyclin D-Cdk4 complexes to extracts from non-proliferating cells might overcome the block to Cdk2 activation.

Figure 4A:
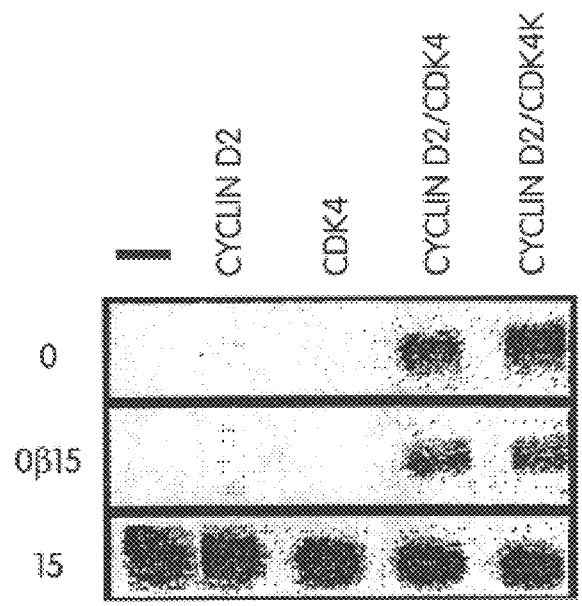
Figure 4B:
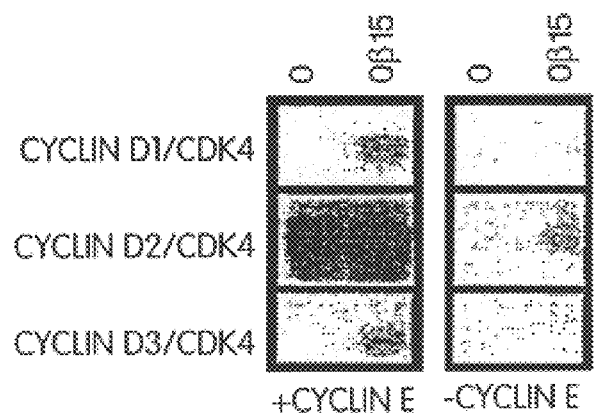

Cdk4 is a partner of the D-type cyclins and does not form active complexes with cyclins E, A or B. It interacts equally well with each of the D-type cyclins when they are co-expressed in insect cells. Cyclin D-Cdk4 complexes are poorly active on histone H1 but show strong activity using the Rb protein as substrate (Matsushime et al. (1992); Kato et al. (1993) supra). Complexes between Cdk4 and either cyclin D1, D2 or D3 were assembled by co-infection of Sf9 cells with baculoviral vectors and Sf9 lysates were added to extracts from proliferating and non-proliferating MvlLu cells. Sub-threshold amounts of cyclin E were then added, and activation of Cdk2 was tested after immunoprecipitation of cyclin E-Cdk2 complexes with antibodies to cyclin E. Addition of cyclin D2-Cdk4 complexes, but neither subunit alone, to extracts from contact inhibited and TGF-β arrested cells allowed cyclin E to activate Cdk2 to a level equivalent to that observed in extracts from proliferating cells (FIG. 4A). Titrations demonstrated that the amount of cyclin D2-Cdk4 necessary to block the Cdk2 inhibitor was less than that present in an equivalent amount of extract from proliferating cells (not shown). In contrast, the activity of cyclin E was not increased when cyclin D2-Cdk4 complexes were added to extracts from proliferating cells. Moreover, the cyclin D2-Cdk4 complex did not have CAK activity, since it was unable to substitute for CAK in promoting the activation of cyclin E-Cdk2 complexes assembled from proteins expressed in Sf9 cells (not shown). Thus, the cyclin D2-Cdk4 complex reversed the inhibition of Cdk2 activation. Equal amounts of cyclin D1-Cdk4 and cyclin D3-Cdk4 complexes, as estimated by immunoblotting of Sf9 lysates, were much less effective in lowering the cyclin E threshold for Cdk2 activation (FIG. 4B). The inability of cyclin D1- or cyclin D3-Cdk4 complexes to sequester the Cdk2 inhibitor was not because those complexes were unstable in cell lysates (not shown).

Quite surprisingly, the ability of cyclin D2-Ckd4 to reverse Cdk2 inhibition did not require Cdk4 catalytic activity. Complexes formed between cyclin D2 and a catalytically inactive mutant Cdk4 subunit were as complexes in removing enzymatically active cyclin D2-Cdk4 complexes in removing the Cdk2 inhibitor (FIG. 4A). Titrations with different amounts of cyclin D2 complexes containing either catalytically active or inactive Cdk4 revealed that their specific activities in reversing the Cdk2 inhibition were very similar (not shown). This ruled out the possibility that cyclin D2-Cdk4 must phosphorylate the inhibitor to inactivate it, and excluded any model in which cyclin D2-Cdk4 bypassed the inhibitor by functioning as a CAK. It therefore seemed likely that cyclin D2-Cdk4 removed the Cdk2 inhibitor by binding to it directly and sequestering it from Cdk2 (see below).

The Cdk2 Inhibitor is a 27 kd Protein

Figure 5A:
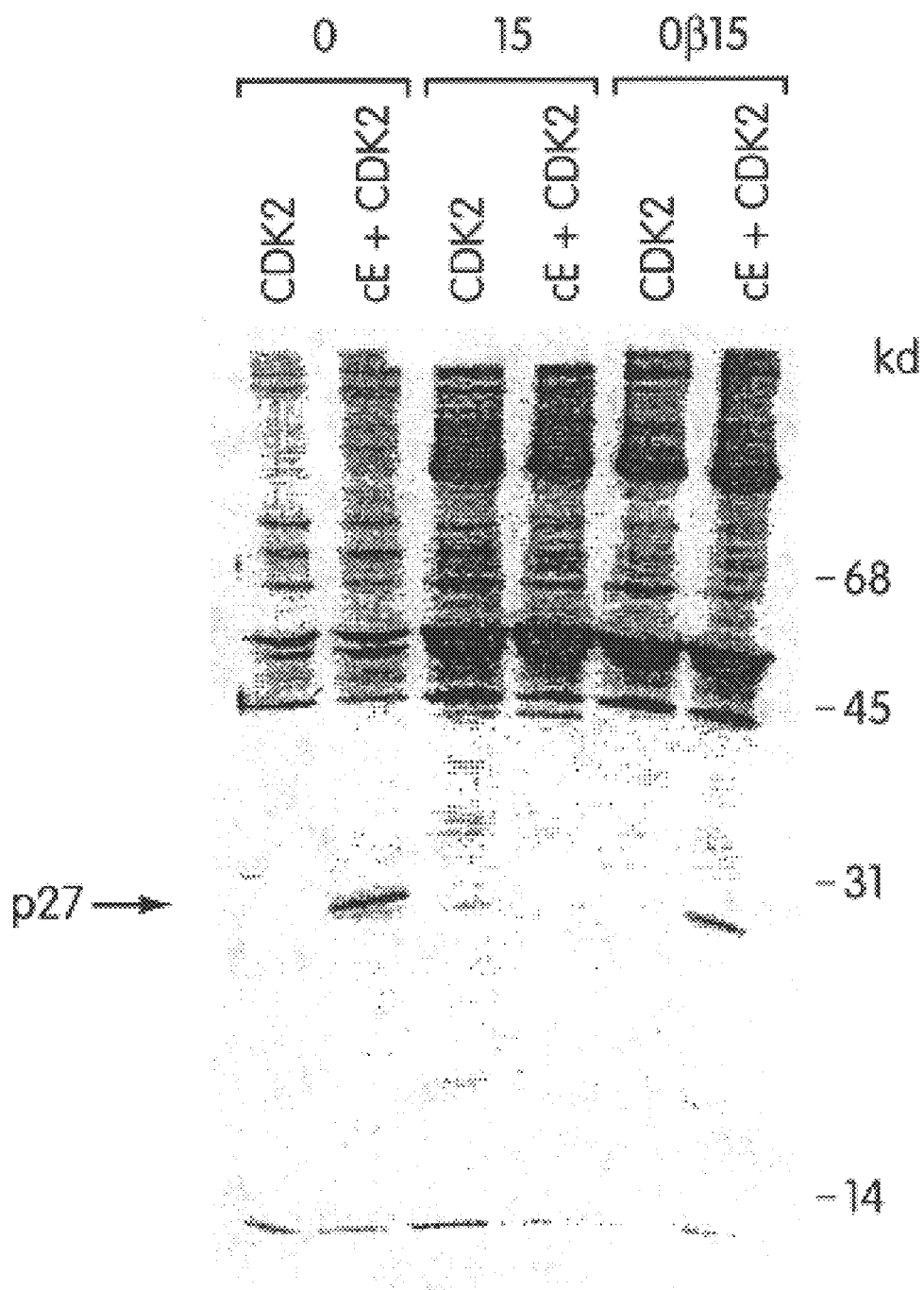
Figure 5B:
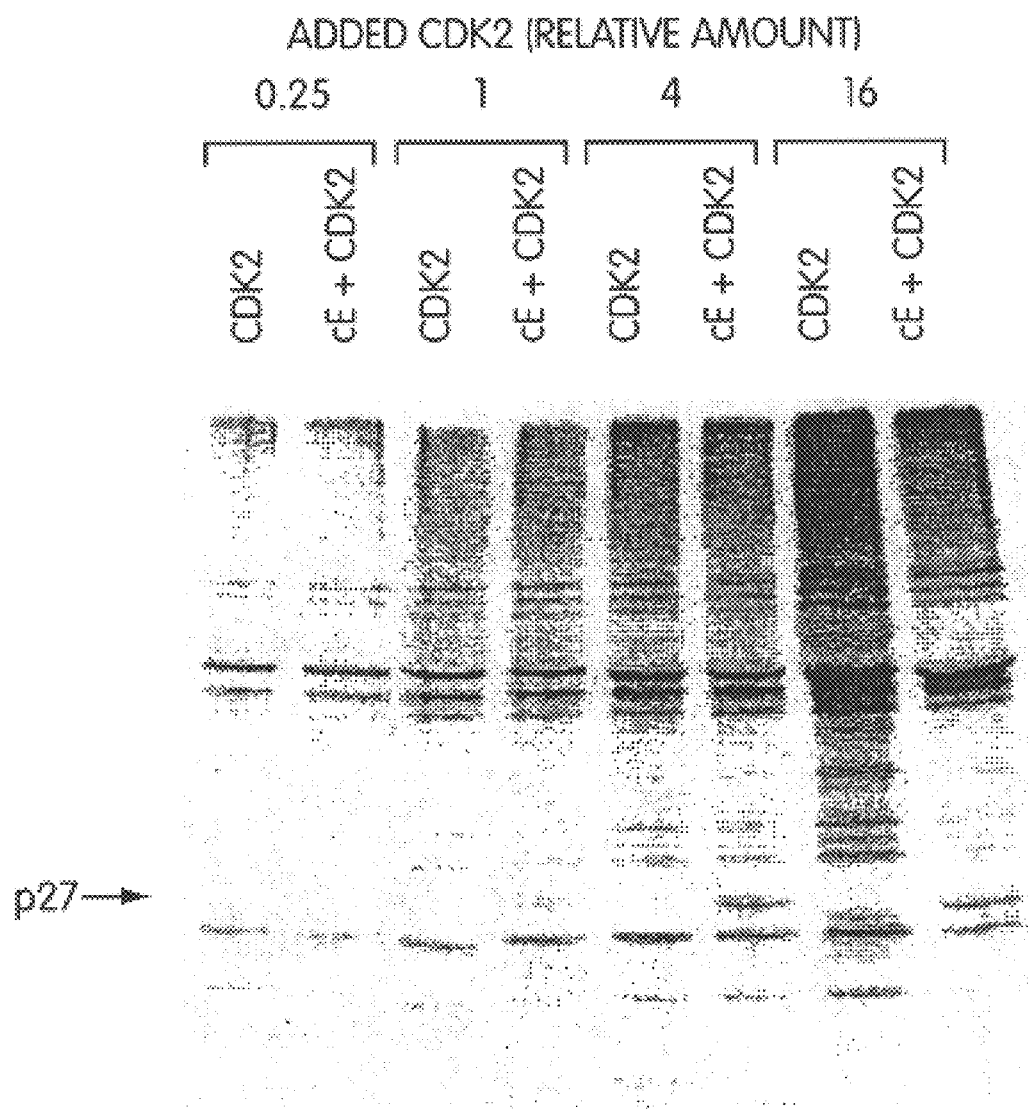

The above observations indicated (i) that a functional cyclin E-Cdk2 inhibitor was present in extracts from contact inhibited cells or cells released from contact inhibition in the presence of TGF-β, but not in extracts from proliferating cells; (ii) that this molecule preferentially associated with cyclin E-Cdk2 complexes as opposed to either subunit alone; and (iii) that it could be depleted by preincubation of cell extracts with catalytically active or inactive cyclin D2-Cdk4 complexes. To identify a factor that might display these properties, MvlLu cells were metabolically labeled with 35S-methionine, and lysates were incubated with sepharose beads that contained immunoadsorbed recombinant Cdk2, either alone or in complexes with recombinant cyclin E. Denatured 35S-labeled proteins, eluted by heating the beads with buffer containing 1% SDS, were visualized by gel electrophoresis and fluorography (FIG. 5A). All cell lysates yielded a similar pattern of cyclin E-Cdk2-binding proteins with the exception of a 27 kd protein that was recovered from extracts of contact inhibited or TGF-β inhibited cells, but not late G1 phase cells (FIG. 5A). This protein, referred to as p27, was isolated using cyclin E-Cdk2 complexes but not Cdk2 alone (FIG. 5A). The recovery of p27 increased in proportion to the amount of cyclin E-Cdk2 complex used until it reached a maximum (FIG. 5B), indicating that binding of p27 to cyclin E-Cdk2 complexes was saturable. This was consistent with the observation that Cdk2 inhibitor activity could be depleted by cyclin E-Cdk2 complexes. As expected, stoichio-metric amounts of p27 were also observed in cyclin E immunoprecipitates from growth arrested cells (not shown).

Figure 5C:
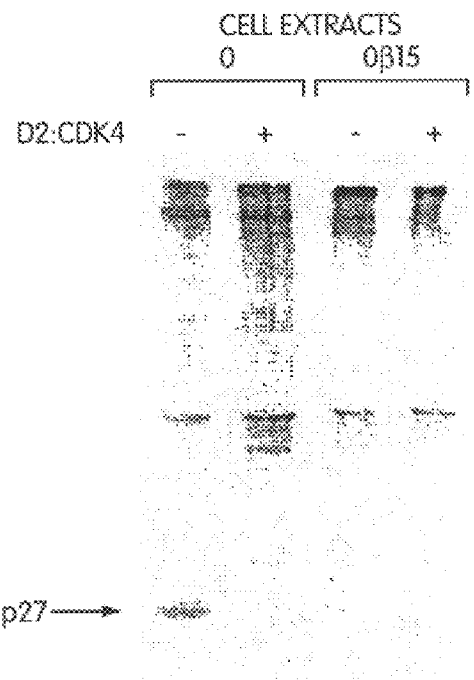
Figure 5D:
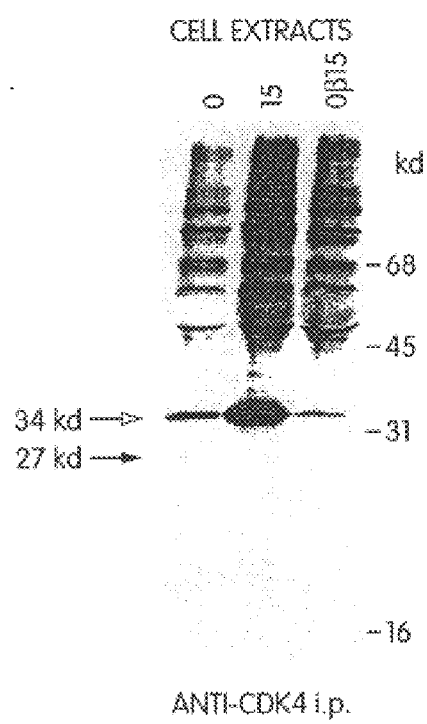

Cell extracts that received recombinant cyclin D2-Cdk4 complex no longer yielded p27 when the mixture was adsorbed to cyclin E-Cdk2-Sepharose (FIG. 5C). After removal of the cyclin E-Cdk2-Sepharose beads from samples that received cyclin D2-Cdk4, the precleared supernatants were incubated with Cdk4 antibody to recover Cdk4 and its associated proteins. This yielded p34Cdk4 itself, whose levels were highest in extracts from cells in late G1 and lowest in TGF-β treated cells (FIG. 5D) (Matsushime et al. (1992), supra; Ewen et al. (1993b) supra). Using the same antiserum, Ewen et al used partial proteolytic digestion to confirm that this is authentic MvlLu Cdk4. In addition, these immunoprecipitates contained a 27 kD protein in samples from contact inhibited and TGF-β treated cells (FIG. 5D). Lesser amounts of p27 were also recovered in Cdk4 immunoprecipitates from late G1 cell samples, even though p27 could not be recovered from those same extracts by cyclin E-Cdk2 affinity chromatography. This suggested that p27 was present in prliferating cells, but in a form unavailable to interact with exogenously added cyclin E-Cdk2 complexes (see below). Side-by-side comparison showed that p27 purified on cyclin E-Cdk4 beads or by co-precipitation with Cdk4 had the same apparent molecular weight (not shown).

Figure 6A:
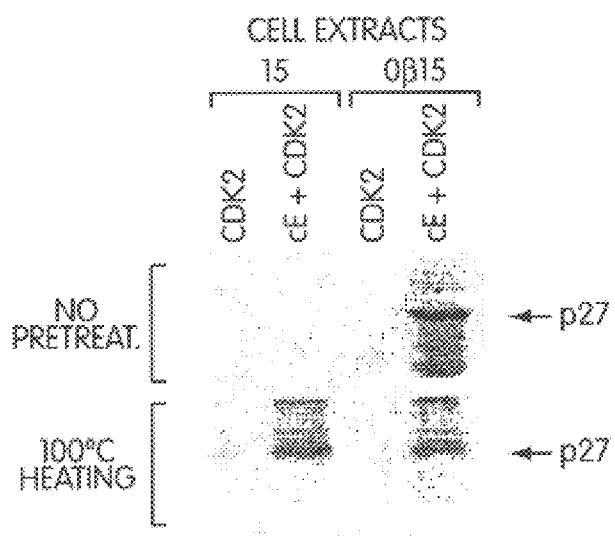
Figure 6B:
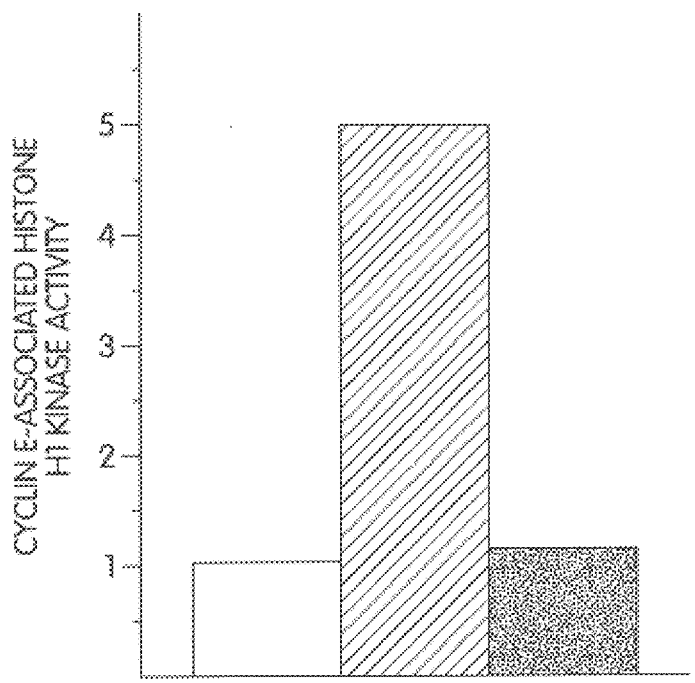
Figure 6C:
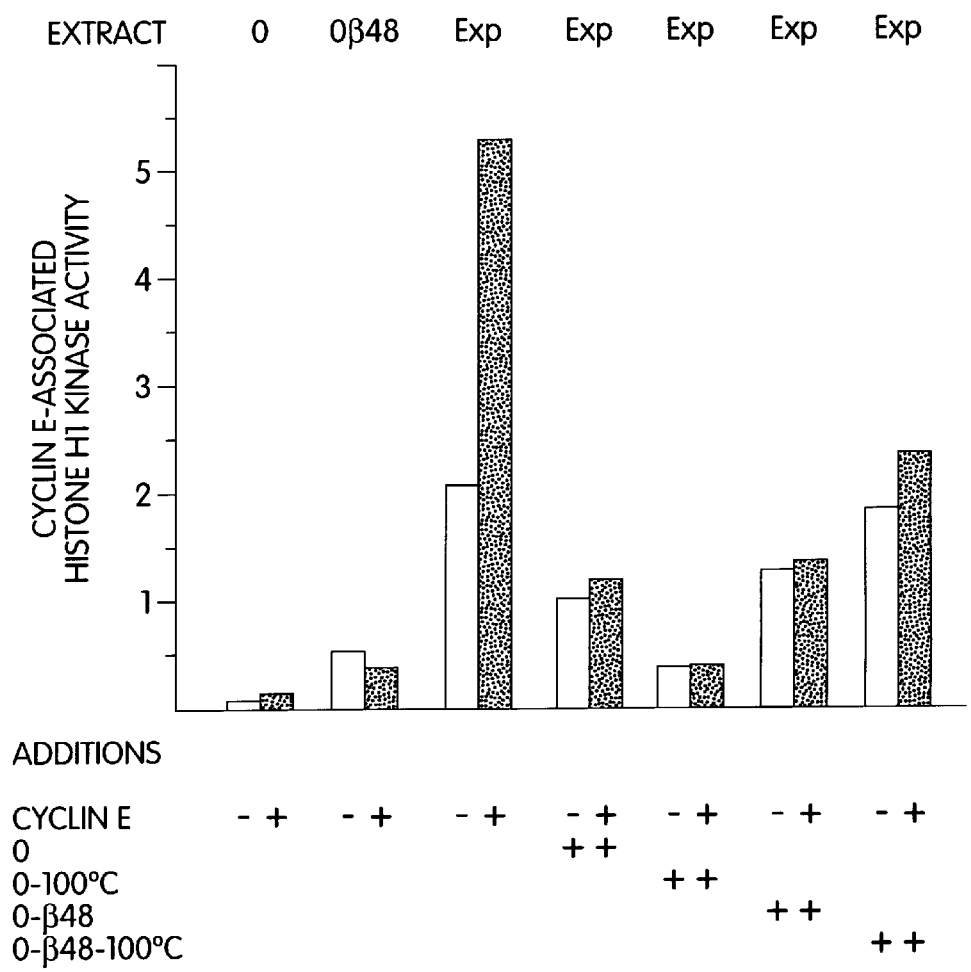

Experminets done to characterize the stability of this factor shown that heating cell extracts to 100° C. for a brief period preserved both the ability of p27 to bind to cyclin E-Cdk2 (FIG. 6A), and the inhibitory activity as well (FIG. 6C). Furthermore, when applied to extracts from cells in late G1 phase, heat treatment unexpectedly induced the appearance of both p27 (FIG. 6A) and concomitantly increased the level of Cdk2 inhibitory activity (FIG. 6B). These results indicated that p27 and the inhibitory activity were both heat stable, and that they could be reactivated in late G1 extracts by a heat-sensitive mechanism. As expected, cyclin D2-Cdk4 complexes were also able to sequester p27 from heat treated lysates (not shown).

Figure 7A:
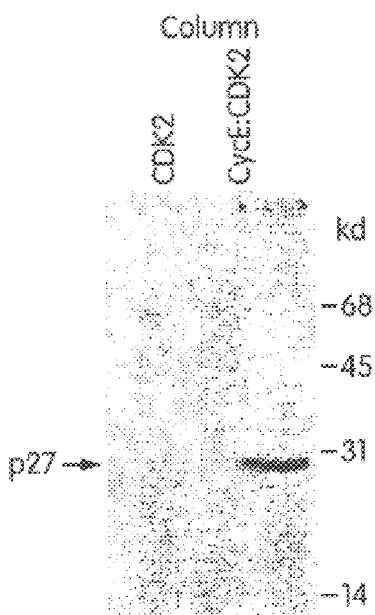
Figure 7B:
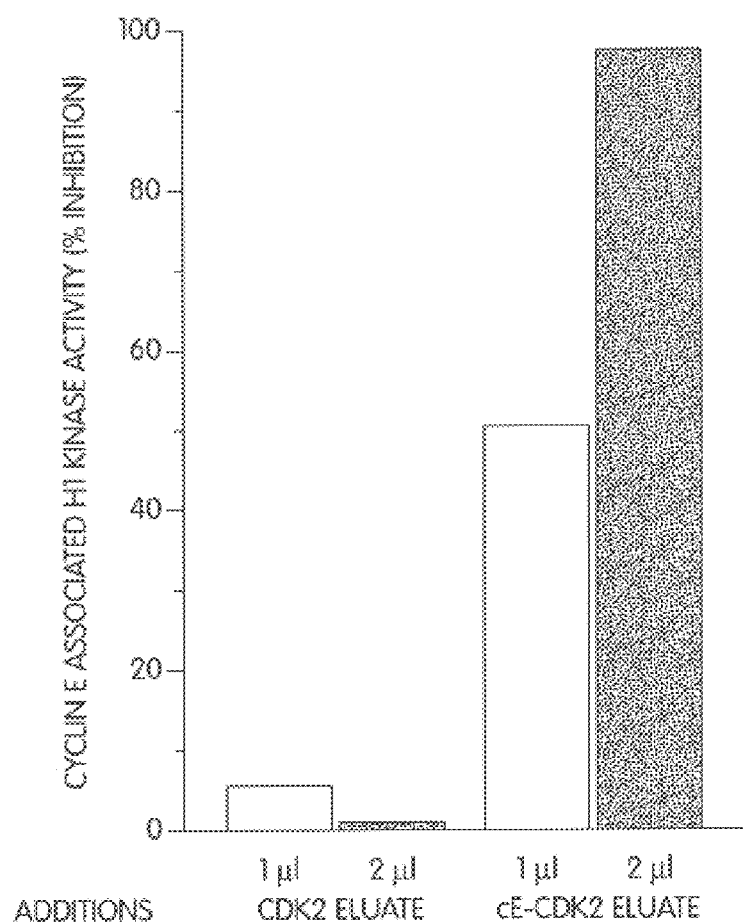
Figure 7C:
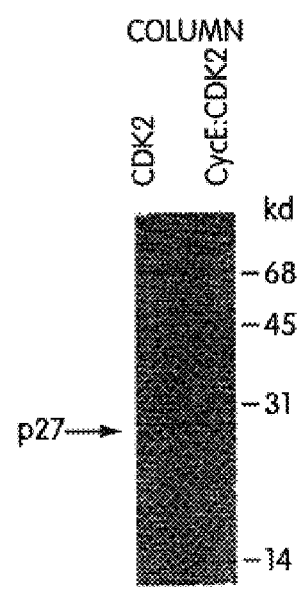

Extracts from metabolically-labeled TGF-β treated cells were subjected to chromatography over cyclin E-Cdk2-sepharose or, as a control, Cdk2-sepharose. After washing, the beads were eluted with an acidic buffer, and one portion of the eluate was analyzed by SDS PAGE. This showed that p27 was the predominant labeled species recovered and was present only in the eluate from cyclin E-Cdk2 beads (FIG. 7A). Samples from the same eluates were assayed for the presence of the Cdk2 inhibitor, and this activity was present in the eluate from cyclin E-Cdk2 beads but not Cdk2 beads (FIG. 7B). The remainder of the eluate was concentrated by acetone precipitation, denatured in 6M guanidium hydrochloride, renatured by dialysis against isotonic buffer and subjected to a second round of binding to cyclin E-Cdk2 Sepharose. Elution from these beads by boiling in buffer containing 1% SDS yielded p27 as the only labeled band (FIG. 7C). These results strongly supported the possibility that p27 and the inhibitory activity are one and the same.

Figure 7D:
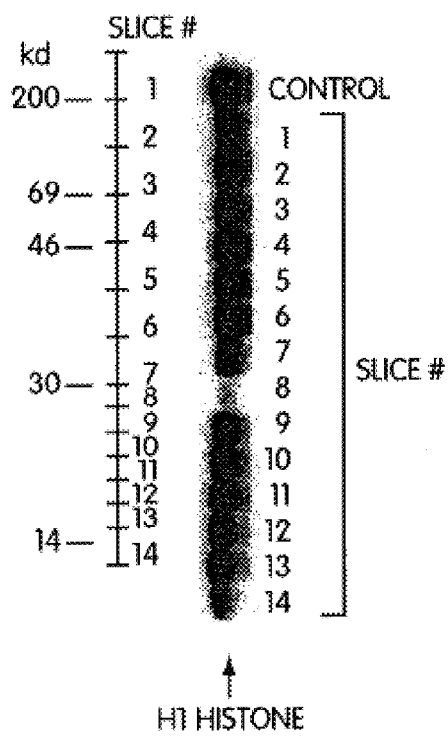

This conclusion was directly confirmed by fractionating the cyclin E-Cdk2 eluate by polyacrylamide gel electrophoresis and extracting the fractionated proteins from gel slices. Renatured proteins were tested for their ability to inhibit activation of Cdk2 by cyclin E (FIG. 7D). The protein recovered from the gel slice containing p27 completely inhibited Cdk2 activation, and no additional inhibitory activity was recovered from any other gel slice.

Discussion

An inhibitor in non-proliferating cells was identified that prevents activation of complexes containing the G1 cyclin, cyclin E (Koff et al. (1991); Lew et al. (1991); Ohtsubo & Roberts (1993)), and its catalytic subunit, Cdk2 (Koff et al. (1992); Dulic et al. (1992)). This inhibitory activity is at least in part attributable to a 27 kDa polypeptide, which has also been named $p27^{KiP1}$ (Cdk inhibitory protein 1). The inhibitor and $p27^{KiP1}$ share the following characteristics: they bind to cyclin E-Cdk2 complexes but not to Cdk2 alone; they are only detected in extracts from growth arrested cells; they can be sequestered by cyclin D2-Cdk4 complexes but not by either component alone; they are heat stable; they are latent in extracts of proliferating cells but can be unmasked by brief heat treatment. In addition purified $p27^{KiP1}$ inhibits Cdk2 activation by cyclin E when added to an extract from proliferating cells. While these data strongly suggest that $p27^{KiP1}$ is at least a component of the Cdk2 inhibitor, it has not been determined whether inhibition is due to $p27^{KiP1}$ alone, or whether $p27^{KiP1}$ recruits additional proteins to the cyclin E-Cdk2 complex. It has further been determined that p27, as well as cyclin E and Cdk2, are present in other organisms, i.e., mice and humans (data not shown).

The mechanism of $p27^{KiP1}$ inhibition has features that distinguish it from pathways that control activation of the mitotic cyclin cyclin-Cdc2 complexes, First $p27^{KiP1}$ appears to act stoichiometrically rather than catalytically. Second, tyrosine phosphorylation of Cdk2 ws not detected in inactive cyclin E-Cdk2 complexes containing $p27^{KiP1}$, suggesting that $p27^{KiP1}$ does not have tyrosine kinase activity or inhibit a tyrosine phosphatase. Complexes containing $p27^{KiP1}$ were not efficiently phosphorylated by the p34Cdc2 activating kinase, CAK, and this might be sufficient to explain their inactivity. It is possible that $p27^{KiP1}$ dephosphorylates Thr160, although it would be surprising if the enzymatic activity of a phosphatase were stable to heating to 100° C. It is more likely that binding of $p27^{KiP1}$ to the cyclin E-Cdk2 complex prevents Thr160 phosphorylation by altering the conformation of the T160 domain, or by sterically obstructing CAK. It would not be surprising if $p27^{KiP1}$ functioned similarly to the negative regulatory subunits or domains of other protein kinases, perhaps even interacting with the kinase active site as a pseudosubstrate.

It is intriguing that in addition to $p27^{KiP1}$, other potential regulators of Cdk activity during G1 also bind directly to cyclin-Cdk complexes, including FAR1 (Peter et al. (1993)), p40 (Mendenhall (1993)), p16 and p21 (Xiong et al. (1992); (1993)) and Rb (Kato et al. (1993) supra; Dowdy et al. (1993) supra; Ewen et al., (1993a) supra). While none of these other proteins has yet been shown to directly inhibit Cdk activity, it seems likely that at least some of them will perform this function. Direct protein-protein interactions may be a way to focus inhibitory signals on specific cyclin-Cdk complexes in a cellular environment containing other more promiscuous transacting regulators of Cdk activity.

$p27^{KiP1}$ Links Growth Inhibitory Signals to Cell Cycle Arrest $p27^{KiP1}$ was discovered in cells arrested in G1 by either contact inhibition or TGF-β. A similar activity has also been found to block Cdk2 activation in various cell types deprived of specific growth factors, including serum-starved fibroblasts and IL-2 deprived lymphocytes (unpublished observations). Inhibition of Cdk2 activation by $p27^{KiP1}$ or functionally similar proteins, may be a general mechanism through which diverse extracellular and intracellular signals exert control on cell proliferation.

$p27^{KiP1}$ constrains cell proliferation by setting the threshold level of cyclin E necessary to activate Cdk2. If $p27^{KiP1}$ acts stoichiometrically, as these data suggest, then the Cdk2 activation threshold is reached soon after the amount of cyclin E in the cell exceeds the amount of active $p27^{KiP1}$. In arrested cells this threshold is set higher than physiological cyclin E levels, and consequently only inactive cyclin E-Cdk2 complexes assemble. The cyclin A-Cdk2 complex may be subject to similar control (Koff et al. (1993) supra; Firpo et al., in preparation), and an inability to activate this complex should also contribute to cell cycle arrest (Girard F. et al. (1991) *Cell* 67:1169–1179; PacJano et al. (1992), (1993); Tsai et al. (1993)).

How might growth inhibitory signals be linked to the activity of $p27^{KiP11}$? The simplest idea would be that growing cells do not contain much $p27^{KiP1}$ and that signals which inhibit cell proliferation induce $p27^{KiP1}$ synthesis or stabilization and thereby increase its amount above a critical basal level. This model can not be strictly correct because greatly increased quantities of $p27^{KiP1}$ can be recovered from a latent pool once extracts from proliferating cells are subject to heat treatment. A substantial pool of $p27^{KiP1}$ must be present in these extracts and must be seuquestered by other molecules. This implies that $p27^{KiP1}$ plays a normal role during the proliferative cell cycle and is not simply a response element for signals which induce growth arrest. The abundance of "free" $p27^{KiP1}$ that is able to interact with the cyclin E-Cdk2 complex might, therefore, be modulated by and upstream regulator such as the cyclin D2-Cdk4 complex, which also binds to $p27^{KiP1}$ directly. This prevents association with cyclin E-Cdk2 and enables its functional activation, at least in vitro. The idea that p27 activity is governed by an upstream regulator does not exclude the possibility that the total cellular level of p27 may increase in arrested cells, and these experiments have not directly compared the total amounts of p27 in proliferating and arrested cells.

D-type cyclins are themselves targets of growth inhibitory signals (reviewed in Sherr (1993)). Their synthesis is rapidly reduced in growth factor-deprived cells (Matsushime et al. (1991) supra; Won et al. (1992); Kato et al., in press) and in contact inhibited cells (unpublished observations) leading to a reduction in cyclin D-Cdk4 levels (Matsushime et al. (1992) supra). While D-type cyclin levels are not greatly affected by TGF-β blockade, TGF-β does reduce synthesis of Cdk4 so that a net reduction in cyclin D-Cdk4 complexes is achieved nevertheless (Ewen et al. (1993b) supra). In TGF-β inhibited cells where Cdk4 is limiting, expression of excess Cdk4 should lead to the formation of additional cyclin D-Cdk4 complexes and sequester $p27^{KiP1}$. In fact, enforced expression of Cdk4 in vivo reverses the block to Cdk2 activation in cells exposed to TGF-β (Ewen et al. (1993b) supra). However, the addition of Cdk4 alone to extracts from TGF-β treated cells in vitro does not reverse the interaction of $p27^{KiP1}$ with cyclin E-Cdk2. Unlike complexes with cyclin E and Cdk2, which can be formed in vitro by mixing the recombinant proteins produced in insect cells, D-type cyclins and Cdk4 do not assemble efficiently unless Sf9 cells are coinfected with baculoviruses encoding both components (Kato et al. (1993) supra). Although the reasons underlying these differences in complex formation have not been defined, all results are internally consistent and support the idea that cyclin D-Cdk4 complexes act upstream of cyclin E-Cdk2 by interacting with $p27^{KiP1}$. Although these ideas are based upon many observations made in intact cells, the proposed pathway containing cyclin D-Cdk4, $p27^{KiP1}$ and cyclin E-Cdk2 has been tested directly only in vitro. One might expect that Cdk2 will be regulated by additional mechanisms, and that other novel Cdk complexes in addition to cyclin D2-Cdk4 could contribute to the titration of $p27^{KiP1}$.

It is not likely that the only role of cyclin D2-Cdk4 is to titrate $p27^{KiP1}$, but rather, complex accumulation is likely to trigger the Cdk4-mediated phosphorylation of particular substrates necessary for G1 progression. Thus cyclin D complexed with catalytically inactive Cdk4 is sufficient to sequester $p27^{KiP1}$, but is unlikely to fully substitute for all essential Cdk4 functions in vivo.

One feature of $p27^{KiP1}$ induced cell cycle arrest is that cells can accumulate inactive cyclin E-Cdk2 complexes. Recovery from cell cycle arrest, therefore, might not require synthesis of new cyclin E and assembly of new cyclin E-Cdk2 complexes. Rather the cell may make use of this latent pool of inactive complexes when cell proliferation resumes. This might be essential under circumstances where the signals that promoted cyclin synthesis were transient, and absent when the growth inhibitory signals ceased. Thus far, however, conditions have not been defined that allow reactivation of inactive cyclin E-Cdk2$p27^{KiP1}$ complexes. In vitro, only cyclin E-Cdk2 complexes which assemble after titration of $p27^{KiP1}$ are active, and the same may be true in vivo as well.

The presence of $p27^{KiP1}$ in proliferating cells suggests that its role may not be restricted to inducing cell cycle arrest in response to extracellular signals. It may also set the cyclin E threshold for execution of the G1 to S transition during each mitotic cycle. Cell fusion experiments have indicated that entry into S phase in mammalian fibroblasts is controlled by an activator that accumulates continuously during G1 (Foumier and Pardee (1975); Rao et al. (1977)). By comparing the rate of S phase entry in mono- bi- and tri-nucleate cells it was concluded that the amount of this activator rather than its concentration was critical in determining the start of S phase. These observations are consistent with a model in which the limiting step in Cdk2 activation is not assembly of the cyclin-Cdk2 complex, which should be concentration dependent, but instead involves the assembly of a sufficient number of complexes to overcome a threshold level of a stoichiometric inhibitor, such as $p27^{KiP1}$. It is also pointed out that spontaneous decay of $p27^{KiP1}$ inhibited complexes to free $p27^{KiP1}$ and active cyclin-Cdk2 might occur with first order (exponential) kinetics and could underlie the first order rate constants frequently reported for S phase entry in mammalian cells (Smith & Martin (1973); Brooks R. et al. (1980) *Cell* 19:493–504).

$p27^{KiP1}$ May Enforce Order during G1 Progression

Cyclin-Cdk complexes appear in a specific order as cells transit G1 (Sherr (1993) supra). If it is assumed that this temporal order is essential for normal G1 progression, then cells must solve the problem of restoring order during recovery from cell cycle arrest. For example, contact inhibition and TGF-β interfere with the accumulation of cyclin D-Cdk4 complexes, but do not affect synthesis of cyclin E- and cyclin A-Cdk2 complexes, which act later in the cell cycle. If the cyclin E-Cdk2 and cyclin A-Cdk2 complexes were active during cell cycle arrest, then the normal order of Cdk action would be lost. $p27^{KiP1}$ might ensure that this does not happen by preventing activation of these pre-existing complexes during cell cycle arrest. In addition, if the activity of $p27^{KiP1}$ is itself controlled by cyclin D2-Cdk4, then this would provide an efficient mechanism for maintaining Cdk2 inactive until cyclin D-Cdk4 complexes assemble and execute their functions.

EXAMPLE 2

Epxerimental Procedures

Metabolic Labeling, Immunoprecipitations and Peptide Mapping

MvlLu cells were synchronized by contact inhibition, treated with TGF-β, metabolically labeled, lysed, immunoprecipitated with anti-Cdk2 antibody or chromatographed on cyclin E-Cdk2 affinity columns. For peptide mapping, the 27 kd band present in Cdk2 immunoprecipitates and in the cyclin E-Cdk2 affinity column eluates was cut out from the gels, digested with 0.1 μg of V8 protease, and resolved on 15–22.5% gradient gels.

Baculoviral Proteins

The human cyclin E cDNA (Koff et al. (1991) supra) was tagged at the N-terminus with a hexahistidine sequence. This cDNA was cloned into baculovirus transfer vector pVL1392, and expressed in Sf9 cells as described in the BaculoGold Transfection Kit (Pharmingen). Baculoviral proteins were prepared by the method of Desai et al. (1992) supra).

Kip1 Purification

Two hundred 150 mm dishes of contact inhibited MvlLu cells (~2×10$^{10}$ cells) were collected by trypsinization and lysed in hypotonic buffer by sonication. The extracts were clarified by centrifugation, heated to 100° C. for 5 min and clarified by centrifugation. Agarose-precleared extracts were allowed to bind to His-cyclin E-Cdk2 complexes immobilized on Ni++-NTA-agarose. Specifically bound proteins were eluted with 6M guanidium hydrochloride solution, dialyzed overnight against 1×HBB buffer (25 mM HEPES-KOH, pH 7.7, 150 mM NaCl, 5 mM MgCl$_2$, 0.05% NP-40 and 1 mM DTT) (Kaelin Jr. et al. (1992)) and acetone-precipitated.

Protein Sequence Analysis

Protein was fractionated by SDS-PAGE, electroblotted onto nitrocellulose, and the Ponceau S-stained 27 kDa band was excised and processed for internal amino acid sequence analysis (Tempst et al. (1990)). HPLC peak fractions (over trypsin background) were analyzed by a combination of automated Edman degradation and matrix-assisted laser-desorption (MALDI-TOF) mass spectrometry. Mass analysis (on 2% aliquots) was carried out using a model LaserTec Research MALDI-TOF instrument (Vestec), and a-cyano-4-hydroxy cinnamic acid as the matrix. Chemical sequencing (on 95% of the sample) was done using an Applied Biosystems 477A sequenator optimized for femtomole level analysis.

Kip1 cDNA Cloning and Northern Blot Analysis

RT-PCR reactions were performed using degenerate oligonucleotides as primers and total RNA from contact inhibited MvlLu cells as template. The combination of one pair of primers (see FIG. 9A) yielded a 135 bp fragment that was used to screen a lZAPII cDNA library prepared from MvlLu cells. The mouse Kip1 cDNA was obtained from a lEXlox mouse embryo cDNA library (Novagen), and the human Kip1 cDNA was obtained from a lgh11 kidney cDNA library (Clontech). Poly(A)+ RNA blots were hybridized with a PCR-derived fragment of the mouse Kip1 cDNA labeled by random priming.

In vitro Translation

A NdeI-XhoI fragment containing the coding region of the mouse Kip1 cDNA (nucleotides 1–591) was subcloned to pCITE2a (Novagen). This construct hexahistidine sequence and 6 amino acids from the vector at the N-terminus of Kip1. In vitro transcription and translation were performed using Red Nova lystate (Novagen).

Recombinant Kip1

A 591 bp PCR generated NheI-XhoI fragment of the mouse Kip1 cDNA containing the full length coding region was subloned into pET21a (Novagen), yielding a construct that encodes Kip1 with a C-terminal hexahistidine sequence. The protein was expressed in BL21 (DE3) bacteria and purified by sonicating cells in a solution containing 8M urea, 50 mM Tris-HCl (pH 7.4), 20 mM imidazole, clarified by centrifugation and bound to Ni++-NTA agarose for 1 h at 4° C. The column was washed with a 6M to 0.75 M urea reverse gradient in 0.5M sodium chloride, 50 mM Tris (pH 7.4), and 20% glycerol and eluted with 200 mM imidazole, 20 mM HEPES pH 7.4, 1M KCl, 100 mM EDTA. The eluate was dialysed overnight against 1×HBB buffer and stored at −80° C. until use.

In vitro Kinase and Cdk2 Activation Assays

H5 insect cell extracts containing baculovirally-expressed cyclins and Cdks were incubated with recombinant Kip1 for 30 min at 37° C., precipitated with anti-HA antibody, and the histone H1 kinase activity of these complexes was assayed (Koff et al. (1993) supra). Rb kinase reactions were done according to Matsushime et al. (1991, supra). The phosphorylation of the histone H1 band and Rb band were quantitated with Phosphorimager (Molecular Dynamics).

Hypotonic cell extracts from exponentially growing A549 cells were incubated with baculoviral His-cyclin E protein, with or without Kip1, at 37° C. for 30 min. Mixtures were then diluted 10-fold in 1×NP40 RIPA buffer containing 20 mM imidazole and incubated with Ni++-NTA-agarose at 4° C. for 1 h. One portion of the samples was run on 12% SDS-PAGE, and immunoblotted with anti-Cdk2 antibody (Koff et al. (1993) supra).

Kip1 Transfections and Flow Cytometry Analysis

The mouse Kip1 cDNA (nucleotides −82 to +591) was subcloned into pCMV5 (Attisano et al. (1993) *Cell* 75:671–680). R-1B cells were cotransfected with 0.5 μg/ml of pCEXV-3 containing murine CD16 cDNA (Kurosaki and Ravetch (1989)) and 3 μg/ml of pCMV5 alone, or with 3 μg/ml of pCMV5-Kip1 (Attisano et al. (1993) supra). CD16 immunostained cells (Wirthmueller et al. (1992)) were analyzed by flow cytometry using FACScan (Becton-Dickinson) and Multicycle software (PHOENIX Flow Systems).

Results

Purification and Cloning of Kip1

Lysates from contact inhibited MvlLu cells were heated to 100° C., cleared of insoluble material, and allowed to bind to a cyclin E-Cdk2 affinity column. Elution with 6 M guanidium hydrochloride yielded recombinant Cdk2 released from the column, and the 27 kd protein Kip1. Dialyzed aliquots of this sample had strong inhibitory activity towards cyclin E-Cdk2 in histone H1 kinase assays, and this activity was shown to coelute from SDS-PAGE gel slices with Kip1. The Kip1 yield from two separate preparations (~2×10$^{10}$ cells each) was 0.3 μg and 1 μg, respectively.

Figure 8A:
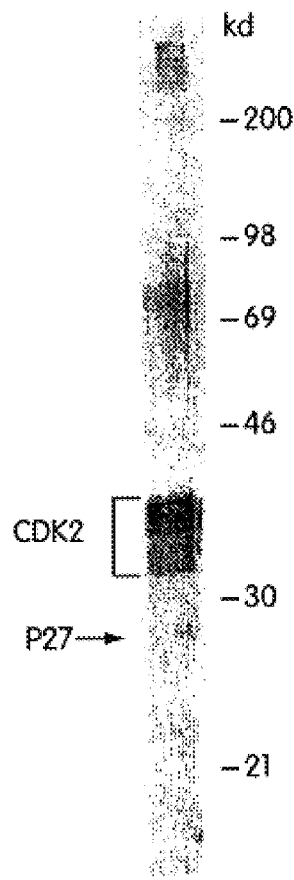
Figure 8B:
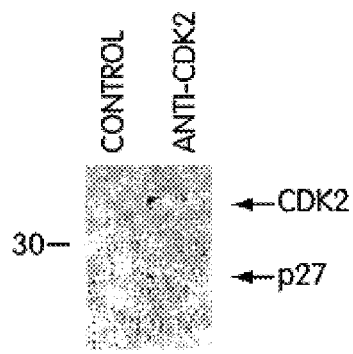
Figure 8C:
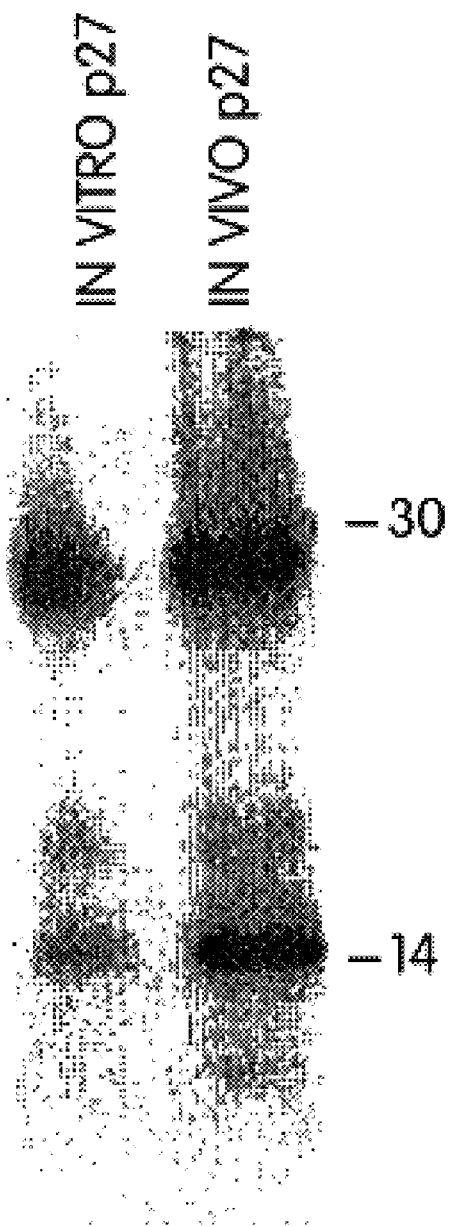

In order to confirm that Kip1 interacts with Cdk2 in vivo, metabolically labeled extracts were immunoprecipitated from contact inhibited MvlLu cells using anti-Cdk2 antibodies (FIG. 8B). In addition to Cdk2, the precipitate contained a 27 kd band whose peptide map, after limited digestion with V8 protease, was identical to that of Kip1 purified from metabolically-labeled cells by cyclin E-Cdk2 affinity chromatography (FIG. 8C). These results provided further evidence that the Cdk inhibitor purified by binding to cyclin E-Cdk2 in vitro was associated with Cdk2 in quiescent cells.

Various Kip1 tryptic peptide sequences were obtained by automated Edman degradation and used to design degenerate oligonucleotide primers for cDNA amplification by the reverse transcription-polymerase chain reaction (RT-PCR). A PCR product amplified out of reverse-transcribed MvlLu mRNA was used to screen a MvlLu cDNA library. This yielded one single positive clone that encoded the sequences obtained from the purified protein (FIG. 9A). Screening of cDNA libraries from human kidney and mouse embryo with the Kip1 cDNA yielded clones of highly related sequence. The human and mouse Kip1 cDNAs (Genbank Accession Numbers U10906 and U09968) had open reading frames of 594 and 591 bp, respectively, starting with an ATG codon in a favorable translation initiation context and preceded by stop codons (data not shown). Compared to these open reading frames, the mink clone (Genbank Accession Number U09966) was incomplete, and ended at nucleotide 534 (FIG. 9A).

The Kip1 cDNA encodes a predicted protein of 198 amino acids (22,257 daltons) in human and 197 amino acids (22,208 daltons) in mouse. These values are smaller than the 27 kd value obtained with the purified mink protein by SDS-PAGE. To resolve this discrepancy, a cDNA encoding the mouse Kip1 sequence was constructed, and tagged at the C-terminus with a hexahistidine sequence (~1 kd mass). In vitro transcription and translation of this c DNA yielded a product that bound specifically to Ni++-NTA-agarose and migrated as a 28 kd protein on SDS-PAGE gels (FIG. 8C), confirming that the cloned cDNA encodes full-length Kip1 and that this protein migrates on SDS-PAGE somewhat slower than its calculated molecular mass.

Kip1 is Highly Conserved and Related to Cip1/WAF1

The predicted human, mouse and mink Kip1 amino acid sequences are highly related, showing ~90% identity (FIG. 9A). A Genbank search revealed that, at the amino acid level, Kip1 shows significant homology only to Cip1/WAF1. The similarity was largely limited to a 60-amino acid segment in the N-terminal half of the protein. This region was 44% identical to the corresponding region in Cip1/WAF1 (FIG. 9B). Like Cip1/WAF1, Kip1 has a putative bipartite nuclear localization signal (Dingwall C. and Laskey R. A. (1991) *Trends Biochem. Sci.* 16:478–481) near the C-terminus (FIG. 9B). Yet unlike Cip1/WAF1, the Kip1 sequence does not have a putative zinc finger motif in the N-terminal region, and has a C-terminal extension of 23 amino acids that contains a consensus Cdc2 phosphorylation site (FIG. 9B).

Cdk Inhibitory Activity

Figure 10A:
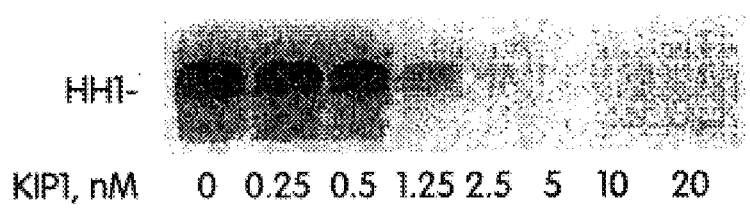
Figure 10B:
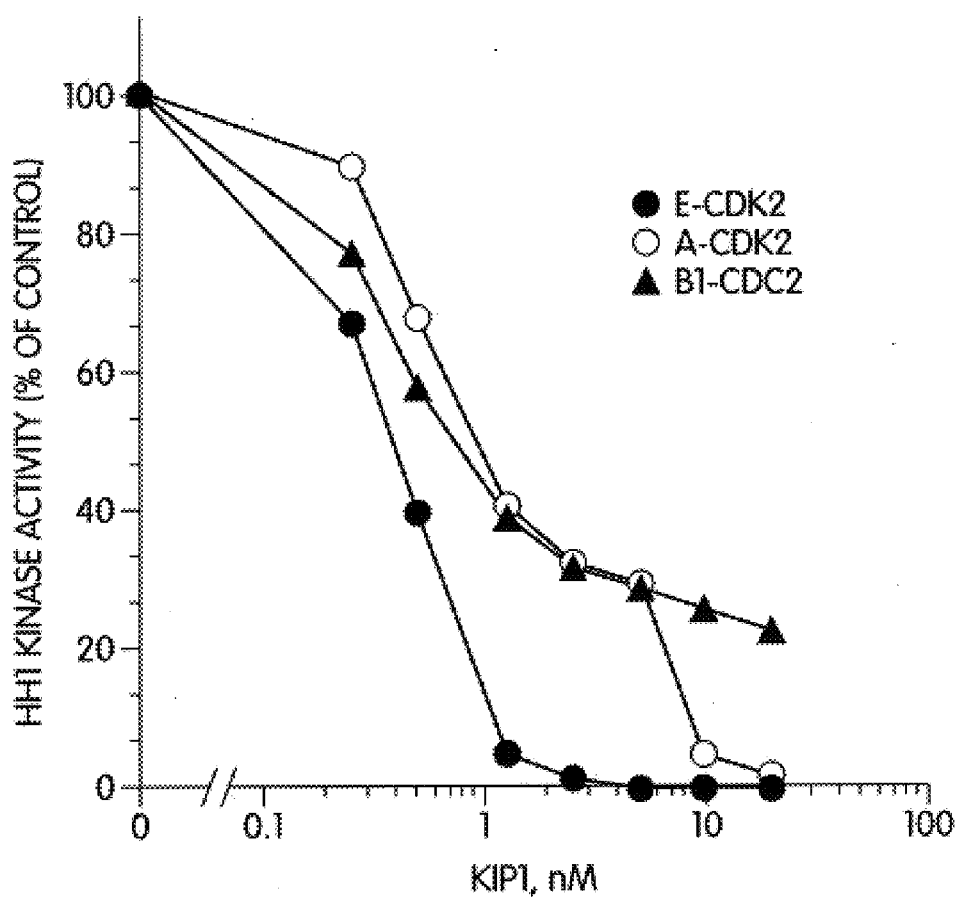
Figure 10C:
Figure 10D:
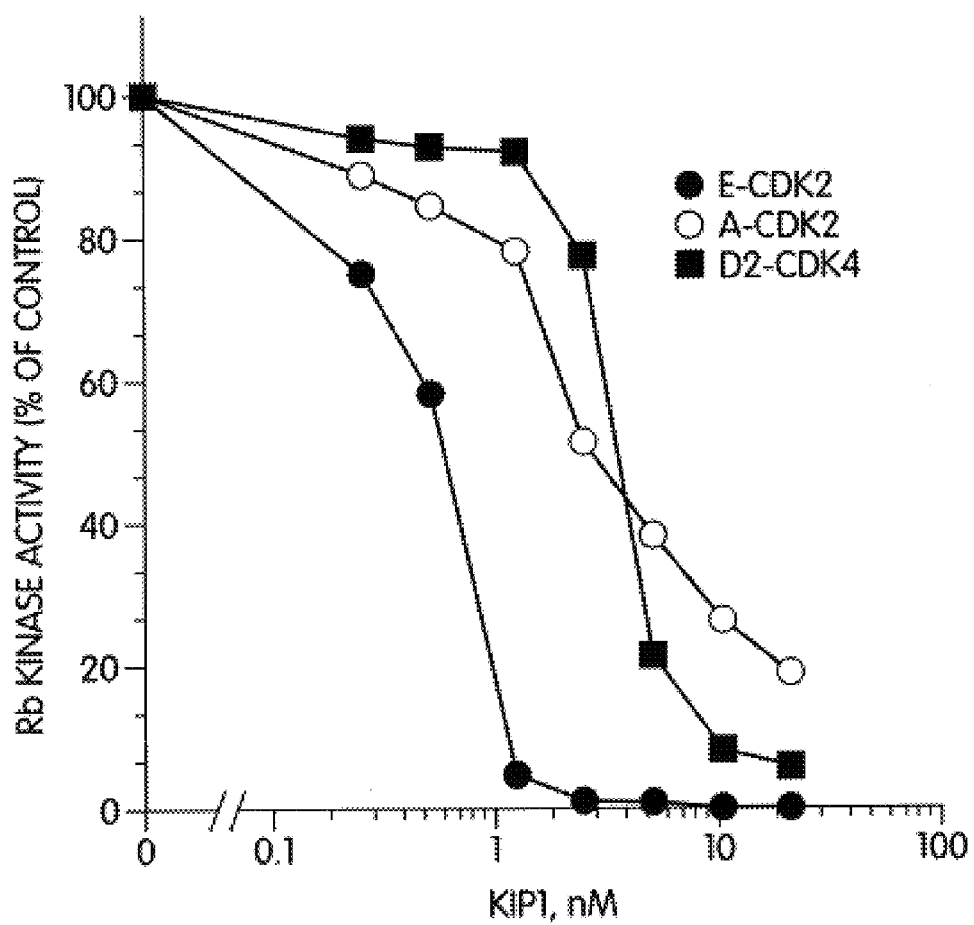

Pure recombinant Kip1 tagged with hexahistidine at the C-terminus inhibited the histone H1 kinase activity of human cyclin A-Cdk2, cyclin E-Cdk2 and cyclin B1-Cdc2 complexes when assayed under linear reaction conditions (FIGS. 10A and 10B) whereas a mock sample from bacteria transformed with vector alone did not. Cyclin E-Cdk2 was inhibited half-maximally at 0.5 nM Kip1 (FIG. 10B). Complete inhibition of cyclin A-Cdk2 required an eight-fold higher concentration, and this concentration was not sufficient to completely block cyclin B1-Cdc2 (FIG. 10B). Addition of Kip1 to cyclin E-Cdk2, cyclin A-Cdk2 or cyclin D2-Cdk4 complexes inhibited their ability to phosphorylate a GST-Rb fusion product (FIGS. 10C and D). The relative sensitivity of cyclin E-Cdk2 and cyclin A-Cdk2 to inhibition by Kip1 in these assays paralleled their sensitivity in the histone H1 kinase assays, but the actual concentration of cyclin:Cdk complexes is not known.

Cdk Inhibitory Domain

Figure 10E:
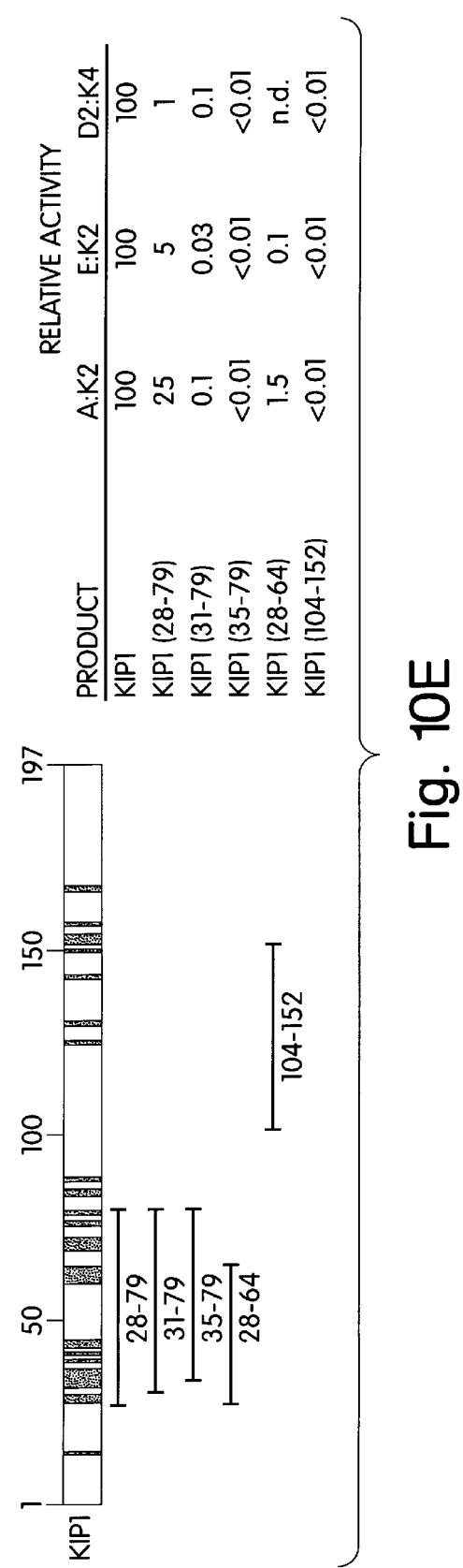

It was investigated whether the inhibitory activity if Kip1 resided in the region of similarity to Cip1/WAF1. A 52-amino acid peptide [Kip1 (28–79)] corresponding to this region in Kip1 (FIG. 10E) was produced recombinantly and purified with a C-terminal hexahistidine tag. This peptide inhibited Rb phosphorylation by cyclin A-Cdk2 with a potency that was close to that of full length Kip1 (FIG. 10E) and inhibited cyclin E-Cdk2 or cyclin D2:Cdk4 less effectively. Versions of this Kip1 region missing three amino acids at the N-terminus or fifteen at the C-terminus, were much weaker as Cdk inhibitors, and deletion of seven N-terminal amino acids yielded a product with no inhibitory activity (FIG. 10E). The peptide Kip1[(104–152)] which has little sequence similarity to Cip1/WAF1, was inactive as a Cdk inhibitor (FIG. 10E).

Kip1 Prevents Cdk2 Activation

Kip1 was originally identified as a factor whose presence in extracts from quiescent cells rendered Cdk2 refractory to activation by phosphorylation at Thr160. In order to determine if Kip1 could block Cdk activation, its effect on cyclin E-dependent Cdk2 activation in extracts from exponentially growing cells was assayed (Koff et al. (1993) supra). A549 human lung carcinoma cell extracts were incubated with histidine-tagged cyclin E which was then retrieved and assayed for associated histone H1 kinase activity (FIG. 11A). Addition of histidine-tagged Kip1 to the cell extracts markedly decreased the level of cyclin E-associated kinase activity (FIG. 11A). In parallel assays, the retrieved cyclin E was subjected to SDS-PAGE and western blotting with anti-Cdk2 antibodies. Cell extracts that did not receive Kip1 yielded cyclin E-associated Cdk2 in a form that corresponds to Cdk2 phosphorylated at Thr160 (Gu et al. (1992) supra) (FIG. 11B). In contrast, cyclin E-associated Cdk2 from extracts that received Kip1 was exclusively in the inactive form (FIG. 11B). Collectively, these results suggested that Kip1 binding to preactive cyclin E-Cdk1 complexes in vitro prevented Thr160 phosphorylation and activation of Cdk2.

Kip 1 Overexpression Inhibits Cell Entry into S Phase

Mouse Kip1 subcloned into a mammalian expression vector was transfected into MvlLu cells under conditions in which up to 65% of the cell population takes up and transiently expresses transfected plasmids (Attisano et al. (1993) supra). The rate of $^{125}$I-deoxyuridine incorporation into DNA was reduced 70% in cells transfected with Kip1 compared to cells transfected with vector alone (Table III).

TABLE III

Kip1 blocks entry into S phase

| Time after CD16+ transfection | Vector | $^{125}$I-deoxyuridine incorporation$_a$ | Percentage of cells in S phase$_b$ |
| --- | --- | --- | --- |
| 24 h | pCMV5 | 27,581 ± 5,126 | 26 ± 5 |
| | pCMV5-Kip1 | 8,386 ± 1,250 | 9 ± 2 |
| 43 h | pCMV5 | 5,126 ± 47 | 35 ± 2 |
| | pCMV5-Kip1 | 1,510 ± 140 | 7 ± 1 |

The TGF-β receptor-defective R-1B cell line was cotransfected with a human CD16 expression vector and pCMV5 or pCMV5 containing the mouse Kip1 cDNA. Assays were conducted at the indicated times after transfection. (a) $^{125}$1I-deoxyuridine incorporated over a 3 h period by the entire cell population. Data are the average±S.D. of triplicate determinations. (b) Transfected cells were immunostained with anti-CD16 and analyzed for DNA content. Data are the average of two separate experiments, and show the range of values.

To determine the effect on cell cycle distribution, Kip1 was cotransfected with a CD16 expression vector (Kurosaki and Ravetch (1989)) that allowed flow cytometric separation of the transfected cells based on CD16 immunofluorescence. The CD16+ population cotransfected with Kip1 showed a larger proportion of cells in G1 phase and a smaller proportion in S phase than the CD16+ population cotransfected with vector alone (Table III), suggesting that Kip1 overexpression obstructed cell entry into S phase. Cell numbers after transfection indicated that Kip1 did not cause cell death (data not shown).

Kip1 mRNA Distribution and Levels in Quiescent and Proliferating Cells

The level of endogenous Kip1 mRNA expression in various human tissues was determined by Northern blot analysis. The only mRNA detected was a species of 2.5 kb present at similar levels in all tissues tested, although it was somewhat higher in skeletal muscle and lower in liver and kidney (FIG. 12A). Kip1 mRNA levels were similar in exponentially proliferating and contact inhibited MvlLu cells, and did not change when cells were released from contact inhibition by being plated at low density in the presence of serum (FIG. 12B). Addition of TGF-β to cells released from contact inhibition also did not affect Kip1 mRNA levels (FIG. 12B). These results indicate that the regulation of Kip1 by extracellular antiproliferative signals occurs at a post-transcriptional level.

Discussion

A Family of Cdk Inhibitors

Human Kip1 encodes a protein of 198 amino acids that is highly conserved (~90% identity) in mouse and mink. Its most distinctive feature is a 60-amino acid region in the N-terminal half that has amino acid sequence similarity to Cip1/WAF1 (El-Deiry W. S. et al. (1993) Cell 75:817–825; Harper et al. (1993); Xiong et al. (1993) supra). Like Cip1/WAF1, Kip1 contains a potential nuclear localization signal in the C-terminal region. In Kip1, this region also contains a consensus Cdc2 kinase site that might play a role in feedback regulation by their target kinases.

The structural similarity between Kip1 and Cip1/WAF1 defines a family of mammalian Cdk inhibitors with different regulatory properties. Kip1 is involved post-transcriptionally in the action of extracellular signals (present work) and its silencing in exponentially growing cells correlates with binding to a heat-labile component. In contrast, Cip1/WAF1 is regulated transcriptionally by p53, senescence and cell quiescence. Kip1 and Cip1/WAF1 are more effective against G1 Cdks than against mitotic Cdks. However, Kip1 was more effective against cyclin E-Cdk2 than against cyclin A-Cdk2 (or cyclin D2-Cdk4) whereas in similar assays, Cip1/WAF1 was more effective against cyclin A-Cdk2 (Harper et al. (1993) supra). Kip1 effectiveness is likely defined by its binding affinity for a given cyclin-Cdk complex.

The Kip1 region that is similar to Cip1/WAF1 is sufficient to inhibit Cdk activity when tested as a 52-amino acid peptide in vitro. This 52-amino acid segment contains the sequence LFGPVN which corresponds to the longest uninterrupted stretch of identity to Cip1/WAF1 and, interestingly, is similar to the FAR1 sequence LSQPVN located in a region required for interaction with CLN2-CDC28 (Peter et al. (1993) supra).

Cdk Inhibition at Two Levels

Kip1 can inhibit both the process of Cdk activation and the kinase activity of cyclin-Cdk complexes assembled and activated in intact cells. Kip1 was originally identified as a factor whose presence in extracts of quiescent cells rendered them unable to activate Cdk2 by phosphrylation at $Thr^{160}$. Indeed, recombinant Kip1 inhibits Cdk2 $Thr^{160}$ phosphorylation and activation in vitro. Although Kip1 could act as an inhibitor of the Cdk-activating kinase, previous results tend to argue against this possibility. The dual effects of Kip1, both on Cdk2 activation and Cdk2 activity, might relate to the fact that $Thr^{160}$ is located in a loop that closes the substrate-binding cleft in the Cdk2 structure (DeBondt H. L. et al. (1993) Nature 363:595–602). It is conceivable that binding of Kip1 to this region might interfere with $Thr^{160}$ phosphorylation as well as with the catalytic function of activated Cdk2.

Function in the Cell Cycle

Cyclin E-Cdk2 and cyclin D-Cdk4 are rate limiting for G1 progression (Jiang et al. (1993); Ohtsubo and Roberts (1993); Quelle et al. (1993)). Inhibition of these kinases by Kip1 in vivo would render cells unable to reach that transition. The strong reductions in the rate of DNA synthesis and the proportion of cells in S phase caused by Kip1 transfection are consistent with this possibility and with a role of Kip1 as mediator of extracellular growth inhibitory signals.

As cells released from contact inhibition move closer to S phase, their extracts contain progressively lower levels of Kip1 activity, and this decline can be prevented by TGF-β addition early in G1 phase. However, the present results show that contact inhibited cells and TGF-β-treated cells have Kip1 mRNA levels equal to those of proliferating cells. Furthermore, extracts from proliferating cells yield active Kip1 when they are heated transiently at 100° C. One interpretation of these observations is that Kip1 is progressively sequestered by binding to a heat-labile component as cells progress through G1, and this process can be prevented by TGF-β. Mitogens and antimitogens might regulate Kip1 activity or availability by controlling its binding to a silencing protein. Alternatively, Kip1 might be a passive regulator whose uniform levels could ensure that active Cdks become available only when their levels reach the threshold imposed by binding to Kip1. In the latter situation, even small effects of mitogens and antimitogens on cyclin or Cdk protein levels could become amplified by the existence of that threshold.

EXAMPLE 3

Introduction

Mutations in genes that regulate the cell cycle are found in the majority of human cancers[1]. However, there is a subset of cell cycle genes, including those encoding cyclin E, a G1 cyclin, and p27Kip1, a CDK inhibitor, in which mutations are uncommon [2–5] although there is evidence that the proteins encoded by these genes contribute to tumor progression [6–12]. Expression of these proteins can be largely controlled by post-transcriptional mechanisms, suggesting that the levels of p27 and cyclin E protein in tumor cells may be a more accurate measure of their importance in tumorigenesis. [1, 13, 14]. We undertook an immunohistochemical analysis of p27 and cyclin E protein expression in breast ductal carcinomas, and found that high levels of cyclin E (p=0.03) and low levels of p27 (p=0.01) were strongly predictive of increased mortality, both before and after adjustment for other clinical and pathological characteristics. Most dramatically, when the cyclin E and p27 indices were combined, the relative risk of mortality in those patients with low p27 and high cyclin E expression was almost 9 (p<0.001). This enabled us to subdivide women with localized, node-negative disease into groups with either significantly elevated or reduced risk of mortality, and suggested that these indices may be useful in determining which patients would benefit from more aggressive therapy.

Cyclin E and p27 are two key regulators of the G1 to S-phase cell cycle transition. Cyclin E is a late G1 cyclin, which along with its catalytic subunit, the protein kinase CDK2, is required for entry into S-phase of the cell cycle [15, 16]. p27 is a member of the Cip/Kip family of CDK inhibitors (CKIs), which includes the p21, p27 and p57 proteins. p27 is present in high levels in quiescent cells, and declines in response to mitogenic signals (such as growth factors and cytokines) in proliferating cells [17–19].

We characterized the expression of cyclin E and p27 in breast tumors from a group of 278 young women. Levels of expression were compared to other tumor characteristics and risk factors (FIG. 17) and to mortality after a median follow-up of 5.2 years. We estimated the relative risks (RR) (both univariate and multivariate) of dying and 95% confidence intervals (CI) using a weighted Cox proportional hazard model, among 237 women for whom information concerning stage, age at diagnosis, tumor size, lymph node status, histologic grade and assays of cyclin E, p27, Ki-67 proliferation index, p53, and c-erbB-2 were available. Positive lymph nodes, large tumor size, intermediate and high histologic grade, presence of c-erbB-2, high levels of cyclin E, and low or absent p27, were associated with increased risk of death in univariate models (FIG. 17). Only lymph node status, presence of c-erbB-2, high cyclin E levels, and low p27 levels, were associated with decreased survival after adjusting for all other factors (FIG. 17).

Figure 16A:
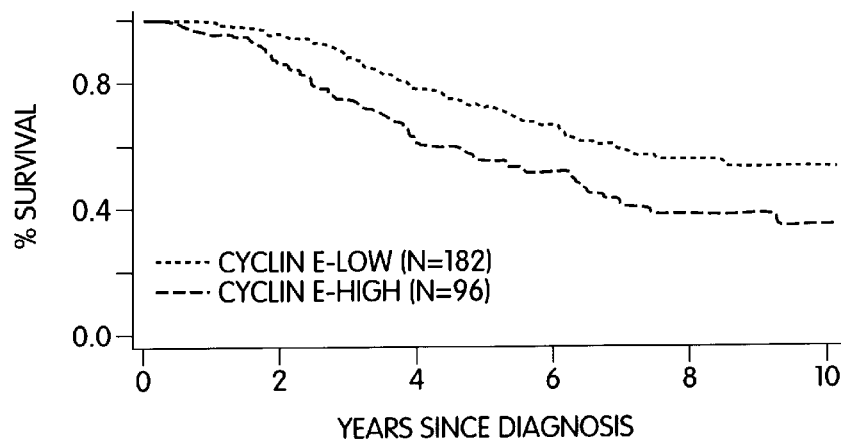
Figure 16B:
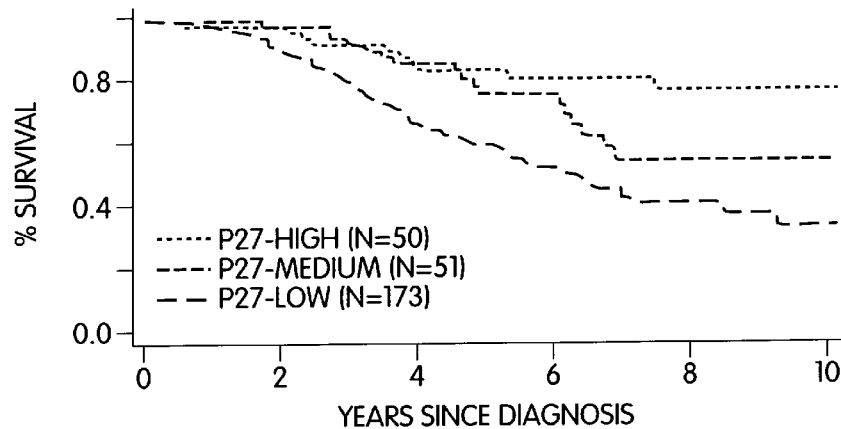

Kaplan-Meier plots of survival show increased mortality risk associated with high levels of cyclin E (RR 2.1, CI 1.3–3.3, p=0.001) (FIG. 16a), and low levels of p27 expression (RR 3.9; CI 2.0–7.5; p=<0.001) (FIG. 16b). The greatest difference in survival was found between women having virtually no p27 and women having the highest levels.

Figure 16C:
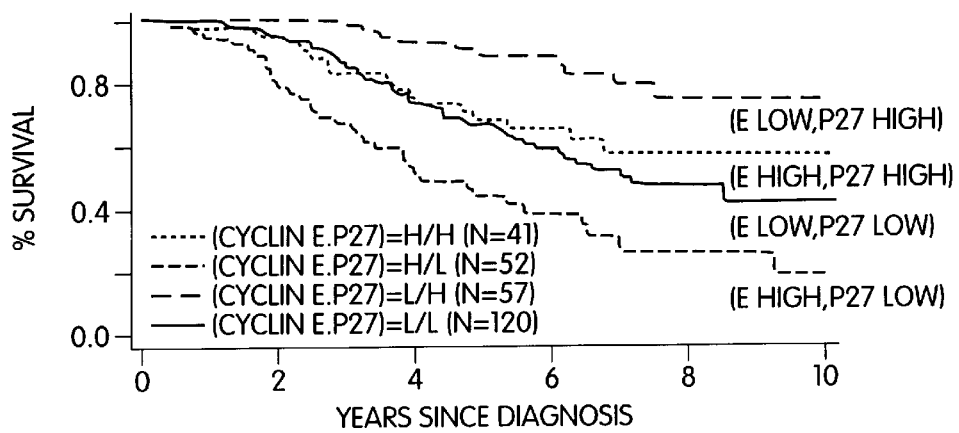
Figure 16D:
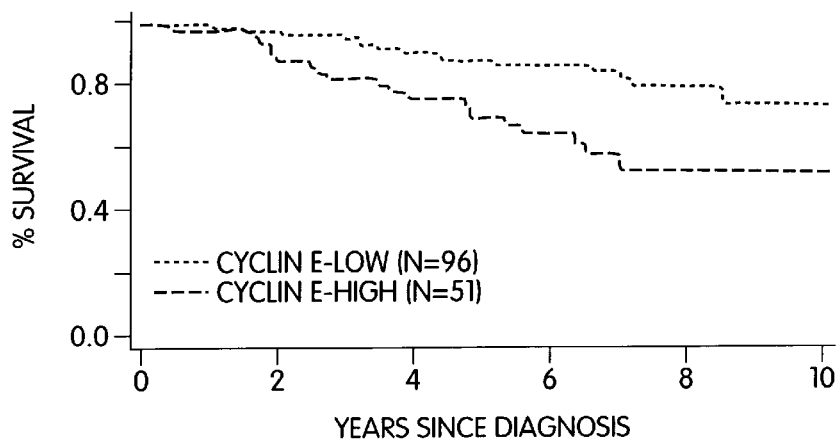
Figure 16E:
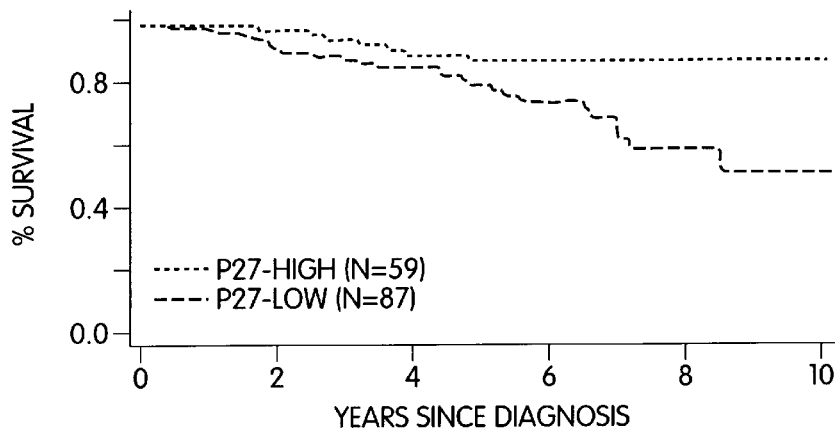
Figure 16F:
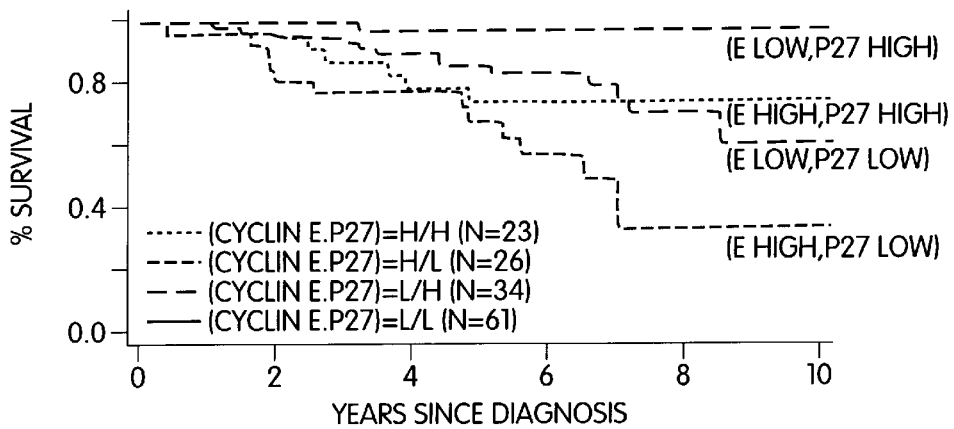

A striking stratification of mortality risk was identified when four different combinations of p27 and cyclin E proteins levels (i.e., both markers at high levels, both markers at low levels, cyclin E high when p27 is low and cyclin E low when p27 is high), were evaluated for their relative effect on survival. The combination of expression that corresponded most closely to normal breast tissue (high p27 and low cyclin E), was associated with the most optimal survival; the opposite pattern (low p27 and high cyclin E), was associated with the highest mortality (RR 8.6; CI 3.6–20.4; p<0.001) (FIG. 16c).

When tumor and clinical characteristics were analyzed according to lymph node status in univariate regression models, large tumor size (RR 10.9, CI 1.4–83.1; p=0.02), presence of c-erbB-2 (RR 3.4, CI 1.4–7.9; p=0.005), presence of p53 protein (RR 2.7, CI 1.2–6.5; p=0.02), high levels of cyclin E (RR 3.3, CI 1.5–7.4; p=0.003), and low or absent p27 (RR 4.1, CI 1.4–12.1; p=0.01), were associated with increased risk of dying in node negative women. In women with lymph node involvement, only the presence of c-erbB-2 (RR 2.4, CI 1.2–4.9; p=0.01), and low or absent p27 (RR 2.6, CI 1.3–5.4; p=0.007) were associated with decreased survival.

Current treatment decisions for individual patients with breast cancer are based on the presence of various prognostic factors. Adjuvant therapy has become the standard of care for the majority of women with axillary node involvement, however, the efficacy in node negative patients is much less certain [20, 21]. Tumor size has been used to stratify patients into prognostic groups, however, almost 50% of node negative women fall into a category of intermediate tumor size with no clear indication for treatment choice [20].

Of the other tumor markers assessed in node negative women, increased S-phase fraction measured by flow cytometry, is one of the more reliable indictors of tumor behavior. Although we found strong overall correlation of Cyclin E expression with proliferation (p<0.001), we identified 27% of tumors in which the Ki-67 index and cyclin E expression levels were not concordant (in contrast to expression of cyclin A which invariably correlated with the proliferative status of the tumor; data not shown). Compared with women whose tumors exhibit low tumor proliferation and low levels of cyclin E, women with discordant cyclin E expression and proliferation, i.e., low Ki-67 index and high cyclin E levels, showed a strong association with mortality (RR 3.3; CI 1.7–6.3; p<0.001). Subsets of tumors or cell lines in which cyclin E expression is unrelated to proliferative rate or phase of the cell cycle have been reported previously and these data support the idea that effects of cell cycle abnormalities are not simply explicable in terms of their effects on cell proliferation [7,22,23].

Our results indicate that the aggressiveness of a tumor can, in part, be described in terms of specific derangements in cell cycle control, but can provide only hints of possible mechanisms underlying abnormal expression of cell cycle proteins. There are many factors that influence expression of cyclin E including mutations in Rb or p16, overexpression of cyclin D1 or E2F, and possibly of most importance, alteration in the degradation pathway of the protein. It may be that the unique utility of assaying cyclin E is that its expression integrates the effects of one or more regulators and thereby provides a single indicator of several possible cell cycle gene mutations. Our finding that p27 and cyclin E are independent prognostic markers indicates that an underlying defect that alters expression of both proteins is unlikely. Cyclin E overexpression and p27 underexpression both result in increased CDK2 activity and it is tempting to postulate that their effect in tumors is because they are independent regulators of the same pathway [10, 24]. However, it is possible the affects of high levels of cyclin E might be due in part or in total to its action in a pathway that does not utilize CDK2. Indeed, the fact that high levels of cyclin E do not necessarily correlate with an increase in cell proliferation leads us to suspect that this alternative explanation may have merit.

Knowing the overall pattern of expression of multiple proteins is likely to be required to gain evidence of a cell's potential for aberrant cell cycle control. The reasons why some important regulators are frequently mutated in tumors, while others are affected through other pathways is not yet clear. But, this suggests that searches for genes mutated in human tumors may miss certain key determinants of tumor aggression which could only have been discovered by examining levels of protein expression. The challenge is to identify a set of cell cycle proteins which are representative of independent regulatory pathways, and thereby establish a collection of markers which together provide the most information about the status of cell cycle controls in individual tumors.

Methods

Patient Population

Paraffin-embedded primary breast tumor tissue samples, obtained prior to any adjuvant treatment, from a subset of a cohort of 1292 women, aged 20 to 44, identified through the Cancer Surveillance System (CSS) of western Washington and interviewed as part of a ongoing study at the Fred Hutchinson Cancer Research Center, diagnosed between 1983 and 1992 were available for this study. Information concerning diagnosis date, tumor size, clinical stage and lymph node status, and deaths was obtained from the CSS. Subjects were followed until the earliest of: their date of death, the date last known to be alive, or the end of the follow-up period. Observations were censored at either the date of last known follow-up or the end date of the follow-up period if death had not occurred.

Compared with women in the entire cohort, the women tested for this study were more likely to have been diagnosed in the early years of the study (40% vs. 57%) and were more likely to have died (53% vs. 87%). A weighted Cox regression analysis accounts for differences in the probability of testing and allows for valid relative risk evaluation (see statistical methods section). Other clinical characteristics (age at diagnosis, stage at diagnosis, lymph node status and tumor size), varied no more than 7% between the two groups.

Tissue Evaluation and Characterization of Antibodies

A total of 278 ductal carcinoma samples were available for study. Tumors were assigned a histologic grade from I (low) to III (high) according to the Bloom and Richardson grading scheme for invasive ductal carcinoma.

Antibodies used for the study included previously characterized affinity purified polyclonal cyclin E[24], cyclin A (Roberts lab) and p27[18]; rabbit polyclonal anti-c-erbB-2 (Dako, Denmark); anti-p53 clone 1801 (Oncogene Science, Uniondale N.Y.); anti-Ki-67 clone MIB-1 (Immunotech, Westbrook Me.). Experimental validation of immunostaining with anti-cyclin E antibody was done by constructing cell lines that overexpress cyclin E from a transfected gene. Cyclin E immunostaining was compared with western blotting and a direct correspondence between the intensity of cyclin E immunostaining was established[25]. Tissues from p27 null mice[10] provided negative control for the p27 antibody; in the absence of p27, there is no detectable immunostaining with the antibody. In addition, three levels of p27 immunostaining have been demonstrated on 1) p27 cells derived from p27 null mice (negative), 2) proliferating rat fibroblasts (intermediate) and 3) serum starved quiescent cells (high) and confirmed by immunoblotting (unpublished results).

Immunohistochemical Studies

All scoring and interpretations of immunocytochemical results were made by a single pathologist (PLP), without knowledge of clinical outcome, other clinical variables or tumor markers. Blocks for testing were selected for presence of representative tumor and, when available, presence of adjacent benign epithelium. Immunostaining was done using a modification of standard immunoperoxidase technique which included microwave treatment of the tissue sections in the presence of citrate buffer[26].

Four high power fields (400× magnification) from a single representative tissue section, chosen to reflect the area of highest cyclin E or p27 intensity, were scored and each tumor section was assigned a single composite value from 0 (negative) to 6 (highest intensity) that reflected staining intensity and the percentage of tumor cells positive. Categories of "high" and "low" cyclin E and p27 immunostaining were determined by comparison of assays in benign breast epithelium. For cyclin E, "low" intensity included all values of 0–3 (98% of benign epithelial samples) and "high" included values from 4–6 (2% of benign epithelial samples). Levels of staining for p27 in benign epithelium ranged widely from values of 2–6, and staining above levels 0–1 was almost always present (77%). "Low", "intermediate", and "high" categories of p27 expression were assigned as 0–1, 2–3, and 4–6 respectively. For regression analysis, intermediate and high categories were combined and compared to low. Five percent of the cyclin E and p27 assays were re-scored for a reliability assessment, blinded to the first reading. Categories of staining intensity never varied by more than 1 integer and there were no instances where the difference in the first and second review resulted in changing the case from one summary category ("high" vs. "low") to another.

Statistical Methods

Associations between the cell cycle proteins and covariates were calculated using contingency table methods and tested for significance using Pearson's chi-square test. Survival curves were calculated using the Kaplan-Meier method. These curves are used to graphically display subset comparisons and are not intended to characterize absolute mortality rates within the cohort particularly since the sampled subset has an over representation of deceased women. Univariate and multivariate relative risks were computed using Cox proportional hazards regression where observations for this subset of women have been weighted proportional to the inverse of their sampling probability with respect to the larger study. Such weighting allows valid estimation of relative risks in non-standard sampling schemes such as survey data or where covariates are missing [27, 28]. We used sampling weights that depend on vital status and year of diagnosis as discussed in the patient population section above. All calculations were performed using S+ version 3.3 (StatSci, WA, USA).

References for Example 3

1. Clurman, B. & Roberts, J. Cell cycle and cancer. *J. Natl Cancer Inst* 87, 1499–1501 (1995).
2. Pietenpol, J. et al. Assignment of the human p27Kip1 gene to 12p13 and its analysis in leukemias. *Cancer Research* 55, 1206–1210 (1995).
3. Bhatia, K. et al. A mutant p21 cyclin-dependent kinase inhivitor isolated from a Burkitt's lymphoma. *Can Res* 55, 1431–1435 (1995).
4. Ponce-Castaneda, M. et al. p27$^{KiP1}$: Chromosomal mapping to 12p12–12p13.1 and absence of mutations in human tumors. *Can Res* 55, 1211–1214 (1995).
5. Konstantin, S. et al. p27/Kip1 mutation found in breast cancer. *Cancer Res* 56, 2400–2404 (1996).
6. Leach, F. et al. Amplification of cyclin genes in colorectal carcinomas. *Cancer Res* 53, 1986–1989 (1993).
7. Keyomarsi, K. et al. Cyclin E, a potential prognostic marker for breast cancer. *Cancer Res* 54, 380–385 (1994).
8. Keyomarsi, K. & Pardee, A. Redundant cyclin overexpression and gene amplification in breast cancer cells. *Proc Natl Acad Sci, USA* 90, 1112–1116 (1993).
9. Said, T. & Medina, D. Cell cyclins and cyclin-dependent kinase activities in mouse mammary tumor development. *Carcinogenesis* 16, 823–830 (1995).
10. Fero M L et al. A syndrome of multi-organ hyperplasia with features of gigantism, tumorigenesis and female sterility in p27Kip 1-deficient mice. *Cell* (1996).
11. Kiyokawa, H. et al. Enhanced growth of mice lacking the cyclin-dependent kinase inhibitor function of p27Kip1. *Cell* 85, 721–732 (1996).
12. Nakayama, K. et al. Mice lacking p27Kip1 desplay increased body size, multiple organ hyperplasia, retinal dysplasia and pituitary tumors. *Cell* 85, 707–720 (1996).
13. Clurman, B., Sheaff, R., Thress, K., Groudine, M. & Roberts, J. Turnover of cyclin E by the ubiquitin-proteosome pathway is regulated by CDK2 binding and cyclin phosphorylation. *Genes & Devel* in press(1996).
14. Pagano, M. et al. Role of the ubiquitin-proteosome pathway in regulating abundance of the cyclin-dependent kinase inhibitor p27. *Science* 269, 682–685 (1995).
15. Dulic, V., Lees, E. & Reed, S. Association of human cyclin E with a periodic G1-S phase protein kinase. *Science* 257, 1958–1961 (1992).
16. Koff, A. et al. Human cyclin E, a new cyclin that interacts with two members of the CDC2 gene family. *Cell* 66, 1217–1228 (1991).
17. Firpo, E., Koff, A., Solomon, M. & Roberts, J. Inactivation of a Cdk2 inhibitor during interleukin 2-induced proliferation of human lumphocytes. *Mol Cell Biol* 14, 4889–4901 (1994).
18. Nourse, J. et aL Interleukin-2-mediated elimination of p27Kip1 cyclin-dependent kinase inhibitor prevented by rapamycin. *Nature* (London) 372, 570–573 (1994).
19. Coats, S., Flannagan, W., Nourse, J. & Roberts, J. Requirement of p27Kip1 for restriction point control of the fibroblast cell cycle. *Science* in press(1996).
20. McGuire, W. & Clark, G. Prognostic factors and treatment decisions in axillary-node negative breast cancer. *NEJM* 326, 1756–1761 (1992).
21. Conference, N.C. Treatment of early-stage breast cancer. *JAA* 265, 391–398 (1991).
22. Gong, J., Ardelt, B., Traganos, F. & Darzynkiewicz, Z. Unscheduled expression of cyclin B 1 and cyclin E in several leukemic and solid tumor cell lines. *Cancer Res* 54, 4285–4288 (1994).
23. Dutta, A., Chandra, R., Leiter, L. & Lester, S. Cyclins as markers of tumor proliferation: Immunocytochemical studies in breast cancer. *PNAS* 92, 5386–5390 (1995).
24. Ohtsubo, M., Theodoras, A., Schumacher, J., Roberts, J. & Pagano, M. Human Cyclin E, a nuclear protein essential for the G1-toS phase transition. *Mol Cell Biol* 15, 2612–2624 (1995).
25. Ohtsubo, M. & Roberts, J. Cyclin-dependent regulation of G1 in mammalian fibroblasts. *Science* 259, 1908–1912 (1993).
26. Gerdes, J., Becker, M. & Key, G. Immunohistological detection of tumour growth fraction (Ki-67 antigen) in formalin-fixed and routinely processed tissues. *J Pathol* 168, 85–86 (1992).
27. Lin, D. & Ying, Z. Cox regression with incomplete covariate measurements. *J. Am Stat Assoc* 88, 1341–1349 (1993).
28. Binder, D. Fitting Cox's proportional hazards models from survey data. *Biometrika* 79, 139–147 (1992).

What is claimed is:

1. A method for determining the relative amount of p27 protein in a cell or sample of cells (cell sample) comprising (i) determining the level of a p27 protein having a sequence of one of SEQ ID Nos. 2, 4, and 6 in the cell sample, and (ii) comparing the level of the p27 protein in the cell sample with the level of a wild-type p27 protein determined for a control cell, wherein the wild-type p27 protein inhibits activation of a cyclin E-Cdk2 (cyclin-dependent kinase-2) complex and has an amino acid sequence of one of SEQ ID Nos. 2, 4, and 6.

2. A method for diagnosing a hyperproliferative disorder characterized by abnormal cell proliferation in a patient, comprising: (i) ascertaining the level of a p27 protein having an amino acid sequence of one of SEQ ID Nos. 2, 4, and 6 in a sample of cells from the patient; and (ii) diagnosing the presence or absence of a hyperproliferative disorder including utilizing the ascertained level of the p27 protein, wherein a reduced level of the p27 protein in the sample, relative to a level of a wild-type p27 protein in a control sample of normal cells, correlates with the presence of a hyperproliferative disorder, and the wild-type p27 protein inhibits activation of a cyclin E-Cdk2 (cyclin-dependent kinase) complex and has an amino acid sequence of one of SEQ ID Nos. 2, 4, and 6.

3. A method for evaluating a cancer patient's prognosis, comprising (i) ascertaining the level of a p27 protein having an amino acid sequence of one of SEO ID Nos. 2, 4, and 6 in a sample of cancer cells from the patient; and (ii) comparing the ascertained level of the p27 protein to a level of wild-type p27 protein in a normal control sample of cells, wherein a reduced level of the p27 protein in the sample correlates with an increased risk of recurrence of a cancer, and wherein the wild-type p27 protein inhibits activation of a cyclin E-Cdk2 (cyclin-dependent kinase-2) complex and has an amino acid sequence of one of SEQ ID Nos. 2, 4, and 6.

4. A method for determining the relative amount of p27 protein in a cell or sample of transformed cells (cell sample) from a patient comprising (i) determining the level of p27 protein having an amino acid sequence of one of SEQ ID Nos. 2, 4, and 6 in the cell sample, and (ii) comparing the level of p27 protein in the cell sample with the level of p27 protein determined for a control cell, wherein the p27 protein inhibits activation of a cyclin E-Cdk2 (cyclin-dependent kinase) complex and has an amino acid sequence of one of SEQ ID Nos. 2, 4, and 6.

5. The method of any one of claims 1, 2 or 3, wherein the level of p27 protein is determined by chromatography or electrophoresis.

6. The method of any one of claims 2 or 3, wherein the patient is a human.

7. The method of claim 2, wherein the hyperproliferative disorder is cancer.

8. The method of claim 3 or 7, wherein the cancer is a cancer of an epithelial tissue.

9. The method of claim 3 or 7, wherein the cancer is a cancer selected from the group consisting of carcinomas, melanomas and sarcomas.

10. The method of claim 9, wherein the cancer is a carcinoma of a tissue selected from the group consisting of breast, ovaries, lung, intestinal, pancreas, prostate, testis, liver, skin, stomach, renal, cervical and colorectal.

11. The method of claim 9, wherein the cancer is a breast carcinoma.

12. The method of claim 11, wherein the breast carcinoma is a ductal carcinoma, a mucinous carcinoma or a lobular carcinoma.

13. The method of claim 3, wherein the cancer is a node-negative breast carcinoma.

* * * * *

UNITED STATES PATENT AND TRADEMARK OFFICE
CERTIFICATE OF CORRECTION

PATENT NO. : 6,316,208 B1
DATED : November 13, 2001
INVENTOR(S) : Roberts et al.

It is certified that error appears in the above-identified patent and that said Letters Patent is hereby corrected as shown below:

<u>Title page,</u>
Under Related U.S. Application Data, please add the following text:
Line 63, after the text Continuation-in-part of application No.:
--08/765,702, filed on Apr. 28, 1997, which is a national-stage filing under 35 U.S.C. § 371 of PCT application No. --

<u>Column 66,</u>
Line 51, please delete the word "SEO" and replace with -- SEQ --

Signed and Sealed this

Sixteenth Day of April, 2002

Attest:

JAMES E. ROGAN
*Attesting Officer*   *Director of the United States Patent and Trademark Office*

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 597 base pairs

```
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..594

(xi) SEQUENCE DESCRIPTION: SEQ ID NO:1:

ATG TCA AAC GTG CGA GTG TCT AAC GGG AGC CCT AGC CTG GAG CGG ATG      48
Met Ser Asn Val Arg Val Ser Asn Gly Ser Pro Ser Leu Glu Arg Met
 1               5                  10                  15

GAC GCC AGG CAG GCG GAG CAC CCC AAG CCC TCG GCC TGC AGG AAC CTC      96
Asp Ala Arg Gln Ala Glu His Pro Lys Pro Ser Ala Cys Arg Asn Leu
             20                  25                  30

TTC GGC CCG GTG GAC CAC GAA GAG TTA ACC CGG GAC TTG GAG AAG CAC     144
Phe Gly Pro Val Asp His Glu Glu Leu Thr Arg Asp Leu Glu Lys His
         35                  40                  45

TGC AGA GAC ATG GAA GAG GCG AGC CAG CGC AAG TGG AAT TTC GAT TTT     192
Cys Arg Asp Met Glu Glu Ala Ser Gln Arg Lys Trp Asn Phe Asp Phe
 50                  55                  60

CAG AAT CAC AAA CCC CTA GAG GGC AAG TAC GAG TGG CAA GAG GTG GAG     240
Gln Asn His Lys Pro Leu Glu Gly Lys Tyr Glu Trp Gln Glu Val Glu
 65                  70                  75                  80

AAG GGC AGC TTG CCC GAG TTC TAC TAC AGA CCC CCG CGG CCC CCC AAA     288
Lys Gly Ser Leu Pro Glu Phe Tyr Tyr Arg Pro Pro Arg Pro Pro Lys
                 85                  90                  95

GGT GCC TGC AAG GTG CCG GCG CAG GAG AGC CAG GAT GTC AGC GGG AGC     336
Gly Ala Cys Lys Val Pro Ala Gln Glu Ser Gln Asp Val Ser Gly Ser
            100                 105                 110

CGC CCG GCG GCG CCT TTA ATT GGG GCT CCG GCT AAC TCT GAG GAC ACG     384
Arg Pro Ala Ala Pro Leu Ile Gly Ala Pro Ala Asn Ser Glu Asp Thr
        115                 120                 125

CAT TTG GTG GAC CCA AAG ACT GAT CCG TCG GAC AGC CAG ACG GGG TTA     432
His Leu Val Asp Pro Lys Thr Asp Pro Ser Asp Ser Gln Thr Gly Leu
    130                 135                 140

GCG GAG CAA TGC GCA GGA ATA AGG AAG CGA CCT GCA ACC GAC GAT TCT     480
Ala Glu Gln Cys Ala Gly Ile Arg Lys Arg Pro Ala Thr Asp Asp Ser
145                 150                 155                 160

TCT ACT CAA AAC AAA AGA GCC AAC AGA ACA GAA GAA AAT GTT TCA GAC     528
Ser Thr Gln Asn Lys Arg Ala Asn Arg Thr Glu Glu Asn Val Ser Asp
                165                 170                 175

GGT TCC CCA AAT GCC GGT TCT GTG GAG CAG ACG CCC AAG AAG CCT GGC     576
Gly Ser Pro Asn Ala Gly Ser Val Glu Gln Thr Pro Lys Lys Pro Gly
            180                 185                 190

CTC AGA AGA CGT CAA ACG TAA                                         597
Leu Arg Arg Arg Gln Thr
        195

(2) INFORMATION FOR SEQ ID NO:2:

(i) SEQUENCE CHARACTERISTICS:
        (A) LENGTH: 198 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Asn Val Arg Val Ser Asn Gly Ser Pro Ser Leu Glu Arg Met
 1               5                  10                  15
```

```
Asp Ala Arg Gln Ala Glu His Pro Lys Pro Ser Ala Cys Arg Asn Leu
             20                  25                  30

Phe Gly Pro Val Asp His Glu Glu Leu Thr Arg Asp Leu Glu Lys His
         35                  40                  45

Cys Arg Asp Met Glu Glu Ala Ser Gln Arg Lys Trp Asn Phe Asp Phe
 50                  55                  60

Gln Asn His Lys Pro Leu Glu Gly Lys Tyr Glu Trp Gln Glu Val Glu
 65                  70                  75                  80

Lys Gly Ser Leu Pro Glu Phe Tyr Tyr Arg Pro Pro Arg Pro Pro Lys
                 85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
            115                 120                 125

His Leu Val Asp Pro Lys Thr Asp Pro Ser Asp Ser Gln Thr Gly Leu
        130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
            195

(2) INFORMATION FOR SEQ ID NO:3:

(i) SEQUENCE CHARACTERISTICS:
        (A) LENGTH: 594 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..591

(xi) SEQUENCE DESCRIPTION: SEQ ID NO:3:

ATG TCA AAC GTG AGA GTG TCT AAC GGG AGC CCG AGC CTG GAG CGG ATG      48
Met Ser Asn Val Arg Val Ser Asn Gly Ser Pro Ser Leu Glu Arg Met
 1               5                  10                  15

GAC GCC AGA CAA GCG GAT CAC CCC AAG CCT TCC GCC TGC AGA AAT CTC      96
Asp Ala Arg Gln Ala Asp His Pro Lys Pro Ser Ala Cys Arg Asn Leu
             20                  25                  30

TTC GGC CCG GTC AAT CAT GAA GAA CTA ACC CGG GAC TTG GAG AAG CAC     144
Phe Gly Pro Val Asn His Glu Glu Leu Thr Arg Asp Leu Glu Lys His
         35                  40                  45

TGC CGG GAT ATG GAA GAA GCG AGT CAG CGC AAG TGG AAT TTC GAC TTT     192
Cys Arg Asp Met Glu Glu Ala Ser Gln Arg Lys Trp Asn Phe Asp Phe
 50                  55                  60

CAG AAT CAT AAG CCC CTG GAG GGC AGA TAC GAA TGG CAG GAG GTG GAG     240
Gln Asn His Lys Pro Leu Glu Gly Arg Tyr Glu Trp Gln Glu Val Glu
 65                  70                  75                  80

AGG GGC AGC TTG CCC GAG TTC TAC TAC AGG CCC CCG CGC CCC CCC AAG     288
Arg Gly Ser Leu Pro Glu Phe Tyr Tyr Arg Pro Pro Arg Pro Pro Lys
                 85                  90                  95

AGC GCC TGC AAG GTG CTG GCG CAG GAG AGC CAG GAT GTC AGC GGG AGC     336
Ser Ala Cys Lys Val Leu Ala Gln Glu Ser Gln Asp Val Ser Gly Ser
```

```
CGC CAG GCG GTG CCT TTA ATT GGG TCT CAG GCA AAC TCT GAG GAC CGG    384
Arg Gln Ala Val Pro Leu Ile Gly Ser Gln Ala Asn Ser Glu Asp Arg
        115                 120                 125

CAT TTG GTG GAC CAA ATG CCT GAC TCG TCA GAC AAT CAG GCT GGG TTA    432
His Leu Val Asp Gln Met Pro Asp Ser Ser Asp Asn Gln Ala Gly Leu
    130                 135                 140

GCG GAG CAG TGT CCA GGG ATG AGG AAG CGA CCT GCT GCA GAA GAT TCT    480
Ala Glu Gln Cys Pro Gly Met Arg Lys Arg Pro Ala Ala Glu Asp Ser
145                 150                 155                 160

TCT TCG CAA AAC AAA AGG GCC AAC AGA ACA GAA GAA AAT GTT TCA GAC    528
Ser Ser Gln Asn Lys Arg Ala Asn Arg Thr Glu Glu Asn Val Ser Asp
                165                 170                 175

GGT TCC CCG AAC GCT GGC ACT GTG GAG CAG ACG CCC AAG AAG CCC GGC    576
Gly Ser Pro Asn Ala Gly Thr Val Glu Gln Thr Pro Lys Lys Pro Gly
            180                 185                 190

CTT CGA CGC CAG ACG TAA                                             594
Leu Arg Arg Gln Thr
        195
```

(2) INFORMATION FOR SEQ ID NO:4:

(i) SEQUENCE CHARACTERISTICS:
        (A) LENGTH: 197 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Asn Val Arg Val Ser Asn Gly Ser Pro Ser Leu Glu Arg Met
1               5                   10                  15

Asp Ala Arg Gln Ala Asp His Pro Lys Pro Ser Ala Cys Arg Asn Leu
                20                  25                  30

Phe Gly Pro Val Asn His Glu Glu Leu Thr Arg Asp Leu Glu Lys His
            35                  40                  45

Cys Arg Asp Met Glu Glu Ala Ser Gln Arg Lys Trp Asn Phe Asp Phe
    50                  55                  60

Gln Asn His Lys Pro Leu Glu Gly Arg Tyr Glu Trp Gln Glu Val Glu
65                  70                  75                  80

Arg Gly Ser Leu Pro Glu Phe Tyr Tyr Arg Pro Pro Arg Pro Pro Lys
                85                  90                  95

Ser Ala Cys Lys Val Leu Ala Gln Glu Ser Gln Asp Val Ser Gly Ser
                100                 105                 110

Arg Gln Ala Val Pro Leu Ile Gly Ser Gln Ala Asn Ser Glu Asp Arg
            115                 120                 125

His Leu Val Asp Gln Met Pro Asp Ser Ser Asp Asn Gln Ala Gly Leu
    130                 135                 140

Ala Glu Gln Cys Pro Gly Met Arg Lys Arg Pro Ala Ala Glu Asp Ser
145                 150                 155                 160

Ser Ser Gln Asn Lys Arg Ala Asn Arg Thr Glu Glu Asn Val Ser Asp
                165                 170                 175

Gly Ser Pro Asn Ala Gly Thr Val Glu Gln Thr Pro Lys Lys Pro Gly
            180                 185                 190

Leu Arg Arg Gln Thr
        195
```

(2) INFORMATION FOR SEQ ID NO:5:

(i) SEQUENCE CHARACTERISTICS:
    (A) LENGTH: 534 base pairs
    (B) TYPE: nucleic acid
    (C) STRANDEDNESS: both
    (D) TOPOLOGY: linear (ii) MOLECULE TYPE: cDNA (ix) FEATURE:
    (A) NAME/KEY: CDS
    (B) LOCATION: 1..534

(xi) SEQUENCE DESCRIPTION: SEQ ID NO:5:

```
ATG TCA AAC GTG CGG GTG TCT AAC GGG AGC CCG AGC CTG GAG CGG ATG      48
Met Ser Asn Val Arg Val Ser Asn Gly Ser Pro Ser Leu Glu Arg Met
 1               5                  10                  15

GAC GCC AGA CAG GCG GAG TAC CCC AAG CCC TCC GCC TGC AGA AAC CTC      96
Asp Ala Arg Gln Ala Glu Tyr Pro Lys Pro Ser Ala Cys Arg Asn Leu
                20                  25                  30

TTC GGC CCG GTC AAC CAC GAA GAG CTG ACC CGG GAC TTG GAG AAG CAC     144
Phe Gly Pro Val Asn His Glu Glu Leu Thr Arg Asp Leu Glu Lys His
             35                  40                  45

CGC AGA GAC ATG GAA GAG GCA AGC CAG CGC AAG TGG AAT TTT GAT TTC     192
Arg Arg Asp Met Glu Glu Ala Ser Gln Arg Lys Trp Asn Phe Asp Phe
 50                  55                  60

CAG AAT CAC AAG CCC CTG GAG GGC AAA TAC GAG TGG CAG GAG GTG GAG     240
Gln Asn His Lys Pro Leu Glu Gly Lys Tyr Glu Trp Gln Glu Val Glu
 65                  70                  75                  80

AAG GGC AGC TTG CCG GAG TTC TAC TAC AGA CCC CCG CGG CCA CCC AAA     288
Lys Gly Ser Leu Pro Glu Phe Tyr Tyr Arg Pro Pro Arg Pro Pro Lys
                 85                  90                  95

GGC GCC TGC AAG GTG CCG GCG CAG GAG AGC CAG GAC GTC AGC GGG ACC     336
Gly Ala Cys Lys Val Pro Ala Gln Glu Ser Gln Asp Val Ser Gly Thr
                100                 105                 110

CGG CAG GCC GTG CCT TTA ATG GGG TCT CAG GCA AAC TCA GAG GAC ACA     384
Arg Gln Ala Val Pro Leu Met Gly Ser Gln Ala Asn Ser Glu Asp Thr
            115                 120                 125

CAC TTG GTA GAC CAA AAG ACT GAC ACG GCG GAC AAC CAG GCT GGC TTA     432
His Leu Val Asp Gln Lys Thr Asp Thr Ala Asp Asn Gln Ala Gly Leu
130                 135                 140

GCG GAG CAG TGC ACT GGG ATC AGG AAG CGA CCG GCC ACA GAC GAT TCC     480
Ala Glu Gln Cys Thr Gly Ile Arg Lys Arg Pro Ala Thr Asp Asp Ser
145                 150                 155                 160

TCT CCT CAA AAC AAA AGA GCC AAC AGA ACA GAA GAA AAT GTC TCA GAC     528
Ser Pro Gln Asn Lys Arg Ala Asn Arg Thr Glu Glu Asn Val Ser Asp
                165                 170                 175

GGT TCC                                                              534
Gly Ser
```

(2) INFORMATION FOR SEQ ID NO:6:

(i) SEQUENCE CHARACTERISTICS:
        (A) LENGTH: 178 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ser Asn Val Arg Val Ser Asn Gly Ser Pro Ser Leu Glu Arg Met
 1               5                  10                  15

Asp Ala Arg Gln Ala Glu Tyr Pro Lys Pro Ser Ala Cys Arg Asn Leu
                20                  25                  30
```

```
Phe Gly Pro Val Asn His Glu Glu Leu Thr Arg Asp Leu Glu Lys His
         35                  40                  45

Arg Arg Asp Met Glu Glu Ala Ser Gln Arg Lys Trp Asn Phe Asp Phe
     50                  55                  60

Gln Asn His Lys Pro Leu Glu Gly Lys Tyr Glu Trp Gln Glu Val Glu
 65                  70                  75                  80

Lys Gly Ser Leu Pro Glu Phe Tyr Tyr Arg Pro Arg Pro Pro Lys
                 85                  90                  95

Gly Ala Cys Lys Val Pro Ala Gln Glu Ser Gln Asp Val Ser Gly Thr
                100                 105                 110

Arg Gln Ala Val Pro Leu Met Gly Ser Gln Ala Asn Ser Glu Asp Thr
        115                 120                 125

His Leu Val Asp Gln Lys Thr Asp Thr Ala Asp Asn Gln Ala Gly Leu
    130                 135                 140

Ala Glu Gln Cys Thr Gly Ile Arg Lys Arg Pro Ala Thr Asp Asp Ser
145                 150                 155                 160

Ser Pro Gln Asn Lys Arg Ala Asn Arg Thr Glu Glu Asn Val Ser Asp
                165                 170                 175

Gly Ser (2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Asn Leu Tyr Pro Leu Thr Asn Tyr Thr Phe
1               5                   10

(2) INFORMATION FOR SEQ ID NO:8:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Thr Asp Thr Ala Asp Asn Gln Ala Gly Leu Ala Glu Gln
1               5                   10

(2) INFORMATION FOR SEQ ID NO:9:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Gln Ala Val Pro Leu Met Gly Pro Gln Glu
1               5                   10
```

(2) INFORMATION FOR SEQ ID NO:10:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

```
Leu Pro Glu Phe Tyr Tyr Arg Pro Pro Arg Pro Pro
1               5                   10
```

(2) INFORMATION FOR SEQ ID NO:11:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

```
Tyr Glu Trp Gln Glu Val
1               5
```

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:12:

ACNGAYACNG AYAAYCARGC                                20

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:13:

NGCYTGRTTR TCNGCNGTRT CNGT                          24

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:14:

CARGCNGTNC CNCTNATGGG                                20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:15:

CARGCNGTNC CNTTRATGGG                                                         20

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:16:

NCCCATNAGN GGNACNGCYT G                                                  21

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:17:

NCCCATYAAN GGNACNGCYT G                                                21

(2) INFORMATION FOR SEQ ID NO:18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:18:

CCNGARTTYT AYTAYMG                                                            17

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:19:

CKRTARTARA AYTCNGG                                                            17

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:20:

TAYGARTGGC ARGARGT                                            17

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:21:

NACYTCYTGC CAYTCRTA                                          18

(2) INFORMATION FOR SEQ ID NO:22:

(i) SEQUENCE CHARACTERISTICS:
        (A) LENGTH: 198 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:22:

```
Met Ser Asn Val Arg Val Ser Asn Gly Ser Pro Ser Leu Glu Arg Met
 1               5                  10                  15

Asp Ala Arg Gln Ala Glu Tyr Pro Lys Pro Ser Ala Cys Arg Asn Leu
             20                  25                  30

Phe Gly Pro Val Asn His Glu Glu Leu Thr Arg Asp Leu Glu Lys His
         35                  40                  45

Arg Arg Asp Met Glu Glu Ala Ser Gln Arg Lys Trp Asn Phe Asp Phe
     50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                 85                  90                  95

Gly Ala Cys Lys Val Pro Ala Gln Glu Ser Gln Asp Val Ser Gly Thr
            100                 105                 110

Arg Gln Ala Val Pro Leu Met Gly Ser Gln Ala Asn Ser Glu Asp Thr
        115                 120                 125

His Leu Val Asp Gln Lys Thr Asp Thr Ala Asp Asn Gln Ala Gly Leu
    130                 135                 140

Ala Glu Gln Cys Thr Gly Ile Arg Lys Arg Pro Ala Thr Asp Asp Ser
145                 150                 155                 160

Ser Pro Gln Asn Lys Arg Ala Asn Arg Thr Glu Glu Asn Val Ser Asp
                165                 170                 175
```

```
                                    -continued

Gly Ser Xaa Xaa Xaa Xaa Xaa Xaa Xaa Xaa Xaa Xaa Xaa Xaa
            180                 185                 190

Xaa Xaa Xaa Xaa Xaa Xaa
        195

(2) INFORMATION FOR SEQ ID NO:23:

(i) SEQUENCE CHARACTERISTICS:
        (A) LENGTH: 164 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:23:

Met Ser Glu Pro Ala Gly Asp Val Arg Gln Asn Pro Cys Gly Ser Phe
1               5                   10                  15

Ala Cys Pro Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Phe
        35                  40                  45

Trp Asn Phe Asp Phe Val Thr Glu Thr Pro Leu Glu Gly Asp Phe Ala
    50                  55                  60

Trp Glu Phe Val Arg Gly Leu Gly Leu Pro Lys Leu Tyr Leu Pro Thr
65                  70                  75                  80

Gly Pro Arg Arg Gly Arg Asp Glu Leu Gly Gly Gly Arg Arg Pro Gly
                85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Cys Gly Arg Lys Pro Arg Cys
        130                 135                 140

Thr Ser Met Thr Asp Phe Tyr His Ser Lys Arg Arg Leu Ile Phe Ser
145                 150                 155                 160

Lys Arg Lys Pro
```